US008505535B2

(12) United States Patent  
Jones et al.

(10) Patent No.: US 8,505,535 B2
(45) Date of Patent: Aug. 13, 2013

(54) MASK SYSTEM

(75) Inventors: Michael Andrew Jones, Dundas (AU); Amal Shirley Amarasinghe, West Pennant Hills (AU); Timothy Tsun-Fai Fu, Carlingford (AU); Perry David Lithgow, Moruya (AU); Jim Saada, Kellyville (AU); Fiachra Marcus Sweeney, North Bondi (AU)

(73) Assignee: ResMed Limited, Bella Vista (AU)

( * ) Notice: Subject to any disclaimer, the term of this patent is extended or adjusted under 35 U.S.C. 154(b) by 832 days.

(21) Appl. No.: 12/654,595

(22) Filed: Dec. 23, 2009

(65) Prior Publication Data

US 2011/0030692 A1  Feb. 10, 2011

Related U.S. Application Data

(62) Division of application No. 10/555,301, filed as application No. PCT/AU2004/000563 on Apr. 30, 2004, now Pat. No. 7,861,715.

(30) Foreign Application Priority Data

May 2, 2003 (AU) ................................ 2003902098
Mar. 26, 2004 (AU) ................................ 2004901648

(51) Int. Cl.
 *A62B 18/02* (2006.01)
(52) U.S. Cl.
 CPC ....................................... *A62B 18/02* (2013.01)
 USPC ................................. 128/204.21; 128/205.25
(58) Field of Classification Search
 USPC ............ 128/206.21, 206.24, 206.27, 206.28, 128/207.13, 205.25
 See application file for complete search history.

(56) References Cited

U.S. PATENT DOCUMENTS

| | | | |
|---|---|---|---|
| 364,394 A | 6/1887 | Bright |
| 428,592 A | 5/1890 | Chapman |
| 781,516 A | 1/1905 | Guthrie |
| 812,706 A | 2/1906 | Warbasse |
| 1,081,745 A | 12/1913 | Johnston et al. |
| 1,176,886 A | 3/1916 | Ermold |
| 1,192,186 A | 7/1916 | Greene |
| 1,206,045 A | 11/1916 | Smith |
| 1,502,450 A | 7/1924 | Wood |
| 1,610,793 A | 12/1926 | Kaufman |
| 1,632,449 A | 6/1927 | McKesson |

(Continued)

FOREIGN PATENT DOCUMENTS

| | | |
|---|---|---|
| AU | 91/77110 | 11/1991 |
| AU | 94/64816 | 12/1994 |

(Continued)

OTHER PUBLICATIONS

Chinese Office Action and English translation for co-pending Chinese Application No. 200480011911.9, mailed Jun. 24, 2010, 12 pages.

(Continued)

*Primary Examiner* — Steven Douglas
(74) *Attorney, Agent, or Firm* — Nixon & Vanderhye P.C.

(57) ABSTRACT

A mask system for treating sleep disordered breathing, comprising headgear, a shell/cushion including a channel adjacent a front aperture, a frame, an elbow including at least one undercut on a proximal end, a retaining ring including a rear flange adapted to be retainably insertable in the channel of the shell/cushion, and a front flange adapted to retainably engage with the at least one undercut of the elbow.

145 Claims, 65 Drawing Sheets

(56) References Cited

U.S. PATENT DOCUMENTS

| | | |
|---|---|---|
| 1,653,572 A | 12/1927 | Jackson |
| 1,837,591 A | 12/1931 | Shindel |
| 1,926,027 A | 9/1933 | Biggs |
| 2,123,353 A | 7/1938 | Catt |
| 2,127,136 A | 8/1938 | Pobirs |
| 2,149,067 A | 2/1939 | Otero |
| 2,245,658 A | 6/1941 | Erickson |
| 2,245,969 A | 6/1941 | Francisco et al. |
| 2,248,477 A | 7/1941 | Lombard |
| 2,254,854 A | 9/1941 | O'Connell |
| 2,317,608 A | 4/1943 | Heidbrink |
| 2,371,965 A | 3/1945 | Lehmberg |
| 2,376,871 A | 5/1945 | Fink |
| 2,382,364 A | 8/1945 | Yant |
| 2,415,846 A | 2/1947 | Randall |
| 2,438,058 A | 3/1948 | Kincheloe |
| 2,473,518 A | 6/1949 | Garrard et al. |
| D156,060 S | 11/1949 | Wade |
| D161,337 S | 12/1950 | Hill |
| 2,540,567 A | 2/1951 | Bennett |
| 2,578,621 A | 12/1951 | Yant |
| 2,590,006 A | 3/1952 | Gordon |
| 2,625,155 A | 1/1953 | Engelder |
| 2,693,178 A | 11/1954 | Gilroy |
| 2,820,651 A | 1/1958 | Phillips |
| 2,837,090 A | 6/1958 | Bloom et al. |
| 2,868,196 A | 1/1959 | Stampe |
| 2,875,757 A | 3/1959 | Galleher, Jr. |
| 2,902,033 A | 9/1959 | Galleher, Jr. |
| 2,917,045 A | 12/1959 | Schildknecht et al. |
| 2,931,356 A | 4/1960 | Schwarz |
| D188,084 S | 5/1960 | Garelick |
| 2,939,458 A | 6/1960 | Lundquist |
| 3,013,556 A | 12/1961 | Galleher |
| 3,042,035 A | 7/1962 | Coanda |
| 3,117,574 A | 1/1964 | Replogle |
| 3,182,659 A | 5/1965 | Blount et al. |
| 3,189,027 A | 6/1965 | Bartlett |
| 3,193,624 A | 7/1965 | Webb et al. |
| 3,238,943 A | 3/1966 | Holley |
| 3,288,138 A | 11/1966 | Sachs |
| 3,315,672 A | 4/1967 | Cunningham et al. |
| 3,315,674 A | 4/1967 | Bloom et al. |
| 3,330,273 A | 7/1967 | Bennett |
| 3,362,420 A | 1/1968 | Blackburn et al. |
| 3,363,833 A | 1/1968 | Laerdal |
| 3,556,122 A | 1/1971 | Laerdal |
| 3,580,051 A | 5/1971 | Blevins |
| 3,700,000 A | 10/1972 | Hesse et al. |
| 3,720,235 A | 3/1973 | Schrock |
| 3,725,953 A | 4/1973 | Johnson et al. |
| 3,750,333 A | 8/1973 | Vance |
| 3,752,157 A | 8/1973 | Malmin |
| 3,796,216 A | 3/1974 | Schwarz |
| 3,799,164 A | 3/1974 | Rollins |
| D231,803 S | 6/1974 | Huddy |
| 3,830,230 A | 8/1974 | Chester |
| 3,978,854 A | 9/1976 | Mills, Jr. |
| 4,062,357 A | 12/1977 | Laerdal |
| 4,069,516 A | 1/1978 | Watkins |
| 4,077,404 A | 3/1978 | Elam |
| D248,497 S | 7/1978 | Slosek |
| D250,131 S | 10/1978 | Lewis et al. |
| 4,120,302 A | 10/1978 | Ziegler |
| 4,156,426 A | 5/1979 | Gold |
| 4,167,185 A | 9/1979 | Lewis |
| 4,201,205 A | 5/1980 | Bartholomew |
| 4,226,234 A | 10/1980 | Gunderson |
| 4,231,363 A | 11/1980 | Grimes |
| 4,233,972 A | 11/1980 | Hauff et al. |
| 4,245,632 A | 1/1981 | Houston |
| 4,248,218 A | 2/1981 | Fischer |
| 4,266,540 A | 5/1981 | Panzik et al. |
| D262,322 S | 12/1981 | Mizerak |
| 4,304,229 A | 12/1981 | Curtin |
| 4,328,797 A | 5/1982 | Rollins et al. |
| 4,337,767 A | 7/1982 | Yahata |
| 4,347,205 A | 8/1982 | Stewart |
| 4,354,488 A | 10/1982 | Bartos |
| 4,369,284 A | 1/1983 | Chen |
| 4,402,316 A | 9/1983 | Gadberry |
| 4,412,537 A | 11/1983 | Tiger |
| 4,414,973 A | 11/1983 | Matheson et al. |
| 4,417,575 A | 11/1983 | Hilton et al. |
| 4,446,576 A | 5/1984 | Hisataka |
| 4,454,880 A | 6/1984 | Muto et al. |
| 4,454,881 A | 6/1984 | Huber et al. |
| 4,458,679 A | 7/1984 | Ward |
| 4,467,799 A | 8/1984 | Steinberg |
| 4,522,639 A | 6/1985 | Ansite et al. |
| 4,558,710 A | 12/1985 | Eichler |
| 4,572,323 A | 2/1986 | Randall |
| 4,579,113 A | 4/1986 | McCreadie et al. |
| 4,593,688 A | 6/1986 | Payton |
| D285,496 S | 9/1986 | Berman |
| 4,616,647 A | 10/1986 | McCreadie |
| 4,622,964 A | 11/1986 | Flynn |
| 4,655,213 A | 4/1987 | Rapoport et al. |
| 4,657,010 A | 4/1987 | Wright |
| 4,665,570 A | 5/1987 | Davis |
| 4,671,271 A | 6/1987 | Bishop et al. |
| 4,674,134 A | 6/1987 | Lundin |
| 4,676,241 A | 6/1987 | Webb et al. |
| 4,677,975 A | 7/1987 | Edgar et al. |
| 4,677,977 A | 7/1987 | Wilcox |
| 4,686,977 A | 8/1987 | Cosma |
| 4,707,863 A | 11/1987 | McNeal |
| H397 H | 1/1988 | Stark |
| D293,613 S | 1/1988 | Wingler |
| 4,739,755 A | 4/1988 | White et al. |
| 4,770,169 A | 9/1988 | Schmoegner et al. |
| 4,772,760 A | 9/1988 | Graham |
| 4,774,941 A | 10/1988 | Cook |
| 4,782,832 A | 11/1988 | Trimble et al. |
| 4,799,477 A | 1/1989 | Lewis |
| 4,807,617 A | 2/1989 | Nesti |
| 4,809,692 A | 3/1989 | Nowacki et al. |
| 4,811,730 A | 3/1989 | Milano |
| 4,819,629 A | 4/1989 | Jonson |
| 4,821,713 A | 4/1989 | Bauman |
| 4,827,924 A | 5/1989 | Japuntich |
| 4,832,017 A | 5/1989 | Schnoor |
| 4,841,953 A | 6/1989 | Dodrill |
| 4,848,334 A | 7/1989 | Bellm |
| 4,848,366 A | 7/1989 | Aita et al. |
| 4,850,346 A | 7/1989 | Michel et al. |
| 4,856,118 A | 8/1989 | Sapiejewski |
| D304,384 S | 10/1989 | Derobert |
| 4,886,058 A | 12/1989 | Brostrom et al. |
| 4,905,683 A | 3/1990 | Cronjaeger |
| 4,907,584 A | 3/1990 | McGinnis |
| 4,910,806 A | 3/1990 | Baker et al. |
| 4,915,105 A | 4/1990 | Lee |
| 4,915,106 A | 4/1990 | Aulgur et al. |
| 4,919,128 A | 4/1990 | Kopala et al. |
| 4,938,210 A | 7/1990 | Shene |
| 4,938,212 A | 7/1990 | Snook et al. |
| 4,944,310 A | 7/1990 | Sullivan |
| D310,431 S | 9/1990 | Bellm |
| 4,960,121 A | 10/1990 | Nelson et al. |
| 4,971,051 A | 11/1990 | Toffolon |
| 4,986,269 A | 1/1991 | Hakkinen |
| 4,989,271 A | 2/1991 | Sapiejewski et al. |
| 4,989,596 A | 2/1991 | Macris et al. |
| 4,989,599 A | 2/1991 | Carter |
| 5,003,631 A | 4/1991 | Richardson |
| 5,003,633 A | 4/1991 | Itoh |
| 5,005,568 A | 4/1991 | Loescher et al. |
| 5,005,571 A | 4/1991 | Dietz |
| 5,018,519 A | 5/1991 | Brown |
| 5,027,809 A | 7/1991 | Robinson |
| 5,038,776 A | 8/1991 | Harrison et al. |
| 5,042,473 A | 8/1991 | Lewis |
| 5,042,478 A | 8/1991 | Kopala et al. |

| | | |
|---|---|---|
| 5,046,200 A | 9/1991 | Feder |
| 5,062,421 A | 11/1991 | Burns et al. |
| 5,063,922 A | 11/1991 | Hakkinen |
| 5,069,205 A | 12/1991 | Urso |
| 5,074,297 A | 12/1991 | Venegas |
| D323,908 S | 2/1992 | Hollister et al. |
| 5,093,940 A | 3/1992 | Nishiyama |
| 5,109,839 A | 5/1992 | Blasdell et al. |
| 5,109,840 A | 5/1992 | Daleiden |
| 5,121,745 A | 6/1992 | Israel |
| 5,133,347 A | 7/1992 | Huennebeck |
| 5,138,722 A | 8/1992 | Urella et al. |
| 5,140,980 A | 8/1992 | Haughey et al. |
| 5,140,982 A | 8/1992 | Bauman |
| 5,146,914 A | 9/1992 | Sturrock |
| 5,159,938 A | 11/1992 | Laughlin |
| 5,178,138 A | 1/1993 | Walstrom et al. |
| 5,181,506 A | 1/1993 | Tardiff, Jr. et al. |
| D333,015 S | 2/1993 | Farmer |
| D334,633 S | 4/1993 | Rudolph |
| 5,199,424 A | 4/1993 | Sullivan et al. |
| D335,322 S | 5/1993 | Jones |
| 5,220,699 A | 6/1993 | Farris |
| 5,231,983 A | 8/1993 | Matson et al. |
| 5,233,978 A | 8/1993 | Callaway |
| 5,243,971 A | 9/1993 | Sullivan et al. |
| 5,245,995 A | 9/1993 | Sullivan et al. |
| 5,265,595 A | 11/1993 | Rudolph |
| 5,269,296 A | 12/1993 | Landis |
| 5,279,289 A | 1/1994 | Kirk |
| 5,280,784 A | 1/1994 | Kohler |
| 5,291,880 A | 3/1994 | Almovist et al. |
| 5,301,689 A | 4/1994 | Wennerholm |
| 5,311,862 A | 5/1994 | Blasdell et al. |
| 5,322,057 A | 6/1994 | Raabe et al. |
| 5,322,059 A | 6/1994 | Walther |
| 5,331,691 A | 7/1994 | Runckel |
| 5,334,646 A | 8/1994 | Chen |
| 5,343,878 A | 9/1994 | Scarberry et al. |
| 5,349,949 A | 9/1994 | Schegerin |
| 5,357,945 A | 10/1994 | Messina |
| 5,357,951 A | 10/1994 | Ratner |
| 5,372,130 A | 12/1994 | Stern et al. |
| 5,388,571 A | 2/1995 | Roberts et al. |
| 5,390,373 A | 2/1995 | Flory |
| 5,400,781 A | 3/1995 | Davenport |
| 5,404,871 A | 4/1995 | Goodman et al. |
| 5,411,021 A | 5/1995 | Gdulla et al. |
| 5,419,317 A | 5/1995 | Blasdell et al. |
| 5,419,318 A | 5/1995 | Tayebi |
| 5,429,126 A | 7/1995 | Bracken |
| 5,429,683 A | 7/1995 | Le Mitouard |
| 5,431,158 A | 7/1995 | Tirotta |
| 5,438,981 A | 8/1995 | Starr et al. |
| 5,441,046 A | 8/1995 | Starr et al. |
| D362,061 S | 9/1995 | McGinnis et al. |
| 5,477,852 A | 12/1995 | Landis et al. |
| 5,479,920 A | 1/1996 | Piper et al. |
| 5,481,763 A | 1/1996 | Brostrom et al. |
| 5,485,837 A | 1/1996 | Solesbee et al. |
| 5,488,948 A | 2/1996 | Dubruille et al. |
| 5,492,116 A | 2/1996 | Scarberry |
| 5,501,214 A | 3/1996 | Sabo |
| 5,509,404 A | 4/1996 | Lloyd et al. |
| 5,511,541 A | 4/1996 | Dearstine |
| 5,517,986 A | 5/1996 | Starr et al. |
| 5,522,382 A | 6/1996 | Sullivan et al. |
| 5,538,000 A | 7/1996 | Rudolph |
| 5,538,001 A | 7/1996 | Bridges |
| 5,540,223 A | 7/1996 | Starr et al. |
| 5,542,128 A | 8/1996 | Lomas |
| 5,546,936 A | 8/1996 | Virag et al. |
| 5,558,090 A | 9/1996 | James |
| RE35,339 E | 10/1996 | Rapoport |
| 5,560,354 A | 10/1996 | Berthon-Jones et al. |
| 5,570,682 A | 11/1996 | Johnson |
| 5,570,684 A | 11/1996 | Behr |
| 5,570,689 A | 11/1996 | Starr et al. |
| 5,575,278 A | 11/1996 | Bonhomme et al. |
| D377,089 S | 12/1996 | Starr et al. |
| 5,592,937 A | 1/1997 | Freund |
| 5,592,938 A | 1/1997 | Scarberry et al. |
| 5,608,647 A | 3/1997 | Rubsamen et al. |
| 5,617,849 A | 4/1997 | Springett et al. |
| 5,642,730 A | 7/1997 | Baran |
| 5,645,054 A | 7/1997 | Cotner et al. |
| 5,647,355 A | 7/1997 | Starr et al. |
| 5,647,357 A | 7/1997 | Barnett |
| 5,649,532 A | 7/1997 | Griffiths |
| 5,649,533 A | 7/1997 | Oren |
| 5,655,520 A | 8/1997 | Howe et al. |
| 5,655,527 A | 8/1997 | Scarberry et al. |
| 5,657,493 A | 8/1997 | Ferrero et al. |
| 5,657,752 A | 8/1997 | Landis et al. |
| 5,660,174 A | 8/1997 | Jacobelli |
| 5,662,101 A | 9/1997 | Ogden et al. |
| 5,666,946 A | 9/1997 | Langenback |
| D385,960 S | 11/1997 | Rudolph |
| 5,685,296 A | 11/1997 | Zdrojkowski et al. |
| 5,687,715 A | 11/1997 | Landis et al. |
| 5,704,345 A | 1/1998 | Berthon-Jones |
| 5,709,204 A | 1/1998 | Lester |
| 5,715,814 A | 2/1998 | Ebers |
| 5,724,964 A | 3/1998 | Brunson et al. |
| 5,724,965 A | 3/1998 | Handke et al. |
| 5,740,795 A | 4/1998 | Brydon |
| 5,746,201 A | 5/1998 | Kidd |
| 5,794,617 A | 8/1998 | Brunell et al. |
| D398,987 S | 9/1998 | Cotner et al. |
| 5,813,423 A | 9/1998 | Kirchgeorg |
| 5,832,918 A | 11/1998 | Pantino |
| D402,755 S | 12/1998 | Kwok |
| RE36,165 E | 3/1999 | Behr |
| 5,884,624 A | 3/1999 | Barnett et al. |
| 5,896,857 A | 4/1999 | Hely et al. |
| 5,909,732 A | 6/1999 | Diesel et al. |
| 5,921,239 A | 7/1999 | McCall |
| 5,937,851 A | 8/1999 | Serowski et al. |
| 5,966,745 A | 10/1999 | Schwartz et al. |
| 6,006,748 A | 12/1999 | Hollis |
| D419,658 S | 1/2000 | Matchett et al. |
| 6,016,804 A | 1/2000 | Gleason et al. |
| D421,298 S | 2/2000 | Kenyon et al. |
| 6,019,101 A | 2/2000 | Cotner et al. |
| 6,029,660 A | 2/2000 | Calluaud et al. |
| 6,029,665 A | 2/2000 | Berthon-Jones |
| 6,039,044 A | 3/2000 | Sullivan |
| D423,096 S | 4/2000 | Kwok |
| 6,044,844 A | 4/2000 | Kwok et al. |
| 6,062,221 A | 5/2000 | Brostrom et al. |
| 6,091,973 A | 7/2000 | Colla et al. |
| D428,987 S | 8/2000 | Kwok |
| 6,098,205 A | 8/2000 | Schwartz et al. |
| 6,112,746 A | 9/2000 | Kwok et al. |
| 6,119,693 A | 9/2000 | Kwok et al. |
| 6,123,071 A | 9/2000 | Berthon-Jones et al. |
| 6,152,137 A | 11/2000 | Schwartz et al. |
| 6,192,886 B1 | 2/2001 | Rudolph |
| D439,326 S | 3/2001 | Hecker et al. |
| 6,196,223 B1 | 3/2001 | Belfer et al. |
| D443,355 S | 6/2001 | Gunaratnam et al. |
| 6,257,237 B1 | 7/2001 | Suzuki |
| 6,341,606 B1 | 1/2002 | Bordewick et al. |
| 6,357,441 B1 | 3/2002 | Kwok et al. |
| 6,374,826 B1 | 4/2002 | Gunaratnam et al. |
| 6,388,640 B1 | 5/2002 | Chigira et al. |
| 6,397,847 B1 | 6/2002 | Scarberry |
| 6,412,487 B1 | 7/2002 | Gunaratnam et al. |
| 6,418,928 B1 | 7/2002 | Bordewick et al. |
| 6,427,694 B1 | 8/2002 | Hecker et al. |
| 6,431,172 B1 | 8/2002 | Bordewick |
| 6,439,230 B1 | 8/2002 | Gunaratnam et al. |
| 6,463,931 B1 | 10/2002 | Kwok et al. |
| 6,467,483 B1 | 10/2002 | Kopacko et al. |
| 6,491,034 B1 | 12/2002 | Gunaratnam |
| D468,823 S | 1/2003 | Smart |
| 6,513,526 B2 | 2/2003 | Kwok et al. |
| 6,520,182 B1 | 2/2003 | Gunaratnam |

| | | |
|---|---|---|
| 6,530,373 B1 | 3/2003 | Patron et al. |
| 6,532,961 B1 | 3/2003 | Kwok |
| 6,557,556 B2 | 5/2003 | Kwok et al. |
| 6,561,190 B1 | 5/2003 | Kwok |
| 6,561,191 B1 | 5/2003 | Kwok |
| 6,581,601 B2 | 6/2003 | Ziaee |
| 6,595,214 B1 | 7/2003 | Hecker et al. |
| 6,615,830 B1 | 9/2003 | Serowski et al. |
| 6,615,832 B1 | 9/2003 | Chen |
| 6,631,718 B1 | 10/2003 | Lovell |
| D484,237 S | 12/2003 | Lang et al. |
| 6,679,261 B2 | 1/2004 | Lithgow |
| 6,691,707 B1 | 2/2004 | Gunaratnam et al. |
| 6,691,708 B2 | 2/2004 | Kwok et al. |
| 6,701,535 B2 | 3/2004 | Dobbie et al. |
| 6,712,072 B1 | 3/2004 | Lang |
| D492,992 S | 7/2004 | Guney et al. |
| D493,521 S | 7/2004 | Guney |
| 6,789,543 B2 | 9/2004 | Cannon |
| 6,805,117 B1 | 10/2004 | Ho et al. |
| 6,823,869 B2 | 11/2004 | Raje et al. |
| 6,851,425 B2 | 2/2005 | Jaffre |
| 6,851,428 B2 | 2/2005 | Dennis |
| 6,860,269 B2 | 3/2005 | Kwok et al. |
| 6,892,729 B2 | 5/2005 | Smith et al. |
| 6,907,882 B2 | 6/2005 | Ging |
| 6,926,004 B2 | 8/2005 | Schumacher |
| 6,968,844 B2 | 11/2005 | Liland et al. |
| 7,000,614 B2 | 2/2006 | Lang et al. |
| 7,007,696 B2 | 3/2006 | Palkon et al. |
| 7,011,090 B2 | 3/2006 | Drew et al. |
| 7,047,972 B2 | 5/2006 | Ging et al. |
| 7,059,326 B2 | 6/2006 | Heidmann et al. |
| 7,069,932 B2 | 7/2006 | Eaton et al. |
| 7,178,525 B2 | 2/2007 | Matula, Jr. et al. |
| 7,185,652 B2 | 3/2007 | Gunaratnam et al. |
| 7,207,335 B2 | 4/2007 | Kwok et al. |
| 7,216,647 B2 | 5/2007 | Lang et al. |
| 7,318,437 B2 | 1/2008 | Gunaratnam et al. |
| 7,320,323 B2 | 1/2008 | Lang et al. |
| 7,353,826 B2 | 4/2008 | Sleeper et al. |
| 7,461,656 B2 | 12/2008 | Gunaratnam et al. |
| 7,487,772 B2 | 2/2009 | Ging et al. |
| 7,503,327 B2 | 3/2009 | Gunaratnam |
| 7,509,958 B2 | 3/2009 | Amarasinghe et al. |
| 7,523,754 B2 | 4/2009 | Lithgow |
| 7,614,400 B2 | 11/2009 | Lithgow et al. |
| 7,621,274 B2 | 11/2009 | Sprinkle et al. |
| 7,654,263 B2 | 2/2010 | Lang et al. |
| 7,665,464 B2 | 2/2010 | Kopacko et al. |
| 7,743,767 B2 | 6/2010 | Ging et al. |
| 7,762,259 B2 | 7/2010 | Gunaratnam |
| 7,775,209 B2 | 8/2010 | Biener et al. |
| 7,819,119 B2 | 10/2010 | Ho |
| 7,841,345 B2 | 11/2010 | Guney et al. |
| 7,856,980 B2 | 12/2010 | Lang et al. |
| 7,856,982 B2 | 12/2010 | Matula, Jr. et al. |
| 7,861,715 B2 | 1/2011 | Jones et al. |
| 7,874,293 B2 | 1/2011 | Gunaratnam et al. |
| 7,878,199 B2 | 2/2011 | Ging et al. |
| 7,900,635 B2 | 3/2011 | Gunaratnam et al. |
| 7,942,148 B2 | 5/2011 | Davidson et al. |
| 7,967,013 B2 | 6/2011 | Ging et al. |
| 7,967,014 B2 | 6/2011 | Heidmann et al. |
| 7,992,559 B2 | 8/2011 | Lang et al. |
| 8,042,538 B2 | 10/2011 | Ging et al. |
| 8,042,546 B2 | 10/2011 | Gunaratnam et al. |
| 8,051,850 B2 | 11/2011 | Kwok et al. |
| 8,136,524 B2 | 3/2012 | Ging et al. |
| 8,186,352 B2 | 5/2012 | Gunaratnam et al. |
| 8,210,180 B2 | 7/2012 | Gunaratnam |
| 8,220,459 B2 | 7/2012 | Davidson et al. |
| 8,297,283 B2 | 10/2012 | Hitchcock et al. |
| 8,397,728 B2 | 3/2013 | D'Souza et al. |
| 2003/0062048 A1 | 4/2003 | Gradon et al. |
| 2003/0089373 A1 | 5/2003 | Gradon et al. |
| 2003/0094177 A1 | 5/2003 | Smith et al. |
| 2003/0196656 A1 | 10/2003 | Moore et al. |
| 2003/0221691 A1 | 12/2003 | Biener et al. |
| 2004/0025883 A1 | 2/2004 | Eaton et al. |
| 2004/0094157 A1 | 5/2004 | Dantanarayana et al. |
| 2004/0112385 A1 | 6/2004 | Drew |
| 2004/0118406 A1 | 6/2004 | Lithgow et al. |
| 2004/0144386 A1 | 7/2004 | Frater et al. |
| 2004/0177850 A1 | 9/2004 | Gradon et al. |
| 2005/0098183 A1 | 5/2005 | Nash et al. |
| 2006/0076017 A1 | 4/2006 | Walker et al. |
| 2006/0081250 A1 | 4/2006 | Bordewick et al. |
| 2006/0118117 A1 | 6/2006 | Berthon-Jones et al. |
| 2006/0201514 A1 | 9/2006 | Jones et al. |
| 2006/0219246 A1 | 10/2006 | Dennis |
| 2006/0254593 A1 | 11/2006 | Chang |
| 2006/0272646 A1 | 12/2006 | Ho et al. |
| 2006/0283461 A1 | 12/2006 | Lubke et al. |
| 2007/0044804 A1 | 3/2007 | Matula, Jr. et al. |
| 2007/0137653 A1 | 6/2007 | Wood |
| 2007/0144525 A1 | 6/2007 | Davidson et al. |
| 2007/0215161 A1 | 9/2007 | Frater et al. |
| 2007/0221226 A1 | 9/2007 | Hansen et al. |
| 2008/0178875 A1 | 7/2008 | Henry |
| 2008/0178886 A1 | 7/2008 | Lieberman et al. |
| 2008/0257354 A1 | 10/2008 | Davidson et al. |
| 2008/0302365 A1 | 12/2008 | Cohen et al. |
| 2008/0314389 A1 | 12/2008 | Thomas et al. |
| 2009/0044808 A1 | 2/2009 | Guney |
| 2009/0050156 A1 | 2/2009 | Ng et al. |
| 2009/0126739 A1 | 5/2009 | Ng et al. |
| 2009/0139527 A1 | 6/2009 | Ng et al. |
| 2009/0223521 A1 | 9/2009 | Howard et al. |
| 2010/0000543 A1 | 1/2010 | Berthon-Jones et al. |
| 2010/0089401 A1 | 4/2010 | Lang et al. |
| 2010/0300447 A1 | 12/2010 | Biener et al. |
| 2010/0319700 A1 | 12/2010 | Ng et al. |
| 2011/0030692 A1 | 2/2011 | Jones et al. |
| 2011/0226254 A1 | 9/2011 | Lang et al. |
| 2011/0259337 A1 | 10/2011 | Hitchcock et al. |
| 2012/0138063 A1 | 6/2012 | Eves et al. |
| 2012/0266886 A1 | 10/2012 | Davidson et al. |
| 2013/0037033 A1 | 2/2013 | Hitchcock et al. |
| 2013/0081628 A1 | 4/2013 | Davidson et al. |
| 2013/0081629 A1 | 4/2013 | Davidson et al. |
| 2013/0081630 A1 | 4/2013 | Davidson et al. |
| 2013/0081631 A1 | 4/2013 | Davidson et al. |
| 2013/0081632 A1 | 4/2013 | Davidson et al. |
| 2013/0086795 A1 | 4/2013 | Davidson et al. |
| 2013/0086796 A1 | 4/2013 | Davidson et al. |
| 2013/0087147 A1 | 4/2013 | Davidson et al. |
| 2013/0087148 A1 | 4/2013 | Davidson et al. |
| 2013/0087149 A1 | 4/2013 | Davidson et al. |
| 2013/0092168 A1 | 4/2013 | Davidson et al. |
| 2013/0092170 A1 | 4/2013 | Davidson et al. |
| 2013/0133658 A1 | 5/2013 | Ng et al. |
| 2013/0133659 A1 | 5/2013 | Ng et al. |
| 2013/0133660 A1 | 5/2013 | Ng et al. |

FOREIGN PATENT DOCUMENTS

| | | |
|---|---|---|
| AU | 95/16178 | 7/1995 |
| AU | 94/59430 | 10/1995 |
| AU | 95/32914 | 2/1996 |
| AU | 97/41018 | 4/1998 |
| AU | 98/89312 | 1/1999 |
| CA | 618807 | 4/1961 |
| CA | 623129 | 7/1961 |
| CA | 1039144 | 9/1978 |
| CN | 2464353 Y | 12/2001 |
| DE | 284 800 | 11/1913 |
| DE | 459 104 | 4/1928 |
| DE | 701 690 | 1/1941 |
| DE | 30 15 279 | 10/1981 |
| DE | 159396 | 3/1983 |
| DE | 33 45 067 | 6/1984 |
| DE | 37 07 952 | 3/1987 |
| DE | 35 37 507 | 4/1987 |
| DE | 35 39 073 | 5/1987 |
| DE | 40 04 157 | 4/1991 |
| DE | 42 12 259 | 1/1993 |
| DE | 43 43 205 | 6/1995 |
| DE | 195 48 380 | 7/1996 |

| | | |
|---|---|---|
| DE | 297 15 718 | 10/1997 |
| DE | 197 35 359 | 1/1998 |
| DE | 297 23 101 | 7/1998 |
| DE | 298 10 846 | 8/1998 |
| DE | 198 17 332 | 1/1999 |
| DE | 198 07 961 | 8/1999 |
| DE | 198 08 105 | 9/1999 |
| DE | 198 40 760 | 3/2000 |
| DE | 200 05 346 | 5/2000 |
| DE | 299 23 141 | 5/2000 |
| DE | 200 17 940 | 2/2001 |
| DE | 199 54 517 | 6/2001 |
| DE | 100 45 183 | 5/2002 |
| EP | 0 054 154 | 6/1982 |
| EP | 0 252 052 | 1/1988 |
| EP | 0 264 772 | 4/1988 |
| EP | 0 386 605 | 9/1990 |
| EP | 0 427 474 | 5/1991 |
| EP | 0 462 701 | 12/1991 |
| EP | 0 549 299 | 6/1993 |
| EP | 0 602 424 | 6/1994 |
| EP | 0 608 684 | 8/1994 |
| EP | 0 697 225 | 2/1996 |
| EP | 0 178 925 A2 | 4/1996 |
| EP | 0 747 078 | 12/1996 |
| EP | 0 821 978 | 2/1998 |
| EP | 1027905 A2 | 8/2000 |
| EP | 1057494 A2 | 12/2000 |
| EP | 1 099 452 | 5/2001 |
| EP | 1 163 923 | 12/2001 |
| EP | 1 205 205 | 5/2002 |
| FR | 780018 | 4/1935 |
| FR | 2 574 657 | 6/1986 |
| FR | 2 658 725 | 8/1991 |
| FR | 2 720 280 | 12/1995 |
| FR | 2 749 176 | 12/1997 |
| GB | 823 887 | 11/1959 |
| GB | 880942 | 10/1961 |
| GB | 1 395 391 | 5/1975 |
| GB | 1 467 828 | 3/1977 |
| GB | 2 145 335 | 3/1985 |
| GB | 2 147 506 | 5/1985 |
| GB | 2 164 569 | 3/1986 |
| GB | 2 186 801 | 8/1987 |
| GB | 2 267 648 | 12/1993 |
| JP | S39-13991 | 7/1964 |
| JP | H09-216240 | 8/1997 |
| JP | H11-000397 | 1/1999 |
| JP | H11-508159 | 7/1999 |
| JP | 2000-279520 | 10/2000 |
| JP | 2000-325481 | 11/2000 |
| JP | 2000-515784 | 11/2000 |
| JP | 2002-028240 | 1/2002 |
| JP | 2002-543943 | 12/2002 |
| JP | 2008/501438 A | 1/2008 |
| WO | WO 80/01044 | 5/1980 |
| WO | WO 82/03548 | 10/1982 |
| WO | WO 86/06969 | 12/1986 |
| WO | WO 87/01950 | 4/1987 |
| WO | WO 91/03277 | 3/1991 |
| WO | WO 92/15353 | 9/1992 |
| WO | WO 92/20395 | 11/1992 |
| WO | WO 93/01854 | 2/1993 |
| WO | WO 93/24169 | 12/1993 |
| WO | WO 94/02190 | 2/1994 |
| WO | WO 94/16759 | 8/1994 |
| WO | WO 94/20051 | 9/1994 |
| WO | WO 95/02428 | 1/1995 |
| WO | WO 96/17643 | 6/1996 |
| WO | WO 96/25983 | 8/1996 |
| WO | WO 96/39206 | 12/1996 |
| WO | WO 97/00092 | 1/1997 |
| WO | WO 97/07847 | 3/1997 |
| WO | WO 97/09090 | 3/1997 |
| WO | WO 97/41911 | 11/1997 |
| WO | WO 98/04310 | 2/1998 |
| WO | WO 98/11930 | 3/1998 |
| WO | WO 98/12965 | 4/1998 |
| WO | WO 98/18514 | 5/1998 |
| WO | WO 98/24499 | 6/1998 |
| WO | WO 98/26829 | 6/1998 |
| WO | WO 98/26830 | 6/1998 |
| WO | WO 98/34665 | 8/1998 |
| WO | WO 98/48878 | 11/1998 |
| WO | WO 99/43375 | 9/1999 |
| WO | WO 99/58181 | 11/1999 |
| WO | WO 99/65554 | 12/1999 |
| WO | 0021600 A1 | 4/2000 |
| WO | WO 00/35525 A1 | 6/2000 |
| WO | WO 00/50121 | 8/2000 |
| WO | WO 00/57942 | 10/2000 |
| WO | WO 00/69521 | 11/2000 |
| WO | WO 00/78381 | 12/2000 |
| WO | WO 00/78384 | 12/2000 |
| WO | WO 01/62326 | 8/2001 |
| WO | WO 01/97892 | 12/2001 |
| WO | WO 01/97893 | 12/2001 |
| WO | WO 02/11804 | 2/2002 |
| WO | WO 02/32491 | 4/2002 |
| WO | 0245784 A1 | 6/2002 |
| WO | WO 03/005931 | 1/2003 |
| WO | WO 03/059427 | 7/2003 |
| WO | WO 2003/082406 | 10/2003 |
| WO | WO 2004/022144 | 3/2004 |
| WO | WO 2004/022145 | 3/2004 |
| WO | WO 2004/022146 | 3/2004 |
| WO | WO 2004/073778 | 9/2004 |
| WO | WO 2004/078228 | 9/2004 |
| WO | WO 2004/096332 | 11/2004 |
| WO | WO 2005/002656 | 1/2005 |
| WO | WO 2005/063326 | 7/2005 |
| WO | WO 2005/063328 | 7/2005 |
| WO | WO 2005/094928 | 10/2005 |
| WO | WO 2005/123166 | 12/2005 |
| WO | WO 2006/000046 | 1/2006 |
| WO | WO 2006/074513 | 7/2006 |
| WO | WO 2006/074514 A1 | 7/2006 |
| WO | WO 2006/074515 | 7/2006 |
| WO | WO 2006/074516 | 7/2006 |
| WO | WO 2006/138416 | 12/2006 |
| WO | WO 2007/045008 | 4/2007 |
| WO | WO 2007/048174 | 5/2007 |
| WO | WO 2007/143792 A1 | 12/2007 |
| WO | WO 2009/026627 | 3/2009 |
| WO | WO 2009/052560 | 4/2009 |
| WO | WO 2009/062265 | 5/2009 |
| WO | WO 2009/108995 | 9/2009 |
| WO | WO 2010/066004 | 6/2010 |
| WO | WO 2011/060479 A1 | 5/2011 |
| WO | WO 2013/057647 A1 | 4/2013 |
| WO | WO 2013/061260 A1 | 5/2013 |

OTHER PUBLICATIONS

Notification of the Second Office Action mailed Nov. 5, 2012 in Chinese Application No. 201010517066.X, with English Translation (16 pages).

Notice of Reasons for Rejection and English Translation for corresponding Japanese Application No. 2010-268127, mailed Jul. 10, 2012, 8 pages.

Photographs of Weinmann Mask, acquired prior to 1998 (7 pages).

Chinese Office Action and English Translation for corresponding Chinese Application No. 201010517066.X, issued Nov. 10, 2011, 19 pages.

Australia Appln. No. 2010251884—Examination Report, dated Jul. 27, 2012.

Chinese Appln. No. 200910223650.1—Office Action (w/English translation), dated Mar. 29, 2012.

European Appln. No. EP 02714190.2—Search Report, dated Jul. 11, 2006.

European Appln. No. EP 04802114.1—Supplementary Search Report, dated Apr. 27, 2009.

European Appln. No. EP 09178736.6—Search Report, dated May 6, 2010.

European Appln. No. EP 10181516.5—Search Report, dated Jun. 13, 2012.

European Appln. No. EP 10182015.7—Search Report, dated Jun. 15, 2012.
German Patent No. 101 51 984—Decision from Opposition hearing by Weinmann (w/English translation), dated Dec. 6, 2007.
Japanese Appln. No. S52-164619—English translation of Figure 1, Dec. 1977.
Japanese Appln. No. 2003-537718—Office Action (w/English translation), dated Oct. 7, 2008.
Japanese Appln. No. 2003-559587—Office Action (w/English translation), dated Mar. 17, 2009.
Japanese Appln. No. 2005-004072—Office Action (w/English translation), dated Sep. 24, 2009.
Japanese Appln. No. 2006-545843—Notice of Reasons for Rejection (w/English translation), dated Jun. 7, 2011.
Mask 1 Photographs, Respironics Inc., Reusable Full Mask (small) Part #452033 Lot #951108, before applicants' filing date.
Mask 2 Photographs, Puritan-Bennett, Adam Curcuit, Shell Part #231700, Swivel Part #616329-00, Pillows (medium) Part #616324, before applicants' filing date.
Mask 3 Photographs, DeVilbiss Healthcare Inc., Devilbiss Seal-Ring and CPAP Mask Kit (medium), Part #73510-669, before applicants' filing date.
Mask 4 Photographs, Respironics Inc., Monarch Mini Mask with Pressure Port, Part #572004, Monarch Headgear, Part #572011, before applicants' filing date.
Mask 5 Photographs, Healthdyne Technologies, Nasal CPAP Mask (medium narrow), Part #702510, before applicants' filing date.
Mask 6 Photographs, Healthdyne Technologies, Soft Series Nasal CPAP Mask, Part #702020, before applicants' filing date.
Mask 7 Photographs, DeVilbiss Healthcare Inc., Small Mask and Seal Rings, Part #73510-668, before applicants' filing date.
Mask 8 Photographs, Respironics Inc., Reusable Contour Mask (medium), Part #302180, before applicants' filing date.
Mask 9 Photographs, Healthdyne Technologies, Healthdyne Large Headgear, before applicants' filing date.
Mask 10 Photographs, Respironics Inc., Soft Cap (medium), Part #302142, before applicants' filing date.
Mask 11 Photographs, Weinmann: Hamburg, Nasalmaskensystem mit Schalldämpfer (medium), Part #WN 23105, before applicants' filing date.
Mask 12 Photographs, Life Care, before applicants' filing date.
Mask 13 Photographs, Healthdyne Technologies, before applicants' filing date.
Mark 14 Photographs, King System, before applicants' filing date.
Mask 15 Photographs, Respironics Inc., Pediatric Mask, before applicants' filing date.
Mask 16 Photographs, Hans Rudolph Inc., Hans Rudolph Silicone Rubber Face Mask/8900, before applicants' filing date.
New Zealand Appln. No. 567375—Examination Report, dated Nov. 17, 2009.
New Zealand Appln. No. 597689—Examination Report, dated Jan. 25, 2012.
PCT/AU2004/001760—International Search Report, dated Feb. 3, 2005.
PCT/AU2004/001760—International Preliminary Report on Patentability, dated Jul. 3, 2006.
PCT/AU2004/001813—International Search Report, dated Mar. 7, 2005.
PCT/AU2004/001813—International Preliminary Report on Patentability, dated Jul. 3, 2006.
PCT/AU2006/001570—International Search Report, dated Jan. 8, 2007.
PCT/AU2009/000241—International Search Report, dated May 18, 2009.
PCT/AU2009/001102—International Search Report, dated Dec. 11, 2009.
PCT/AU2010/000657—International Search Report, dated Sep. 9, 2010.
Product Brochure for ResMed "Sullivan® Mirage™—The Mirage is Real. A Perfect Fit-First Time," © 1997 ResMed Limited, 4 pages.
Product Brochure for ResMed "Sullivan® Mirage™—The Mirage is Real. A Perfect Fit-First Time," ©1998 ResMed Limited, 4 pages.
ResMed Ltd., "Improving patient compliance with the ResMed Range of Mask Systems the Ultimate Interface for CPAP treatment," before applicants' filing date, 4 pages.
The ResMed Range of Mask Systems, product brochure, Nov. 1995, 4 pages.
"Somnomask" brochure, 1999 along with various invoices relating to the "Somnomask".
Somnotron CPAP-Great WM 2300 Instruction Manual, Weinmann Hamburg, 1991, 11 pages.
U.S. Appl. No. 12/083,779—Office Action, dated Feb. 17, 2012.
U.S. Appl. No. 12/083,779—Office Action, dated Sep. 28, 2012.
Extended European Search Report mailed Oct. 18, 2012 in European Appln. No. 12165749.8 (8 pages).
Extended European Search Report mailed Oct. 16, 2012 in European Appln. No. 12165751.4 (7 pages).
International Search Report of PCT/AU2004/000563, mailed Jun. 23, 2004.
Japanese Office Action and English translation for copending Japanese Application No. 2006-504029, mailed Nov. 10, 2009, 7 pages.
New Zealand Examination Report for copending New Zealand Application No. 564877, mailed Dec. 2, 2009, 2 pages.
Supplementary European Search Report for copending European Application No. EP 04730413, mailed Sep. 29, 2009, 3 pages.
Notice of Reasons for Rejection mailed Apr. 2, 2013 in Japanese Application No. 2010-268127, with English translation (4 pages).
D'Souza et al., U.S. Appl. No. 13/834,189, filed Mar. 15, 2013, for "Cushion to Frame Assembly Mechanism," including Preliminary Amendment.
Ng et al., U.S. Appl. No. 13/870,678, filed Apr. 25, 2013, for "Interchangeable Mask Assembly," including Preliminary Amendment.

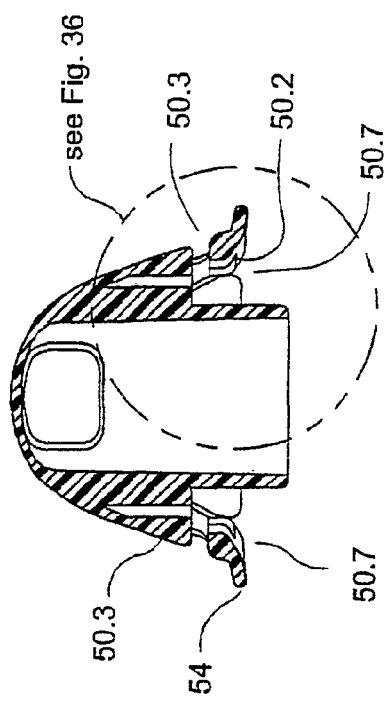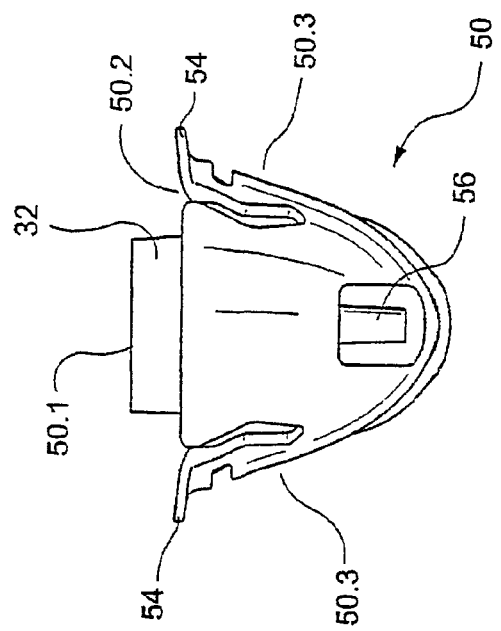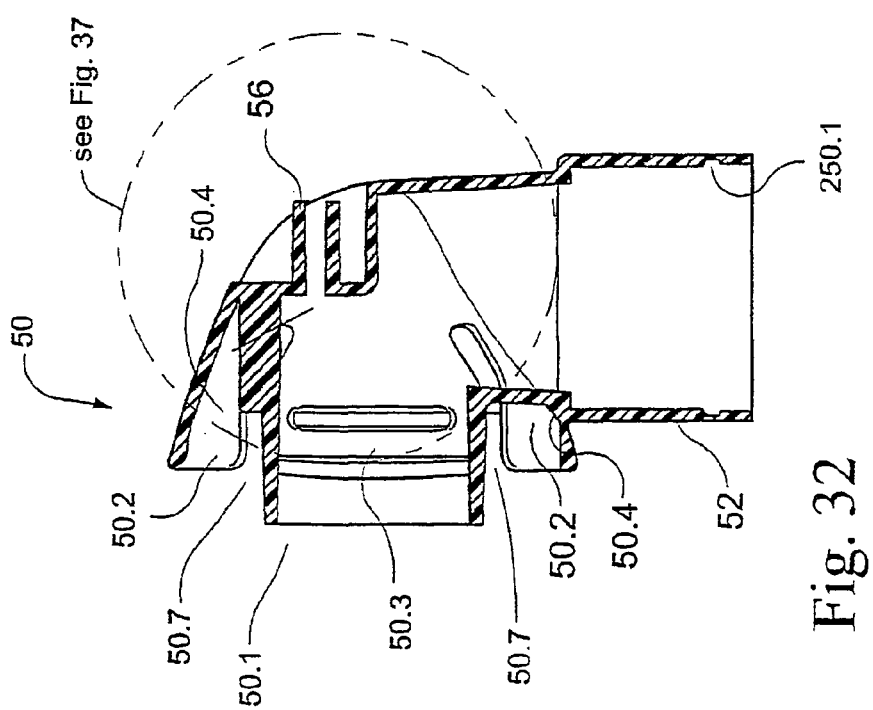

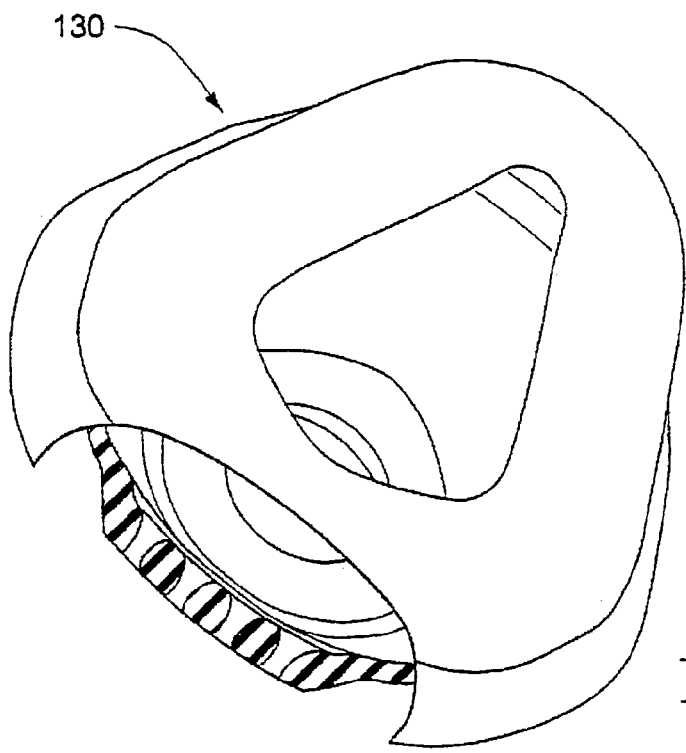
Fig. 53
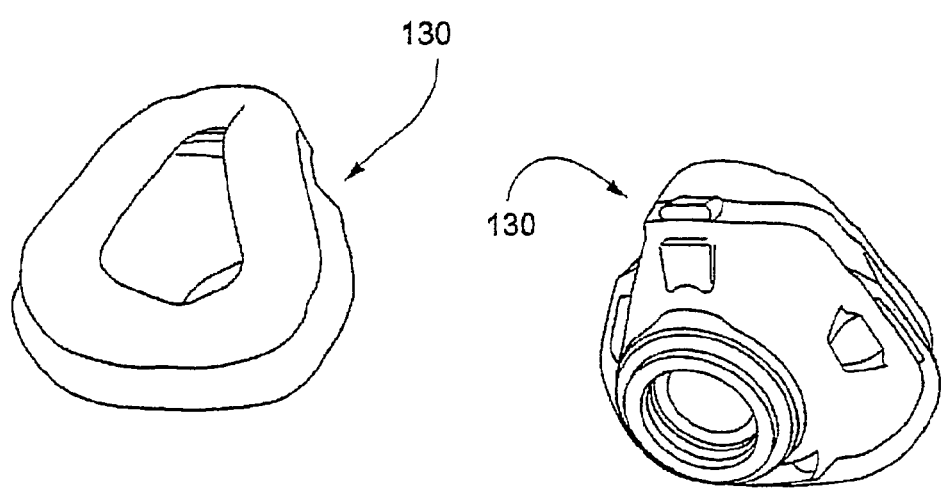
Fig. 54
Fig. 55

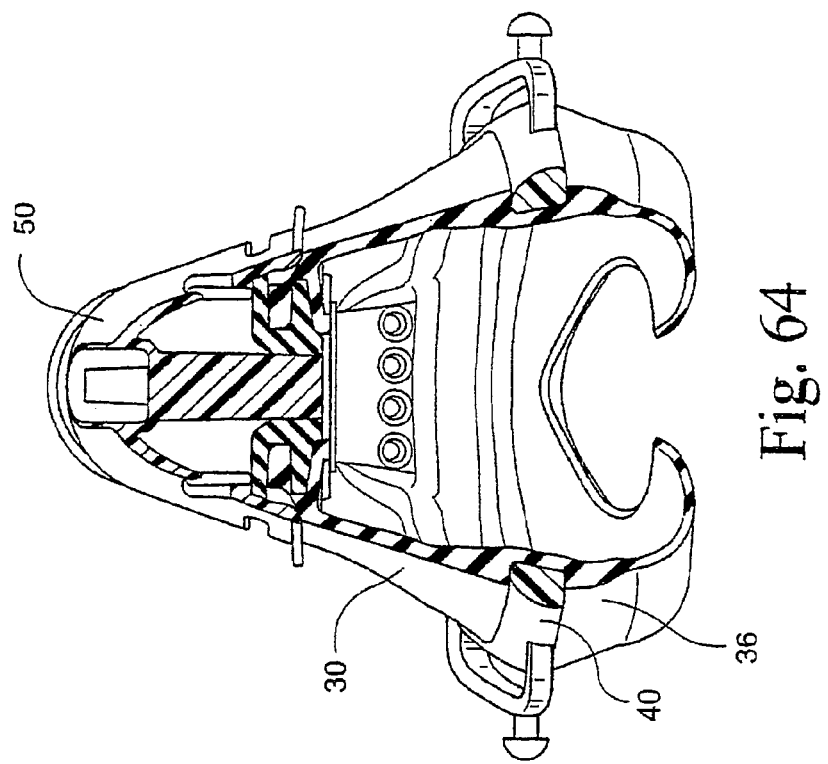
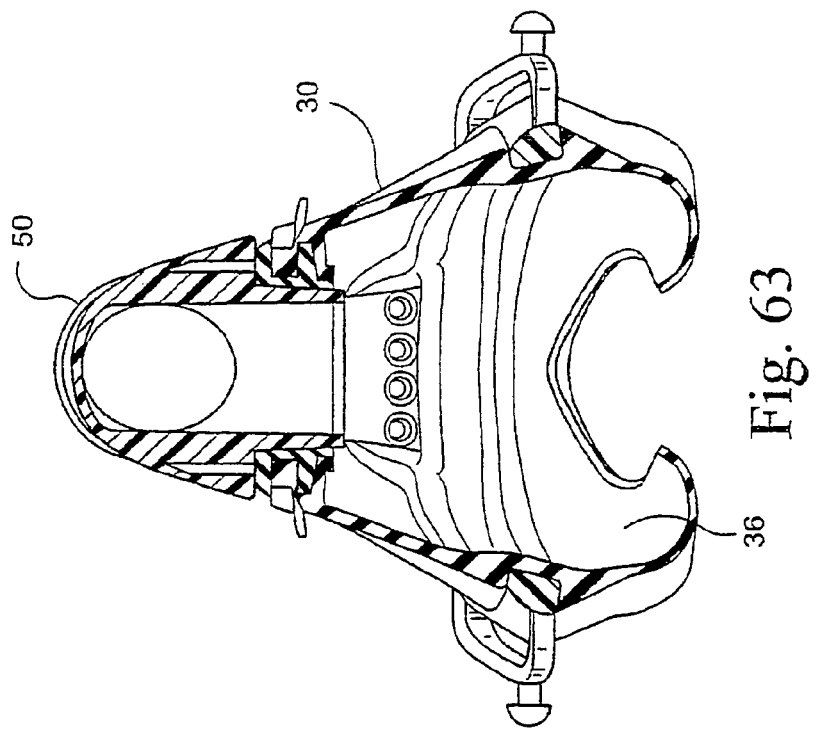

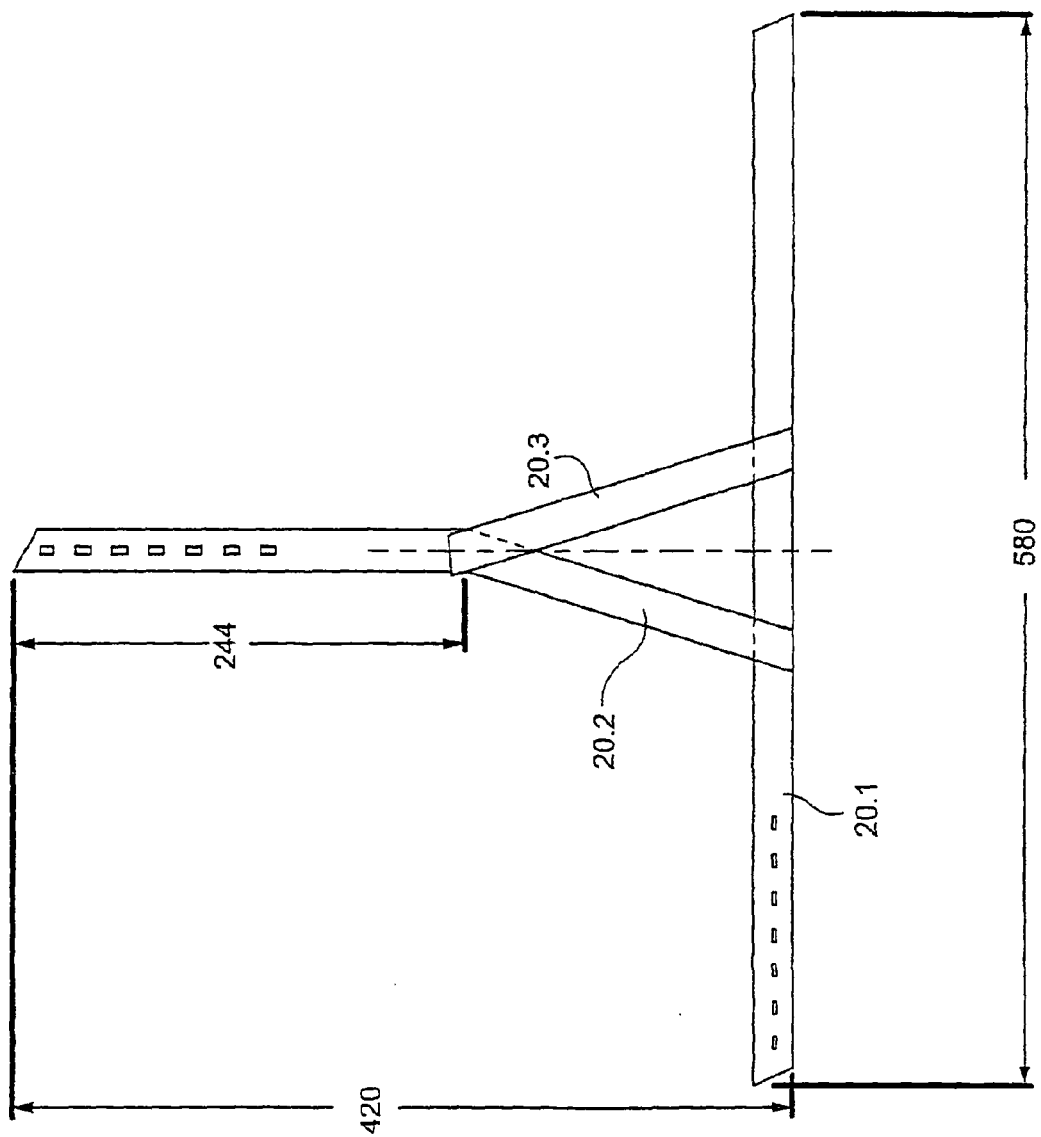

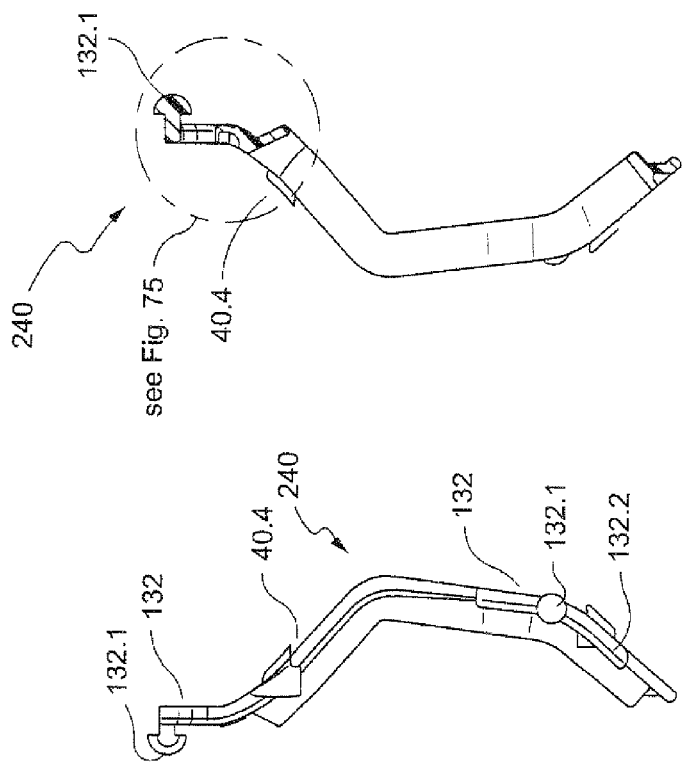
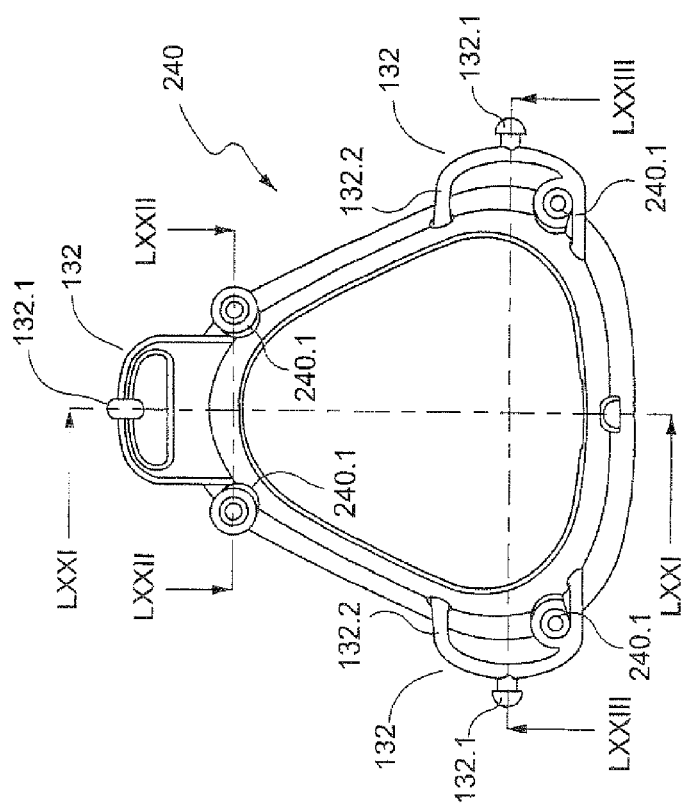

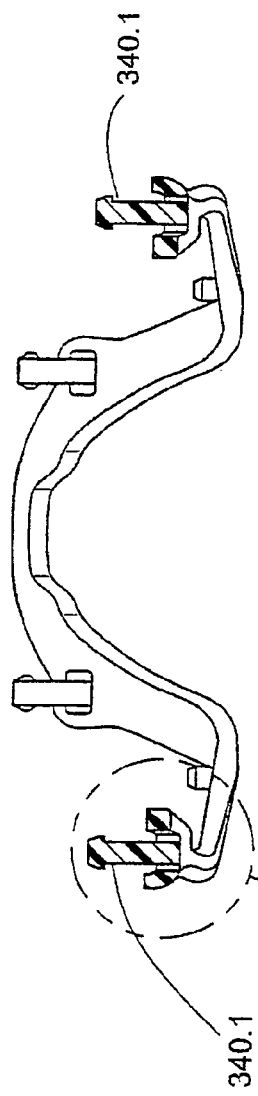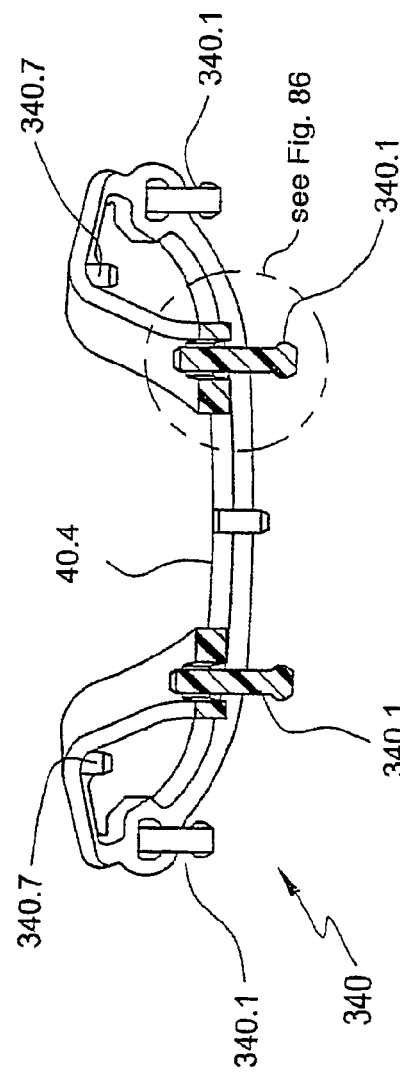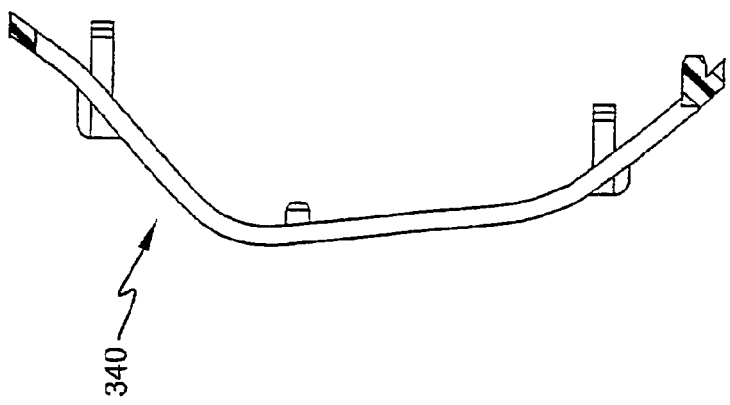

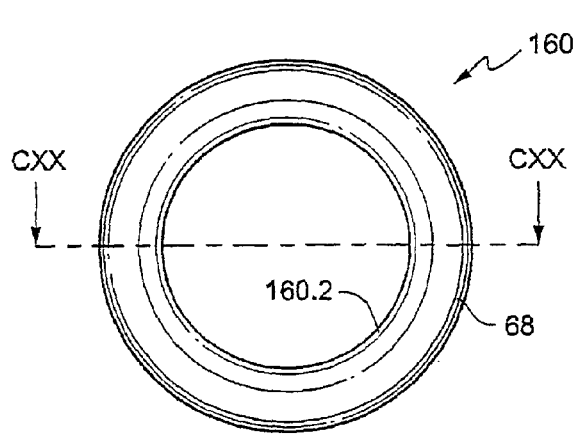
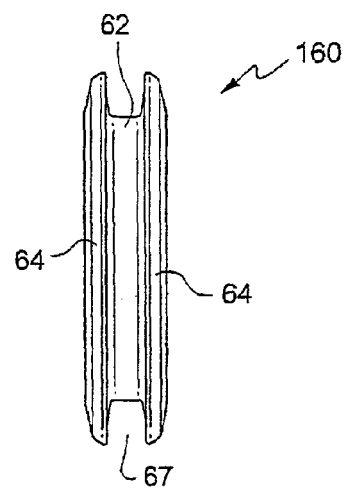
Fig. 118　　　Fig. 119
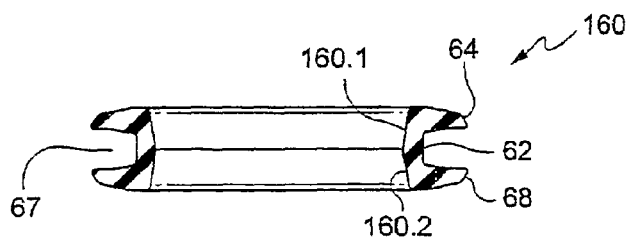
Fig. 120
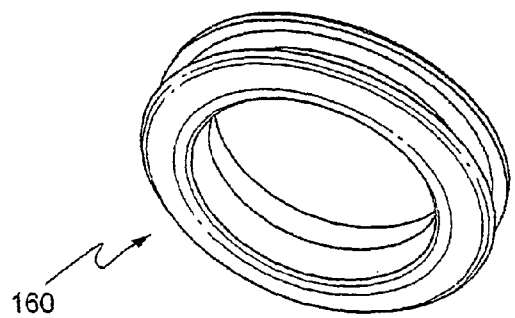
Fig. 121

MASK SYSTEM

CROSS REFERENCE TO RELATED APPLICATIONS

This is a divisional of U.S. application Ser. No. 10/555,301, filed Nov. 2, 2005, now pending, which is U.S. national phase of international application PCT/AU2004/000563, filed Apr. 30, 2004, which designated the U.S. and claims priority of AU 2003902098, filed May 2, 2003, and AU 2004901648, filed Mar. 26, 2004, each incorporated herein by reference in its entirety.

FIELD OF THE INVENTION

The invention relates to a mask system for use with positive pressure ventilation of sleep disordered breathing. In particular, the invention relates to a low cost mask system.

BACKGROUND

Obstructive Sleep Apnea (OSA) is a condition characterised by repetitive obstruction of the upper airway often resulting in oxygen desaturation and arousals from sleep. The classic daytime manifestation is excessive sleepiness but other symptoms such as unrefreshing sleep, poor concentration and fatigue are commonly reported (Sleep-Related Breathing Disorders in Adults-AASM Task Force, *Sleep* 22, 1999)

The use of nasal continuous positive airway pressure (CPAP) to treat OSA was taught by Sullivan in U.S. Pat. No. 4,944,310. Other developments are taught in U.S. Pat. Nos. 5,704,345; 6,029,665 and 6,363,933.

Nasal CPAP systems typically comprise a flow generator, air tubing, and a patient interface (for example, a nasal mask). The flow generator provides a supply of air at positive pressure.

A variety of mask systems are known for use in treating sleep disordered breathing (SDB), such as the BUBBLE® mask, MIRAGE®, ULTRA MIRAGE®, and MIRAGE VISTA™ masks, all manufactured by ResMed Limited.

Another known mask is the Weinmann nasal mask.

A mask system typically comprises headgear and a mask assembly. The headgear is used to hold and position the mask on the face of a patient. The mask assembly typically comprises at least a rigid shell and a soft face-contacting cushion. Some mask assemblies also include elbows, vents, headgear clips, forehead supports.

A number of cushions have been patented, for example see U.S. Pat. Nos. 6,112,746; 6,357,441; 6,513,526; as have forehead supports (See U.S. Pat. Nos. 6,119,693; 6,463,931; 6,520,182; 6,532,961), headgear connectors (U.S. Pat. No. 6,374,826), mask ports (U.S. Pat. No. 6,439,230), and cushion clips (U.S. Pat. No. 6,412,487). For example, U.S. Pat. No. 6,513,526 discloses both nasal and full face cushions. The contents of all these patents are hereby incorporated by cross-reference.

Another known mask assembly the PAPILLION™ mask, manufactured by MAP, Germany is shown in Austrian Design Registrations #50770 and #50771 (and U.S. Design Pat. D484,237 and Australian Design Registration Application 2153/2002).

Since mask systems for treating sleep disordered breathing have to be worn for several hours every night while a patient sleeps, designers strive to make them comfortable. In particular, they strive to attempt to eliminate the mask system being a source of pressure sores on a patient's face.

A problem which can occur in prior art mask systems is that there can be drag forces from the tube which when transferred through the elbow can disrupt the seal of the cushion on the face.

One solution to this problem is found in U.S. Pat. No. 6,039,044. It is an aspect of the invention to provide at least an alternative solution to this problem.

A difficulty with some prior art mask assemblies is that those which achieve a clinically effective seal while being comfortable to wear each night at home can be expensive to manufacture. Headgear can represent a significant proportion of the cost of manufacturing a mask system. The manufacturing costs are passed onto customers which leads to a more expensive mask assembly for patients. This may in turn mean that fewer patients can afford treatment. This may also mean that there can be a tendency for clinics and hospitals to reuse masks among numerous patients. Unless thorough hygiene systems are put in place to manage cross-infection it is not advised that a mask be re-used by different patients. In general, particularly in hospitals with the advent of respiratory diseases such as SARS, it is desirable to have a mask system which is cheap enough to be disposable.

It is a further aspect of the invention to provide a low cost mask assembly for treating sleep disordered breathing.

It is a further aspect of the invention to provide a disposable mask assembly for treating sleep disordered breathing.

SUMMARY OF THE INVENTION

Throughout this specification and claims, a combination shell and cushion will hereinafter be referred to as a "shell/cushion". Whilst this is done for convenience, where ever the expression "shell/cushion" appears it should be read as meaning the combined shell and cushion.

In accordance with a first aspect of the invention, there is provided a comfortable low cost mask system comprising headgear, a combination shell/cushion, a frame, elbow and retaining ring.

In accordance with another aspect of the invention, there is provided a low cost headgear.

In accordance with another aspect of the invention, there is provided a comfortable shell/cushion which has a reduced tendency to cause pressure points on a patient's face.

In one embodiment, a mask system for treating sleep disordered breathing comprises headgear, a shell/cushion including a channel adjacent a front aperture, a frame, an elbow including at least one undercut on a proximal end and a retaining ring including a rear flange adapted to be retainably insertable in the channel of the shell/cushion and a front flange adapted to retainably engage with the at least one undercut of the elbow.

There can be a thin walled section adjacent the channel of the shell/cushion which is adapted to tear upon removal of the elbow.

The elbow construction can help prevent separation of the aperture from the retaining ring during normal use.

The elbow when separate from the mask can have a cylindrical outlet.

The shell/cushion can include an annular flange which when assembled with the elbow or said connection piece engages a rim of said outlet to thereby suitably seal the outlet to said flange.

In another embodiment, a mask system for treating sleep disordered breathing comprises headgear, a frame, and shell/cushion including a frame-receiving channel defined by a front flange and a rear flange, the front flange extending 75% to 100% of the way around the perimeter of the shell/cushion, wherein the frame is adapted to be removably insertable in the frame-receiving channel of the shell/cushion.

This mask system can include at least a nasal bridge region of the shell/cushion adapted to contact the nasal bridge region of a patient. The rear flange of the nasal bridge region can be from 1 mm to 3 mm thick. The rear flange can be approximately 2 mm thick.

In still another embodiment, a connection piece for connecting a mask to a conduit which can carry an air flow to said mask is provided. The connection piece includes an inlet and an outlet and a passage wall to carry the air flow therebetween, the connection piece including, in the vicinity of said outlet between said outlet and said inlet, a vent wall extending away from the passage wall, the vent wall including at least one aperture therethrough.

The connection piece can be formed integrally with the mask. Alternatively the connection piece can be formed separately of the mask and can be joined or attached thereto.

The piece can be formed integrally with the conduit. Alternatively the connection piece can be formed separate from the conduit and can be joined or attached thereto.

The connection piece can be formed so that the outlet lies at any appropriate angle to the inlet. Preferably said outlet lies at an angle to the inlet which angle is in the range of 90° to 180°. The connection piece can be a 90° elbow.

The connection piece can include attachment structure to attach the connection piece to the mask. The attachment structure can include at least one snap-in undercut to engage a mating.

The attachment structure can releasably attach the connection piece to the mask.

The attachment structure can include moveable portions on which said snap-in undercuts are formed, the moveable portions allowing said undercuts to disengage the flange.

The attachment structure can allow rotation of said connection piece relative to said mask.

The connection piece can include a Luer port through the passage wall, which can be on a side and/or the front of said connection piece.

The vent wall can lay at an oblique angle to the air flow. The angle is preferably in the range of 25° to 155°.

The connection piece can include on its external surface a recess having wall portions extending away from an external side of said vent wall. The wall portions can diverge in a direction away from said vent wall.

In yet another embodiment, a mask for treating sleep disordered breathing includes a shell/cushion with an inner and outer surface, a flange extending away from the outer surface and surrounding the shell/cushion, the mask having an exoskeletal frame having a shape which substantially matches the contours of the flange so that it can be positioned adjacent the flange when the shell/cushion is in a shape suitable for use by a patient, and structure to hold said flange to the frame.

The structure to hold the flange to the frame can include one or more apertures through the flange.

Rivets or other fixers can pass through said apertures to hold the flange adjacent the frame.

The frame can be attached to headgear to position the mask onto a patient's head.

The frame can include connection members connected to the frame for cooperating therewith to sandwich the flange between said connection members and the frame. The connection members can be hinged to the frame, or connected to the frame by a flexible member.

A second frame of a shape which substantially matches the contours of the flange can be present, whereby said flange is sandwiched between the first frame and the second frame.

The second frame, the flange and the first ring member can be held together by rivets and/or fixers, etc.

The second frame can include rivets extending therefrom, which can pass through the flange and the first frame. Alternatively the first frame can include rivets extending therefrom, which can pass through the flange and the second frame. Another alternative is for the flange to include a first set of rivets extending in a forward direction and a second set of rivets extending in a rearward direction, the first set of rivets being received in apertures through the first frame, the second set of rivets being received in apertures through the second frame.

The rivets can be deformable at their free end, or the aperture into which they protrude can be deformable.

The rivets can include an undercut so that the undercut can pass through the apertures to hold components together.

Another embodiment of the invention provides a mask system including head gear and mask as described above. This mask system can include a connection piece as described above.

These another aspects will be described in or apparent from the following detailed description of preferred embodiments.

BRIEF DESCRIPTION OF FIGURES

Embodiments of the present invention will now be described by way of example only, with reference to the accompanying Figures, in which:

FIG. 32 illustrates a cross section through the line XXXII-XXXII of the elbow of FIG. 30;

FIG. 33 illustrates a cross section through the line XXXIII-XXXIII of the elbow of FIG. 30;

FIG. 34 illustrates a plan view of the elbow of FIG. 30;

FIG. 53 illustrates a cross section through line LIII-LIII of the shell/cushion of FIG. 48;

FIG. 54 illustrates a lower rear perspective view of the shell/cushion of FIG. 47;

FIG. 55 illustrates an upper front perspective view of the shell/cushion of FIG. 47;

FIG. 63 illustrates a cross section through the line LXIII-LXIII of the mask assembly of FIG. 62;

FIG. 64 illustrates a cross section through the line LXIV-LXIV of the mask assembly of FIG. 62;

FIG. 67 shows headgear in accordance with a disposable embodiment of the invention;

FIG. 69 illustrates a front elevation of a frame;

FIG. 70 illustrates a right side elevation of the frame of FIG. 69;

FIG. 71 illustrates a cross section through the line LXXI-LXXI of the frame of FIG. 69;

FIG. 81 illustrates a cross section through the line LXXXI-LXXXI of the frame of FIG. 79;

FIG. 82 illustrates a cross section through the line LXXXII-LXXXII of the frame of FIG. 79;

FIG. 83 illustrates a cross section through the line LXXXIII-LXXXIII of the frame of FIG. 79;

FIG. 115 illustrates in detail a portion of the cross section of FIG. 110;

FIG. 116 illustrates an upper front perspective of the shell/cushion of FIG. 109;

FIG. 117 illustrates a lower rear perspective of the shell/cushion of FIG. 109;

FIG. 118 illustrates a front elevation of another retaining ring for use with the shell/cushion of FIG. 109;

FIG. 119 illustrates a side view of the ring of FIG. 118;

FIG. 120 illustrates a diametrical cross section through the ring of FIG. 118;

FIG. 121 illustrates a perspective view of the ring of FIG. 118;

FIG. 122 illustrates an exploded perspective view of the a mask assembly comprising the components of the frame of FIG. 69, the clip of FIG. 79, the elbow of FIG. 99 and the shell/cushion of FIG. 109;

FIG. 123 illustrates the mask assembly of FIG. 122, with all components shown in assembled condition, with some components being shown in cross section;

FIG. 124 illustrates a detailed cross section through a rivet, shell/cushion aperture and front frame aperture of FIG. 122, which are located at the bottom of the mask assembly;

FIG. 125 illustrates a cross section through the retaining ring of the mask assembly of FIGS. 122 and 123, with the left half showing one arrangement and the right half showing another arrangement to seal the shell/cushion and the elbow; and FIG. 126 illustrates a s side view of a such as that illustrated in FIGS. 69 to 78, wherein two rivet systems are formed integrally therewith.

DETAILED DESCRIPTION OF PREFERRED EMBODIMENTS

§1 Introduction

In various forms the embodiments provides a comfortable low cost mask system which has few components and for example, has a single walled cushion. In a preferred form it does not include a forehead support, nor headgear clips, but it will be readily understood that these can be included if desired.

The embodiments include a mask system which provides a patient interface having a range of interchangeable sub-components as part of a device for delivering a supply of air at positive pressure to the airways of a patient in the treatment of sleep disordered breathing. The mask system includes headgear and a mask assembly (see FIG. 1).

Figure 1:
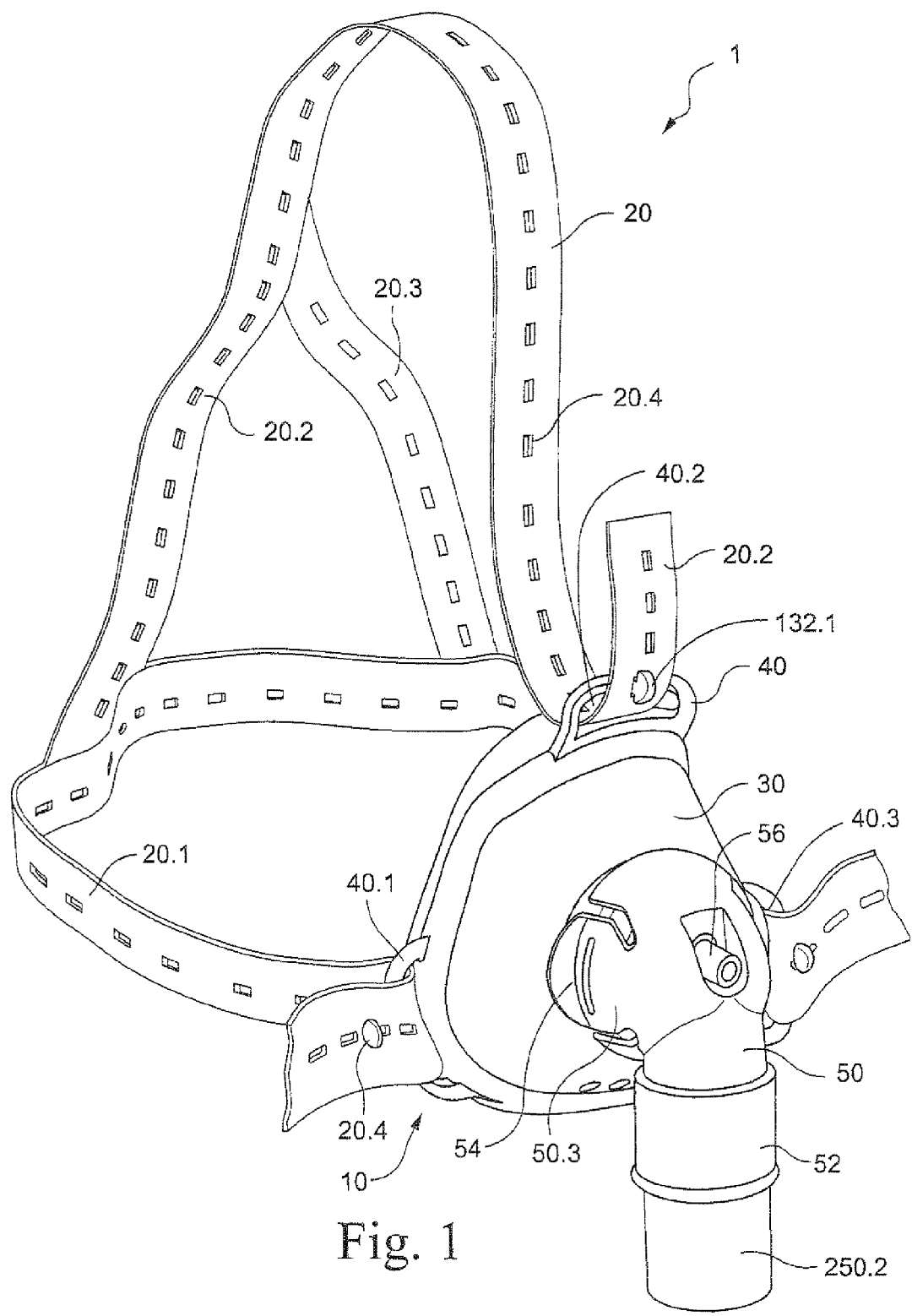
FIG. 1 shows a perspective view of a mask system according to an embodiment of the present invention.
Figure 2:
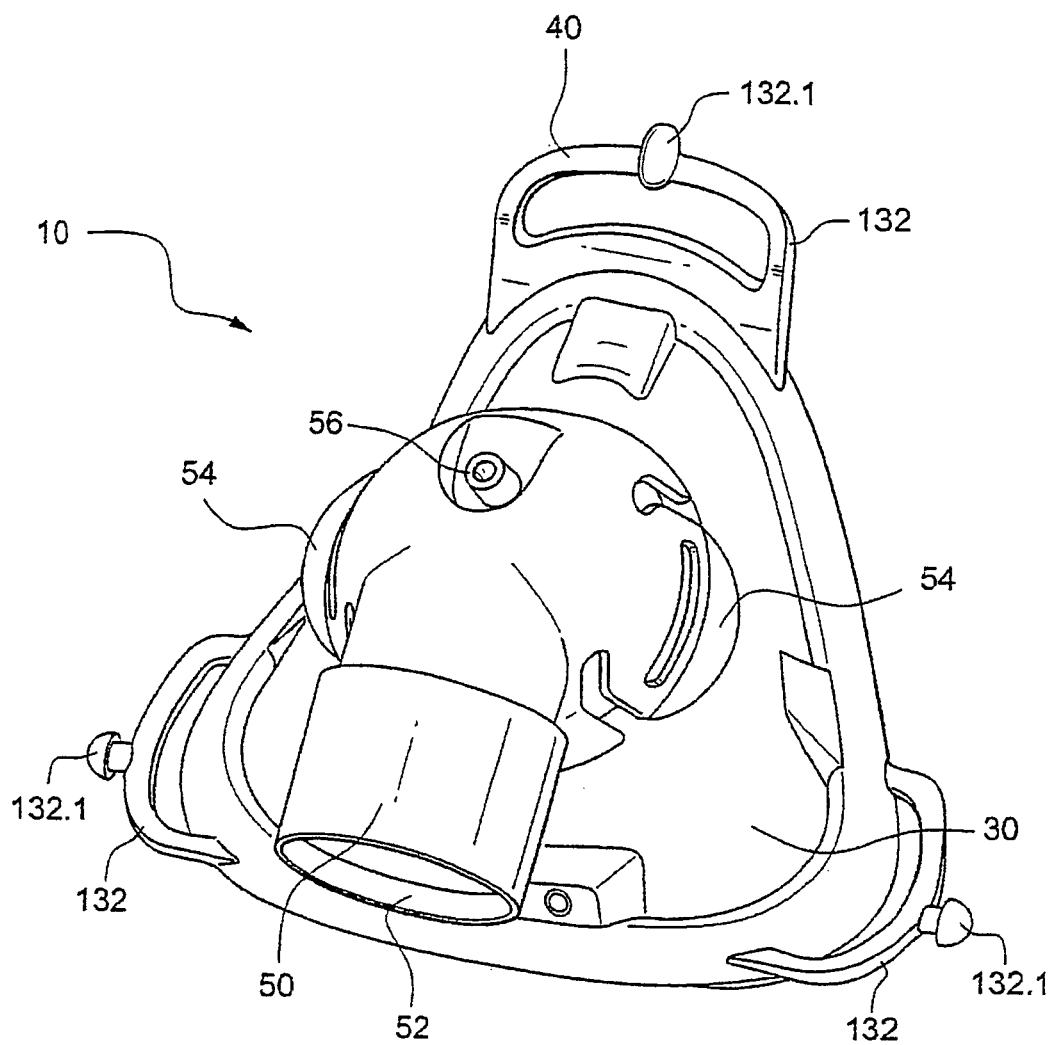
FIG. 2 shows a front perspective view of a mask assembly similar to that used in the system of FIG. 1, but having a different shell/cushion.
Figure 2A:
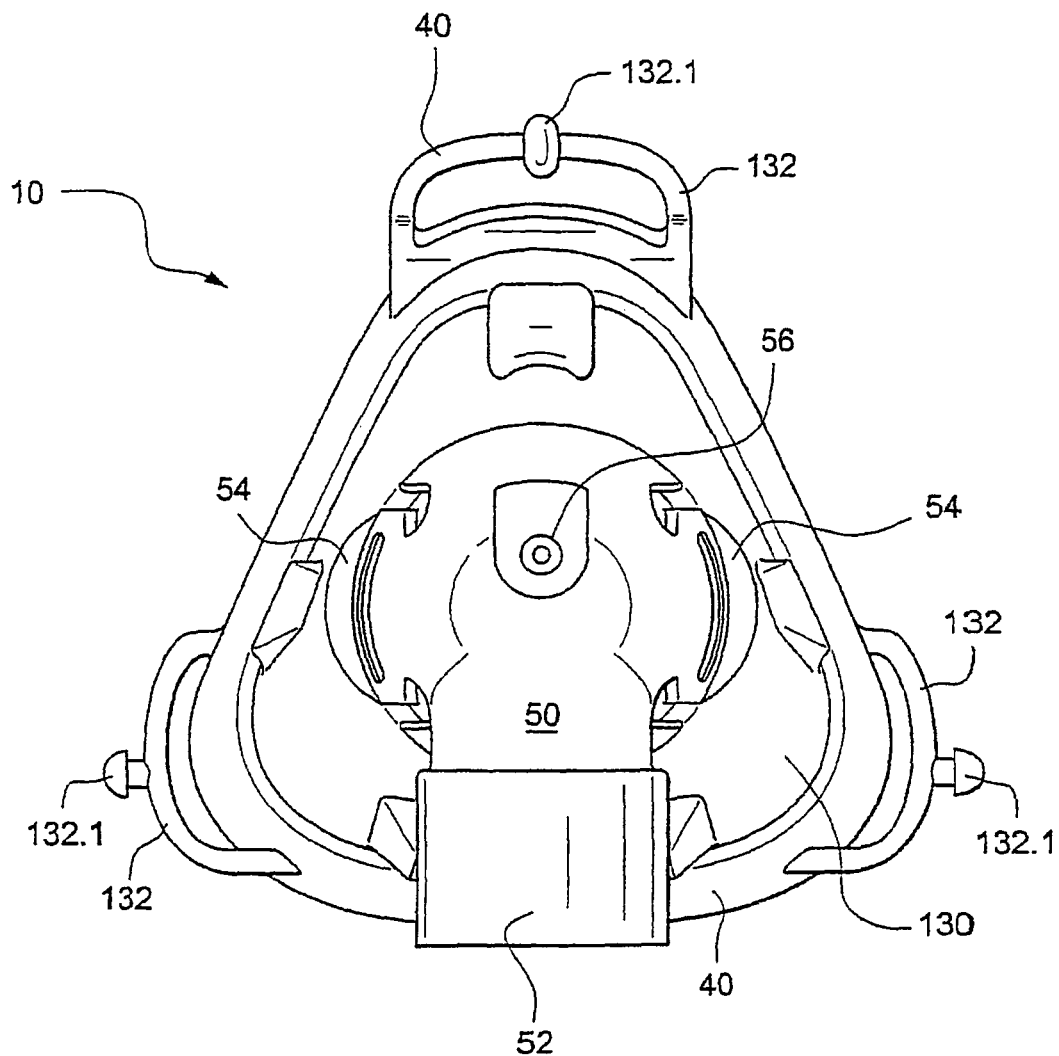
FIG. 2A shows a front view of the mask assembly of FIG. 2.
Figure 7:
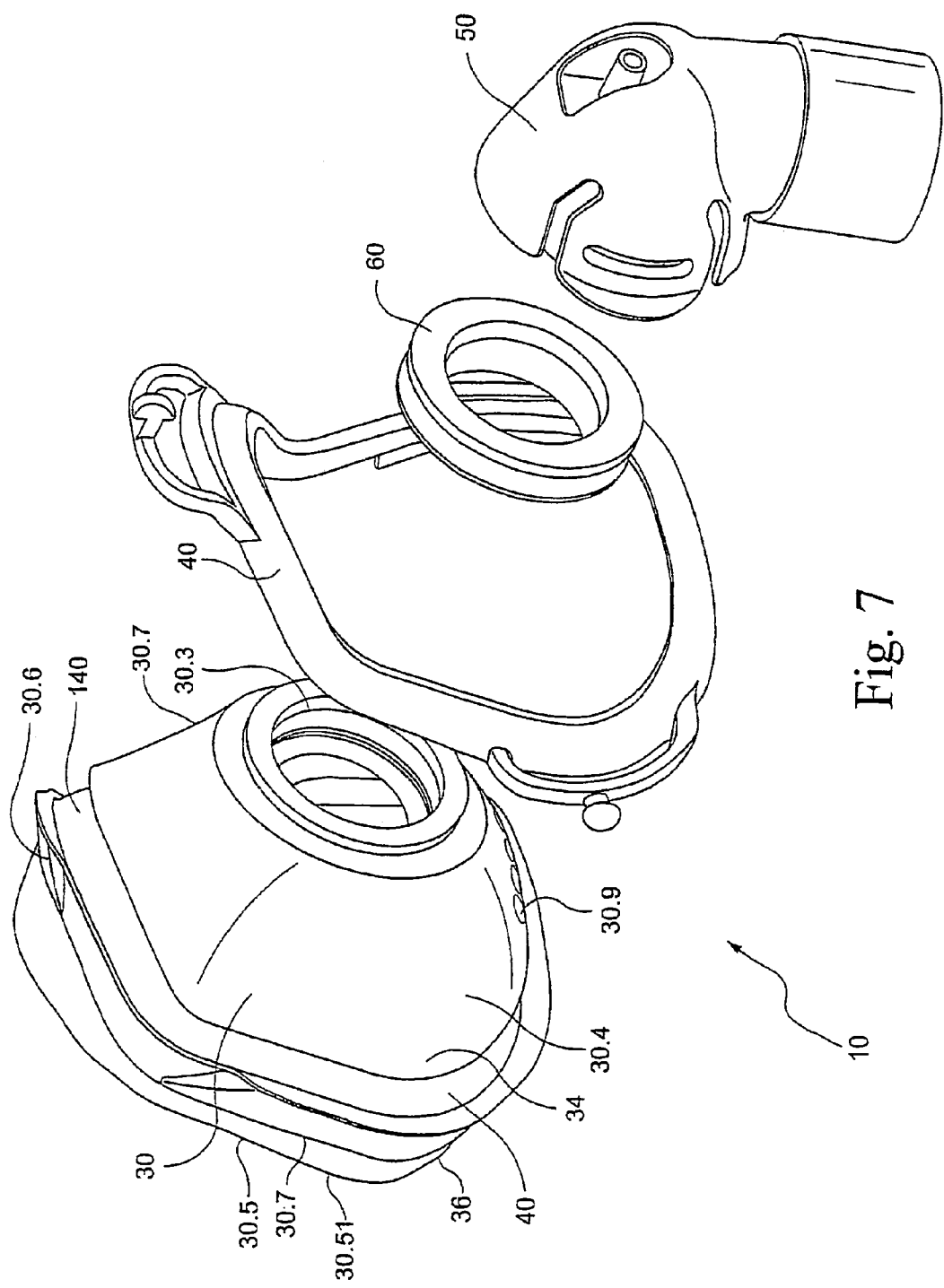
FIG. 7 shows an exploded view of the mask assembly of FIG. 2.
Figure 10:
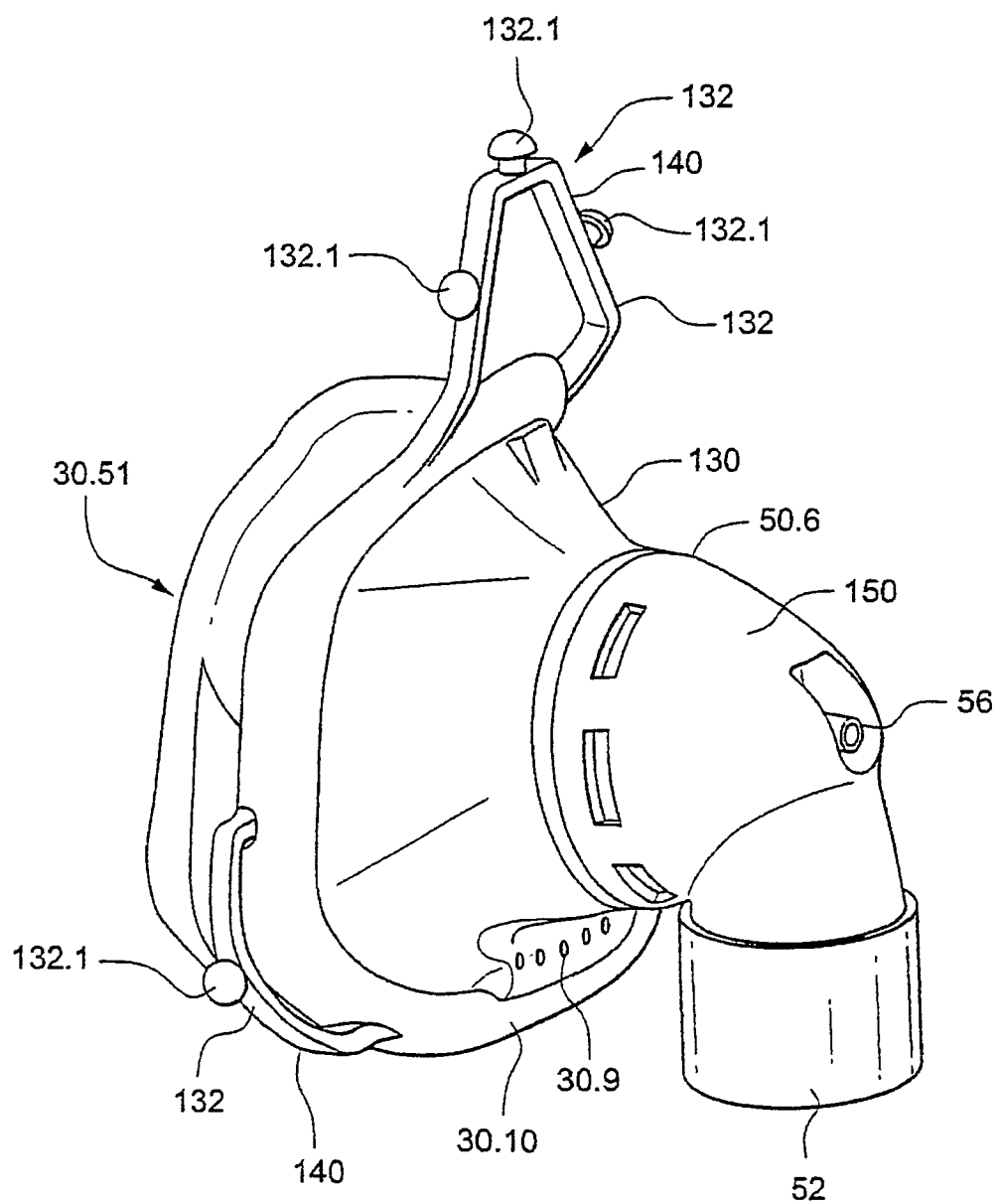
FIG. 10 shows a front perspective view of another mask assembly having the same shell/cushion used in FIG. 2, with a different frame.
Figure 11:
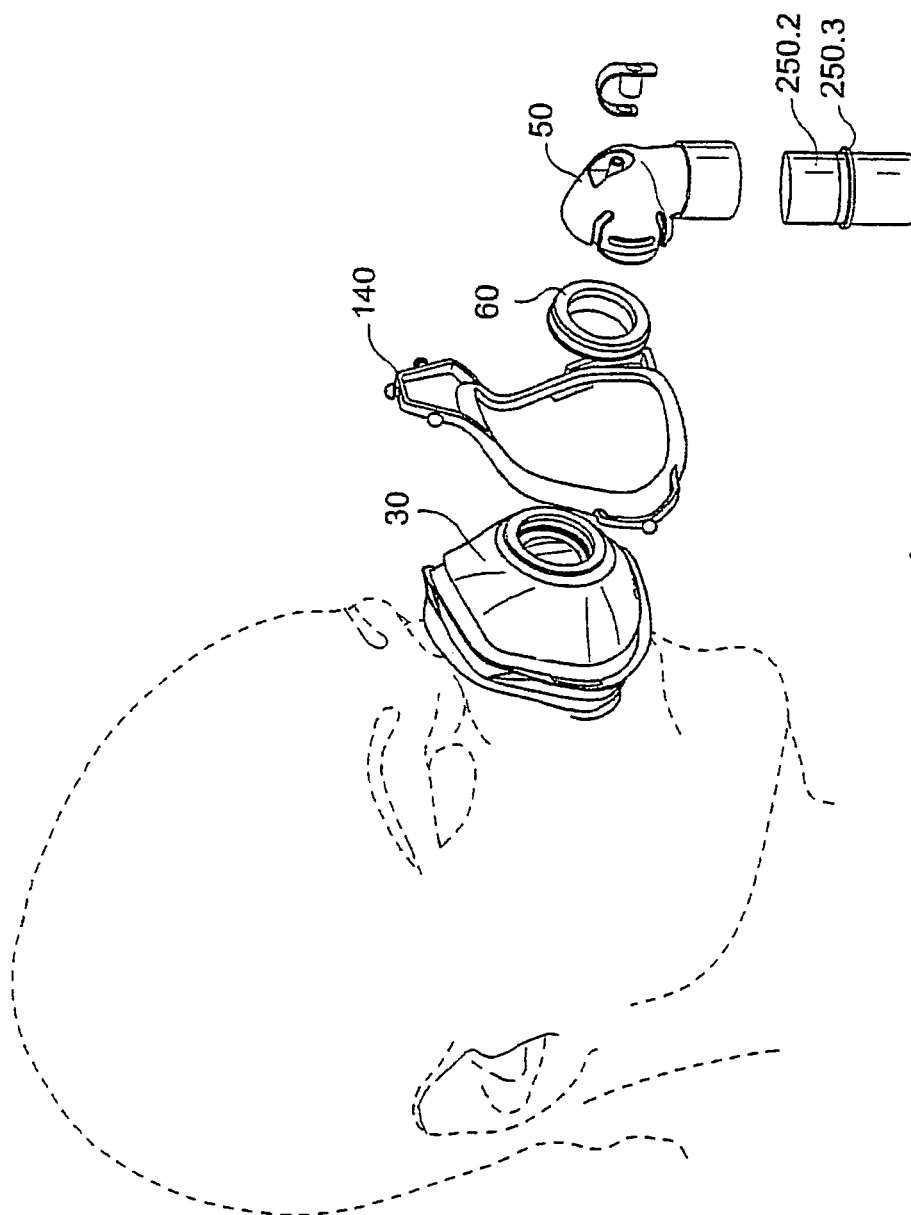
FIG. 11 shows an exploded view of another mask assembly near the face of a patient having a frame similar to that used in FIG. 10 but with a shell/cushion similar to that used in FIGS. 1 and 7.
Figure 68A:
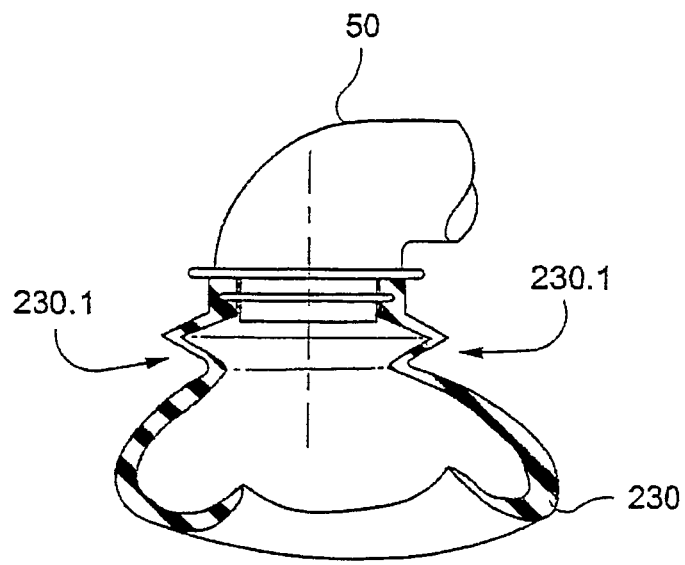
FIG. 68A shows a shell/cushion with a bellows portion demonstrating decoupling of the torque transfer between the elbow and the cushion.
Figure 68B:
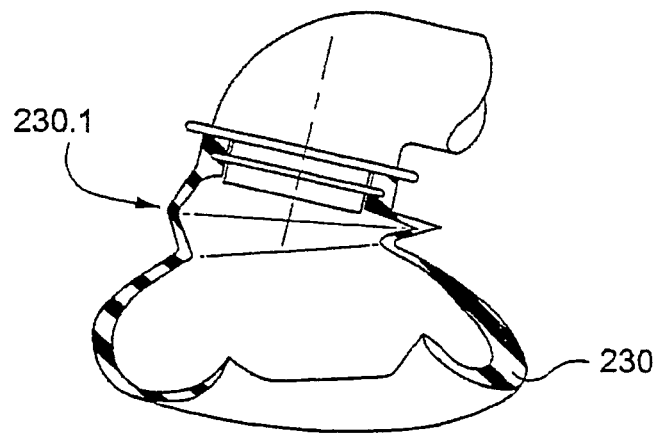
FIG. 68B shows the shell/cushion of FIG. 68A whereby the bellows portion is in the action of decoupling torque.

Multiple versions of the mask system are described with respect to the drawings:

Version 1: as depicted in FIGS. 1 and 7 being reusable with components which disassemble for cleaning with a three point single piece frame and having a shell/cushion with a continuous channel to receive the frame;

Version 2: as depicted in FIGS. 2 to 6, 8 and 9, being reusable with components which disassemble for cleaning with a three point single piece frame and having a shell/cushion with four discrete channels to receive the frame;

Version 3: depicted in FIG. 10 being a single use or disposable unit with components which disassemble for cleaning with a five point single piece frame;

Version 4; depicted in FIG. 11 being a reusable unit with components which disassemble for cleaning with a five point single piece frame;

Version 5: is not illustrated per se, but is a single use or disposable unit with a three point two piece frame;

Version 6: is not illustrated per se, but is a reusable unit with components which disassemble for cleaning with a three point two piece frame;

Version 7: is a single or disposable unit, such as in versions 3 or 5 with an elbow or connection piece as depicted in FIGS. 99 to 108;

Version 8: is a reusable unit, such as in versions 1, 3, 5 with an elbow or connection piece as depicted in FIGS. 89 to 98; and Version 9: is not illustrated per se, but is a reusable or single use unit of any of the previous eight versions, with a shell/cushion as depicted in FIG. 68.

The embodiments also include four versions of elbows or connection pieces for connecting a mask to a conduit, whereby the connection piece completes the mask:

Version A: is a reusable disconnectable elbow as depicted in FIGS. 30 to 37;

Version B: is a single use elbow which once assembled to a mask cannot be disassembled therefrom and is as depicted in FIGS. 38 to 46;

Version C: is a reusable disconnectable elbow as depicted in FIGS. 89 to 98; and Version D: is a single use elbow which once assembled to a mask cannot be disassembled therefrom and is as depicted in FIGS. 99 to 108.

The embodiments further include five versions of frames, which connect to the shell/cushions and the headgear to position the mask assemblies on a patient:

Version (i): a single piece three point frame receivable in a channel in a shell/cushion as depicted in FIGS. 13 to 20;

Version (ii): a single piece five point frame receivable in a channel in a shell/cushion as depicted in FIGS. 21 to 25;

Version (iii): a two piece three point frame as depicted in FIGS. 69 to 88, which will sandwich a flange on a shell/cushion to provide the shell/cushion with an exoskeletal support structure.

Version (iv): which is not illustrated, but us a two piece five point frame, which will sandwich a flange on a shell/cushion to provide the shell/cushion with an exoskeletal support structure. This version will be similar to Version (iii) as depicted in FIGS. 69 to 88; and Version (v): which is not illustrated, where the frame is a single piece and rivets to a flange on the shell/cushion.

The embodiments further include eight versions of shell/cushions:

Version I: being as depicted in FIGS. 1, 7, and 56 to 66, whereby the shell/cushion has a single continuous channel to receive the frame, for re-use duty;

Version II: being as depicted in FIGS. 1, 7, and 56 to 66, whereby the shell/cushion has a single continuous channel to receive the frame, for single use duty;

Version III: being as depicted in FIGS. 2 to 6, and 47 to 55, whereby the shell/cushion has a plurality of discrete channels to receive the frame, for re-use duty;

Version IV: being as depicted in FIGS. 2 to 6, and 47 to 55, whereby the shell/cushion has a plurality of discrete channels to receive the frame, for single use duty;

Version V: being as depicted in FIGS. 109 to 117, whereby a flange is provided around the periphery and is for re-use duty;

Version VI: being as depicted in FIGS. 109 to 117, whereby a flange is provided around the periphery and is for single use duty;

Version VII: is not illustrated but is similar to the shell/cushion of FIGS. 109 to 117, except that it has a plurality of discrete flanges or housing around the apertures and is for re-use duty; and Version VIII: is not illustrated but is similar to the shell/cushion of FIGS. 109 to 117, except that it has a plurality of discrete flanges or housing around the apertures and is for single use duty.

As illustrated in FIG. 1, the mask system 1, generally comprises a mask assembly 10 having a shell/cushion 30, a frame 40, a connecting piece or elbow 50 and a retaining ring 60 (which is not visible in FIG. 1, but is visible in FIG. 7). As will be readily understood, the combination of the versions of the basic components as described above will yield a multitude of mask system configurations.

§2 Headgear

Figure 12:
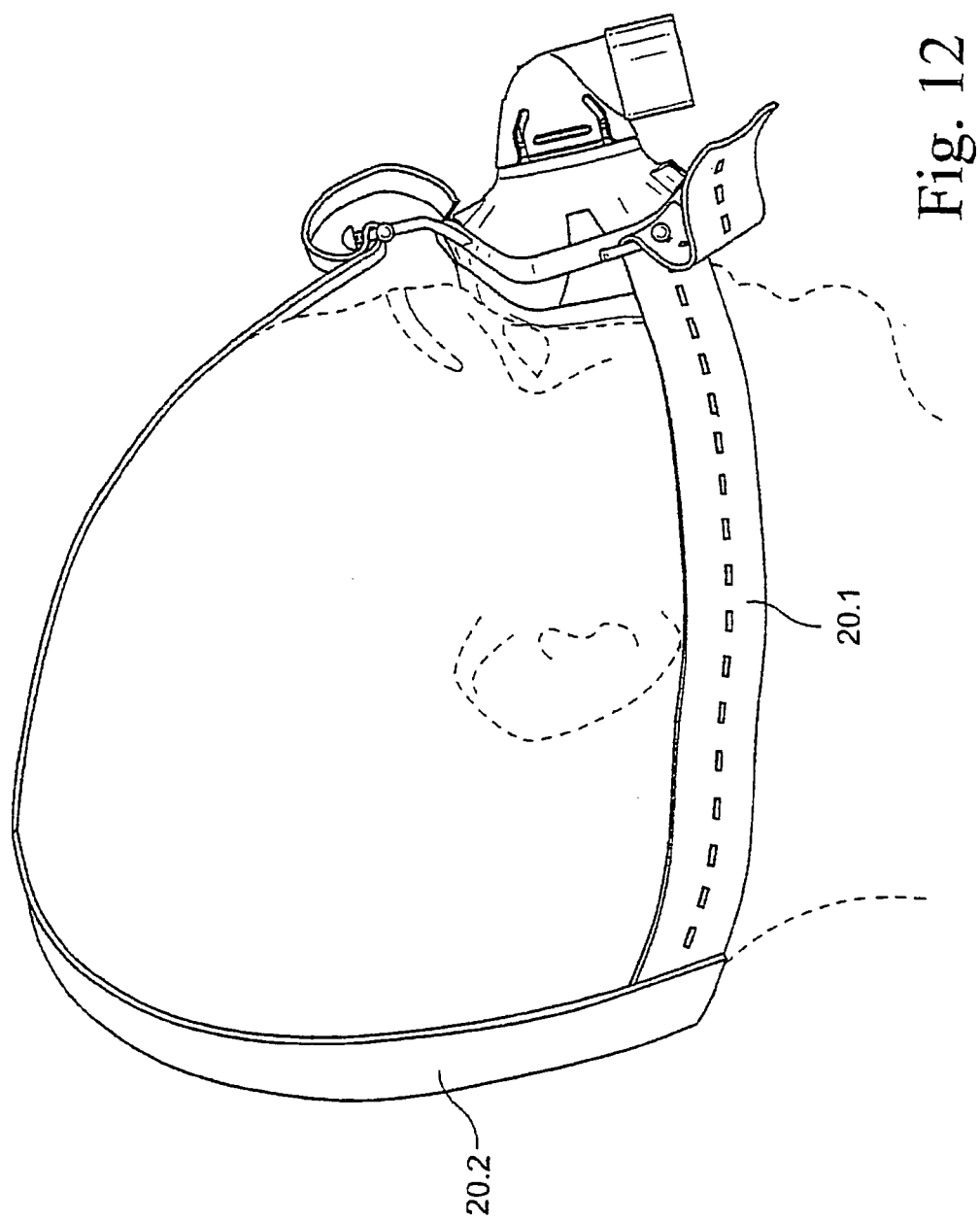
FIG. 12 shows a side view of the mask assembly of FIG. 11 including disposable headgear in use.
Figure 13:
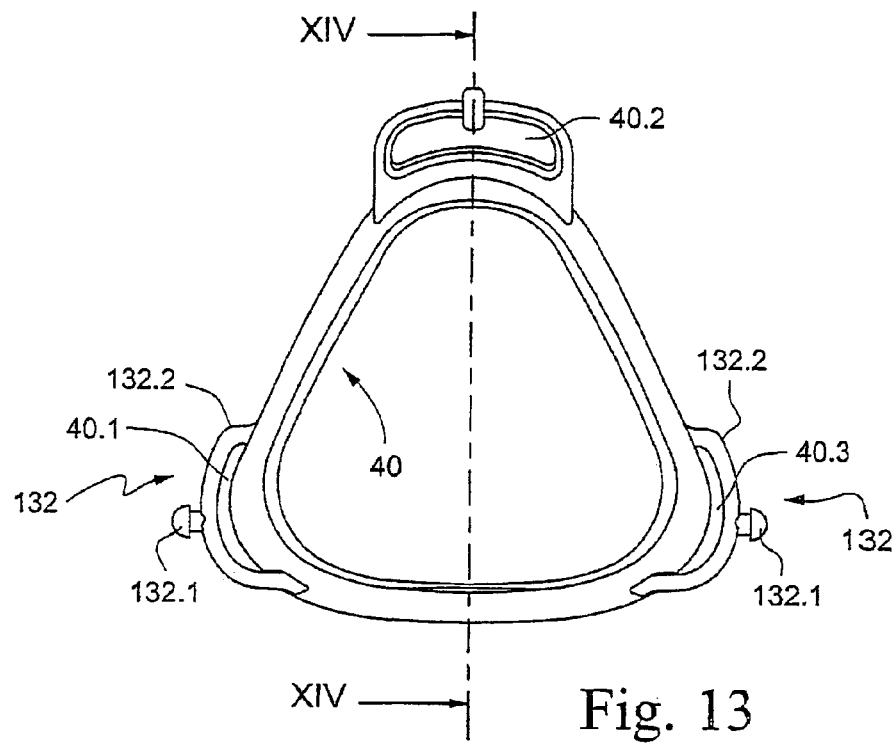
FIG. 13 illustrates a front elevation of a three point frame as used in the mask assembly of FIG. 2.

The headgear 20, as illustrated in FIGS. 1, 12 and 67 is composed of three separate strap pieces 20.1, 20.2 and 20.3 which are comprised of white non-latex elastic tape joined together to form a three point headgear system. Headgear 20 is attached to the frame 40 via the button holes 20.4 in the straps 20.1 and 20.2.

Table 1 shows exemplary dimensions of each of the straps 20.1, 20.2 and 20.3.

TABLE 1

| Drawing ref | Strap length (mm) | Quantity |
| --- | --- | --- |
| 20.1 | 500-700 | 1 |
| 20.2 | 350-500 | 1 |
| 20.3 | 150-250 | 1 |

Button holes (3-5 mm) are placed in the middle along the entire length of the straps with gaps between two button holes of approximately 3.5-6.5 mm. The straps 20.1, 20.2 and 20.3 are each 20 mm wide and constructed from a knitted 70% polyester and 30% non-latex elastomer which is white and biocompatible. The elasticity of the preferred material is 49+−20 Newtons per metre Nm-1. The above dimensions and materials are exemplary only.

Ordinarily headgear can represent a significant cost in the manufacture of a mask system. Thus, by manufacturing the headgear 20 from this particular low cost material can lead to a significant cost saving for the headgear and the mask system as a whole.

The headgear 20 described above is preferably used for a single use and then disposed of. However, to make the headgear in a reusable form, the headgear can be moulded in a number of parts and joined together with buttons or similar. Alternatively reusable headgear can be moulded in one piece.

FIG. 67 shows a plan view of the headgear 20 while FIG. 12 shows the headgear 20 in use on a model head.

§3 Shell/Cushion

Illustrated in FIGS. 1, 7, 11, and 56 to 66 is the shell/cushion 30. The shell/cushion 30 defines a nose-receiving cavity 30.1 and forms a seal with the face of the patient. The shell/cushion 30 has a rearward aperture 30.2 through which the patient's nose passes in use and a front aperture 30.3 to which a connection piece or elbow 50 is attached. In a preferred form, the shell/cushion 30 is single walled, however in other forms it may have two or more walls, similar to the mask as taught in U.S. Pat. No. 6,112,746 (incorporated herein by reference), known by the trade mark MIRAGE®. The shell/cushion 30 has a sealing structure 30.5 and a support structure 30.4 of a substantially constant cross section. It can be moulded from any appropriate material such as silicone or a thermoplastic elastomer.

The sealing structure 30.5 has a face contacting side 30.51 adapted to form a seal on a patient's face. The face contacting side 30.51 includes a nasal bridge region 30.6, side regions 30.7 and a lip region 30.8. As can be seen from the figures the lip region 30.8 has a series of four vent orifices 30.9 passing therethrough. The face contacting side 30.51 is similar in shape to the face contacting side of the mask known by the trade mark PAPILLION (manufactured by MAP GmbH) or the mask known by the trade mark MIRAGE (manufactured by ResMed Limited).

A range of shell/cushion 30 sizes can be provided to suit different sizes of noses. For example, in one form, shell/cushions can have a shallow nasal bridge region 30.6.

The shell/cushion 30 includes a frame-receiving channel 140 defined by a front flange 34 and a rear flange 36. The shell/cushion 30 of FIGS. 7, 8 and 56 to 61 has the front flange 34 of a frame-receiving channel 140 as a continuous or unbroken channel, which extends 100% of the way around the perimeter of the shell/cushion 30.

Figure 56:
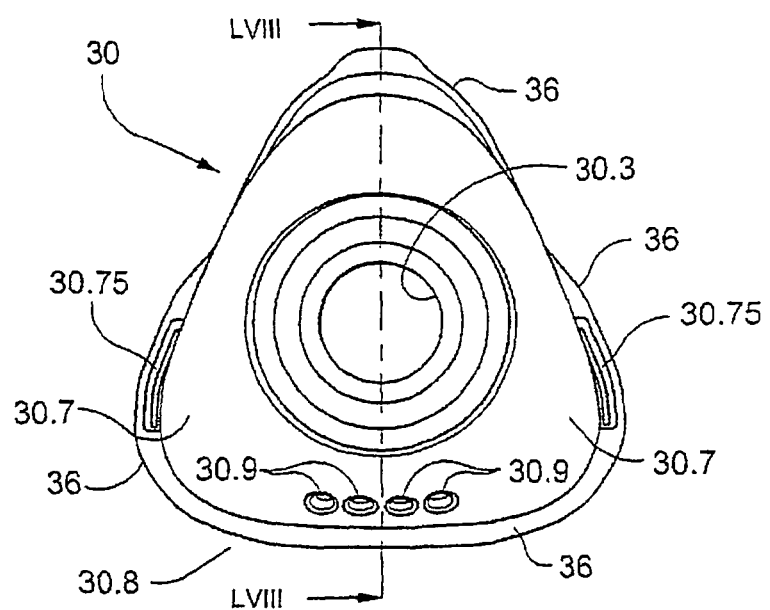
FIG. 56 illustrates a front elevation of a shell/cushion having a continuous channel around the periphery to attach a frame.
Figure 57:
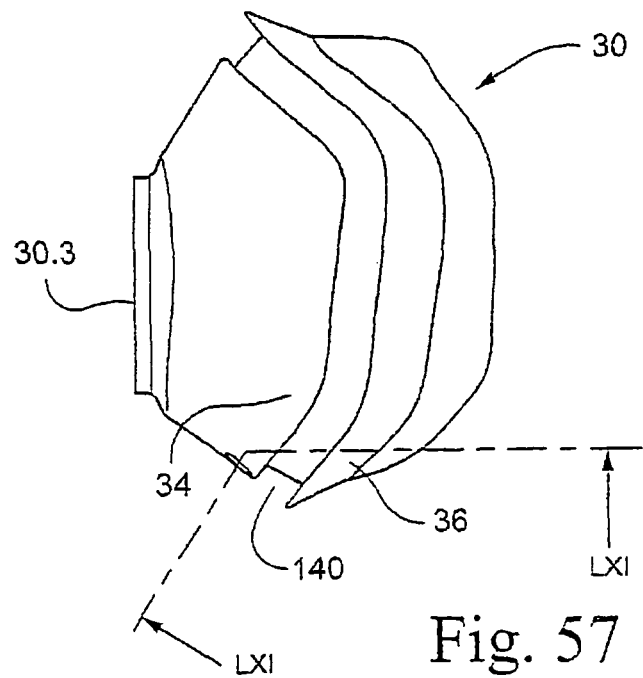
FIG. 57 illustrates a right side elevation of the shell/cushion of FIG. 56.
Figure 58:
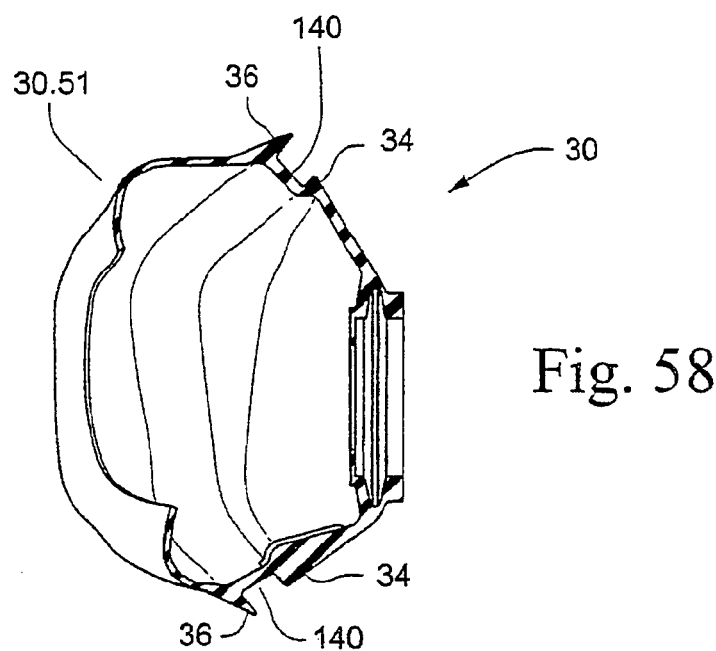
FIG. 58 illustrates a cross section through the line LVIII-LVIII of the shell/cushion of FIG. 56.
Figure 59:
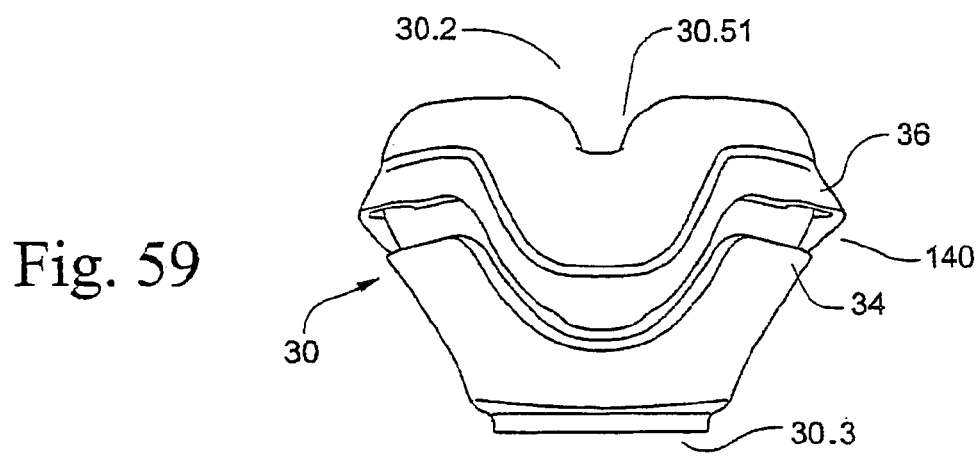
FIG. 59 illustrates a plan view of the shell/cushion of FIG. 56.
Figure 60:
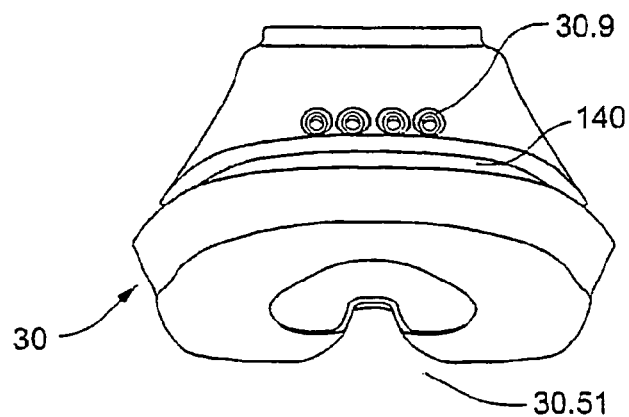
FIG. 60 illustrates an underneath view of the shell/cushion of FIG. 56.
Figure 61:
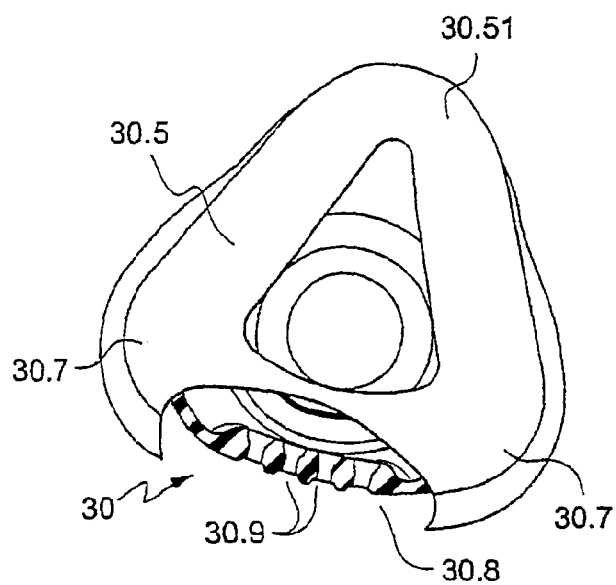
FIG. 61 illustrates a cross section through line LXI-LXI of the shell/cushion of FIG. 57.
Figure 62:
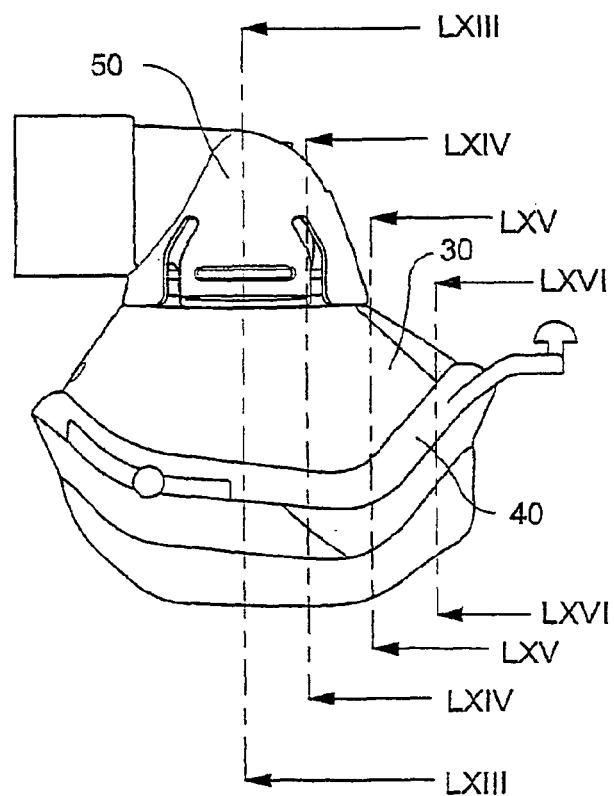
FIG. 62 illustrates the side elevation of a mask assembly of the shell/cushion of FIGS. 56 to 61, the frame of FIGS. 13 to 20 and the elbow of FIGS. 30 to 37.

As is visible in FIG. 56, the rear flange 36 is somewhat wider in the lip region 30.8 and side regions 30.7. In these wider portions on both the side regions 30.7 are elongated recesses 30.75 which provide an additional structure to engage and locate the frame 40 or 140, as will be described below.

Illustrated in FIGS. 2 to 6, 8, 9, 10 and 47 to 55 is another a shell/cushion 130. The shell/cushion 130 is similar to the shell/cushion 30 and like parts have been like numbered. The shell/cushion 130 differs from the shell/cushion 30 in that instead of a continuous or unbroken channel 140 being provided all the way around the shell/cushion, discrete channels 140.1, 140.2 and 140.3 are provided to cooperate with a fourth channel 140.4 (see FIG. 48) to form four discrete points to receive four points on a frame 40 therein. Each channel discrete 140.1, 140.2, 140.3 and 140.4 is formed between a continuous rear flange 36, and an intermittent front flange 34. The rear flange 36 surrounds the shell/cushion 130 all the way around the periphery thereof so as to provide a flange against which the frame 40 or 140 can push. The portion of the rear flange 36 in the lower side regions 30.7 and lip region 30.8 are thicker than in the nasal bridge region 30.6 so as to prevent a "knife edge" forming in the nasal bridge region 30.6, but provide structure to form the two lower apexes of the shell/cushion 30.

Figure 3:
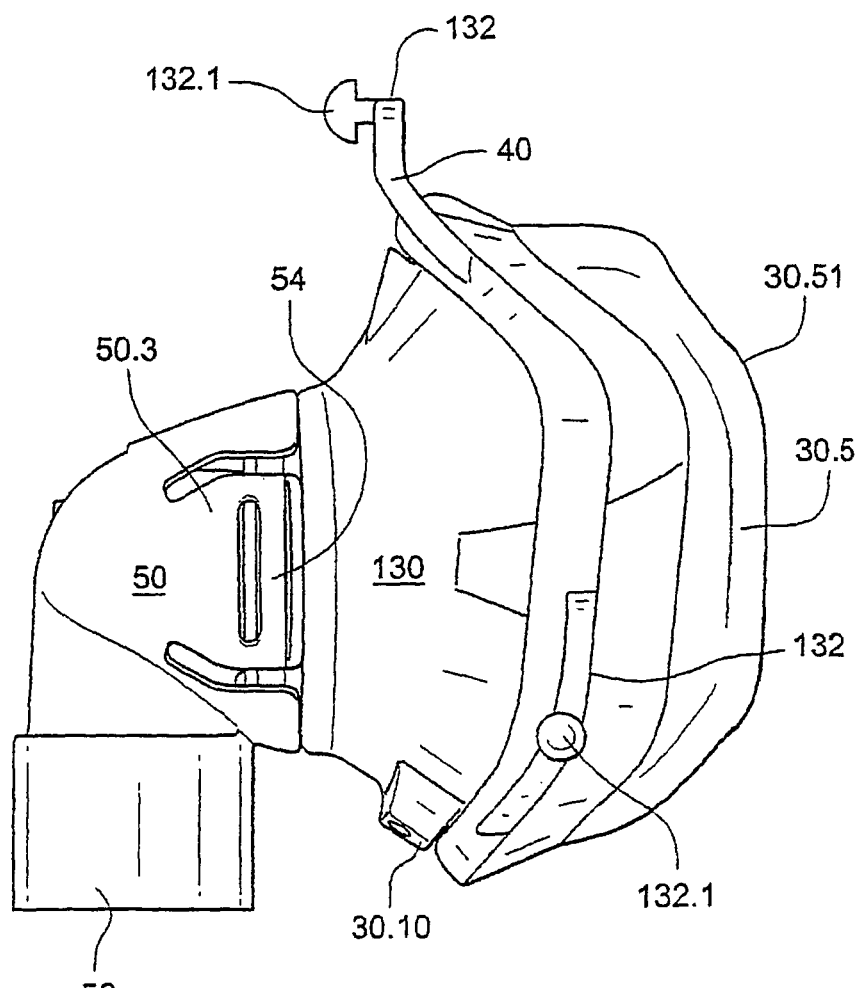
FIG. 3 shows a side view of the mask assembly of FIG. 2.
Figure 4:
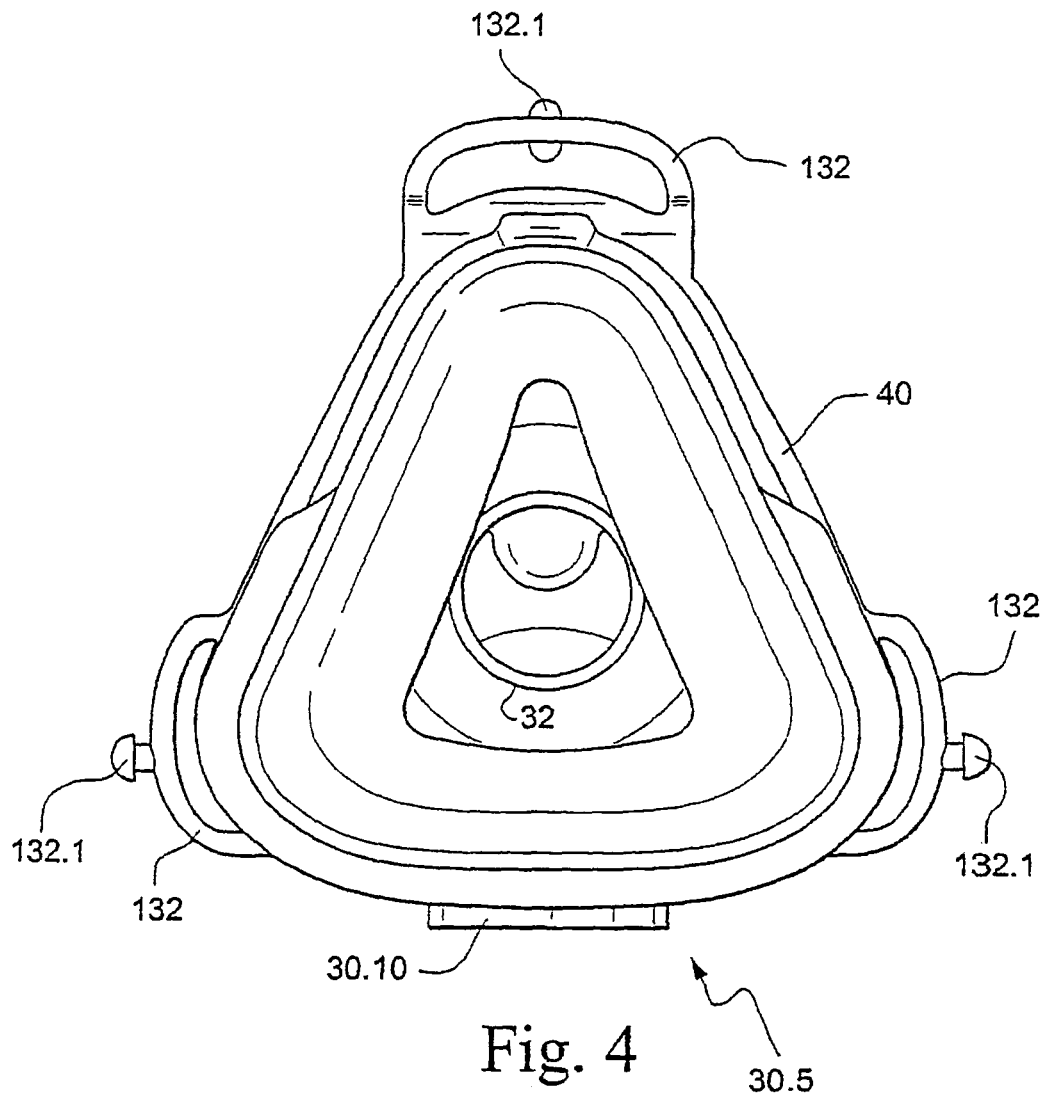
FIG. 4 shows a rear view of the mask assembly of FIG. 2.
Figure 5:
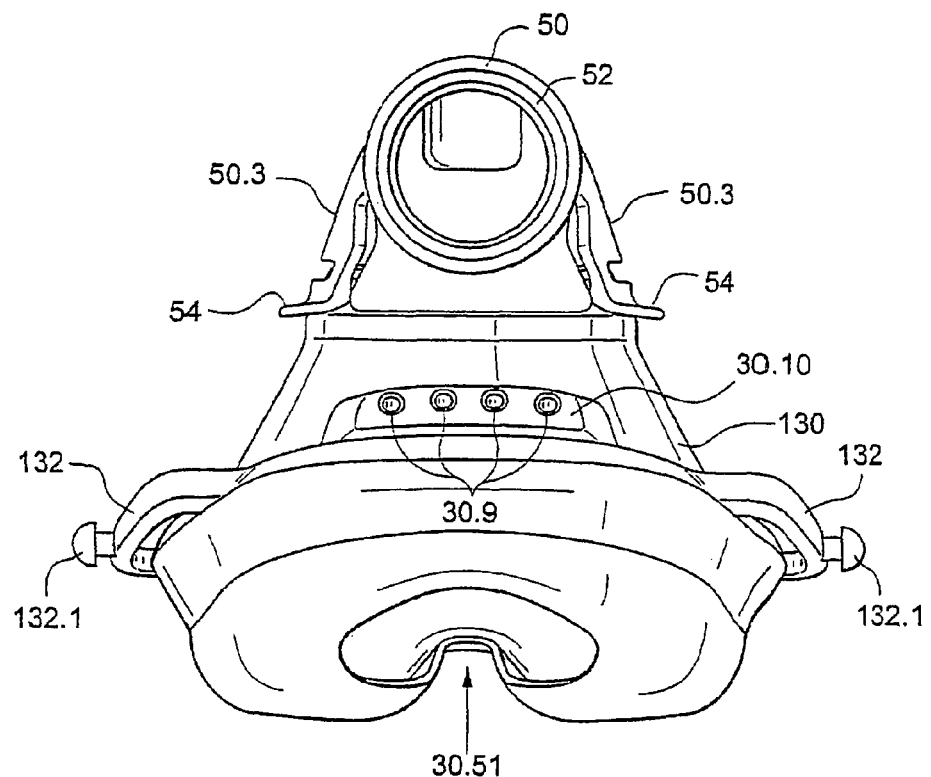
FIG. 5 shows a bottom view of the mask assembly of FIG. 2.
Figure 6:
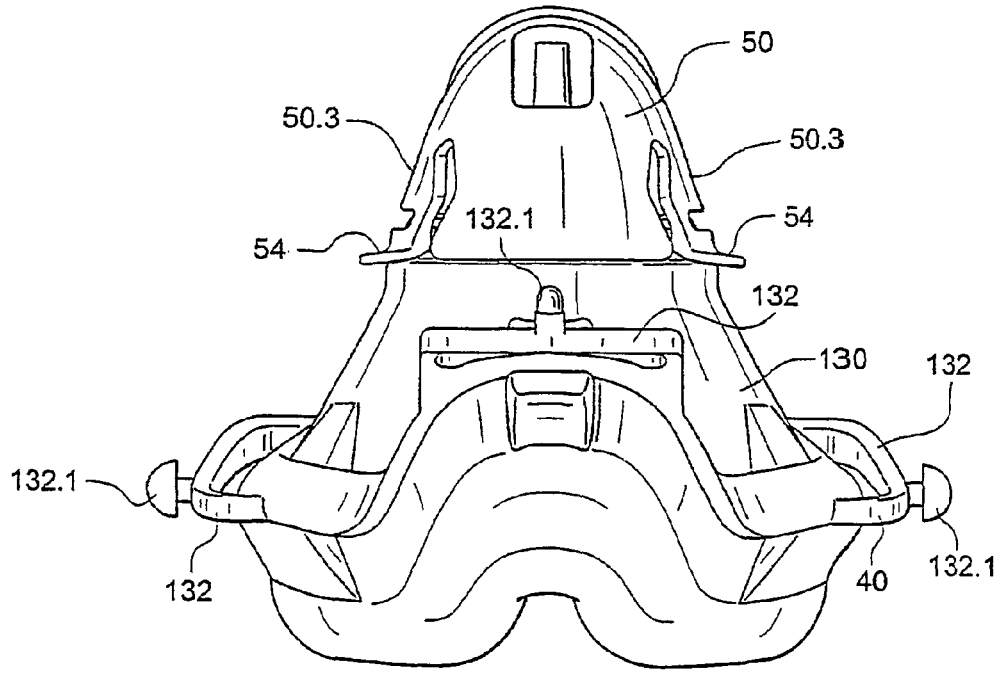
FIG. 6 shows a top view of the mask assembly of FIG. 2.

The shell/cushion 130 includes a series of vents or vent orifices 30.9, which in a preferred form comprises four orifices. The vent orifices 30.9 are formed through a thicker wall section 30.10 formed integrally on the shell/cushion 30. The wall section 30.10 is shown in FIG. 3. The wall section 30.10 has two functions. The first is to form a front flange which with the rear flange 36 in the lip region 30.8 forms the lower channel 140.4. The second function is that the wall section 30.10 allows the vent orifices 30.9 to be positioned at an angle with respect to the elbow. However, the vent orifices 30.9 can be constructed at a flatter angle, for example, 10° to 15° from the vertical (with respect to the orientation shown in FIG. 3) so that when a patient is wearing the mask system 1 and lying down, the vent orifices 30.9 will be aligned generally at 10° to 15° from the horizontal).

Figure 66:
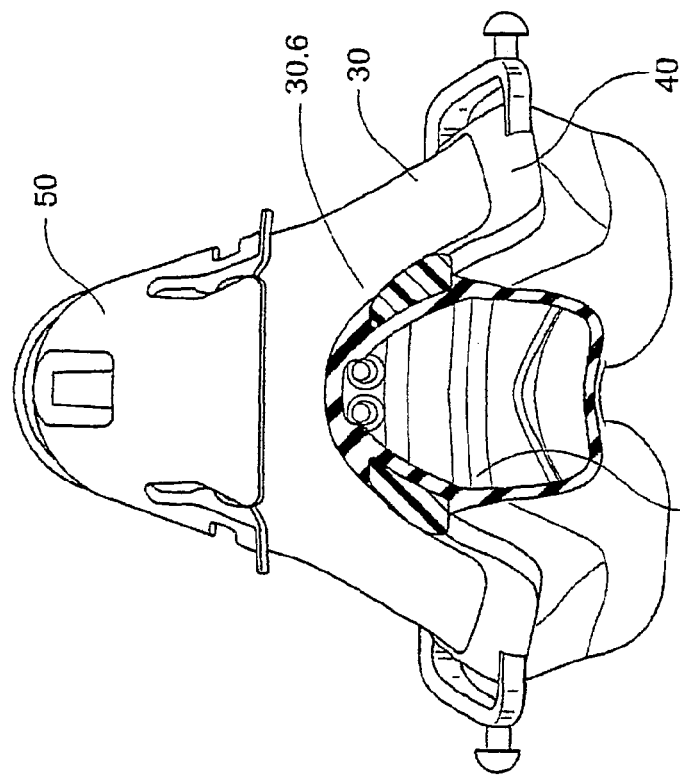
FIG. 66 illustrates a cross section through the line LXVI-LXVI of the mask assembly of FIG. 62.
Figure 65:
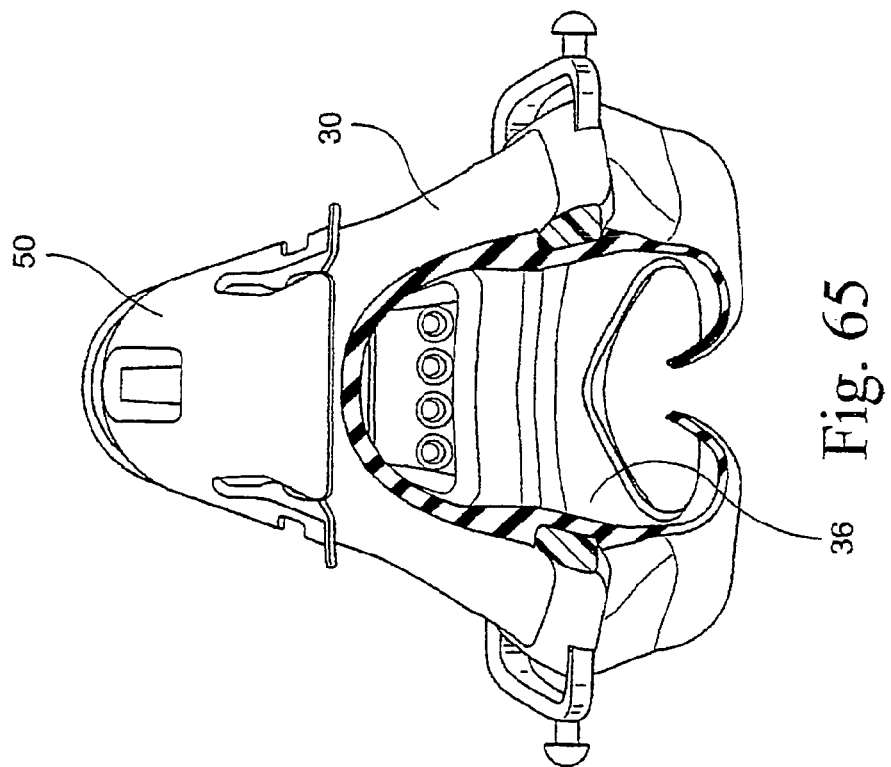
FIG. 65 illustrates a cross section through the line LXV-LXV of the mask assembly of FIG. 62.

As illustrated in FIGS. 4, 8, 9, 48, 49, 56 and 57 the rear flange 36 of the frame-receiving channel 140 has different thickness in different regions. This feature is common to both shell/cushions 30 and 130, but for convenience is described in the proceeding passages with respect to shell/cushion 30 only. It is thinner in the nasal bridge region 30.6 than in the lower side regions 30.7 and the lip region 30.8. The rear flange 36 is between 1 to 3 mm thick, preferably 2 mm thick in the nasal bridge region 30.6, but can be of the order of 5 mm in the lower side regions 30.7 and lip region 30.8. This provides sufficient support for the sealing structure 30.5 of the shell/cushion 30 in the nasal bridge region 30.6 but doesn't lead to the creation of a "knife-edge" which can be uncomfortable for a patient. A "knife edge" may form if the sealing structure 30.5 of the shell/cushion 30 collapses, and if a harder or thicker portion of the shell/cushion 30 was used at the nasal bridge region 30.6. A "knife edge" is undesirable because with prolonged use, it can create a pressure sore on a patient's face. FIGS. 63 and 64 show sections from FIG. 62 with thicker rear flange regions 36, whereas similar rear flange sections 36 in FIGS. 65 and 66 are shown with thinner rear flange regions.

Thus, as can be seen from the shell/cushion 30 and 130, the shell/cushion can be provided with discrete channels or a continuous channel. The channel or channels can, when their length is totaled, be in the range of 75% to 100% of the perimeter of the shell/cushion as in the case of shell/cushion 30 or in the range of 20% to 40% as in the case of shell/cushion 130 of the frame 40. An advantage of the front flange extending 75% to 100% of the way around the perimeter is that it is less likely to be removed by inadvertence. From FIGS. 56 and 47 it can be seen that the shell/cushions 30 and 130 have the wider portion of the rear flange 36 extending around the two lower apexes, so as to occupy approximately 60% of periphery of the shell/cushion 30 and 130. To achieve the desired structural function and flexibility in the nasal bridge region, this wider flange could occupy approximately 40% to 80% of the periphery of the shell/cushions 30 and 130 centered around the lower regions thereof.

Figure 52:
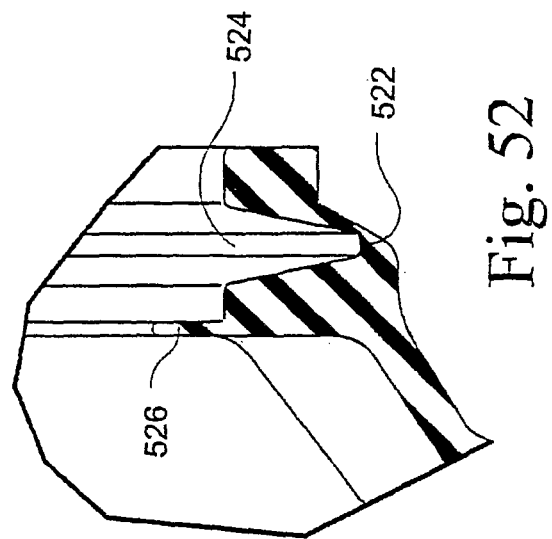
FIG. 52 illustrates detail Z of the cross section of FIG. 49.
Figure 51:
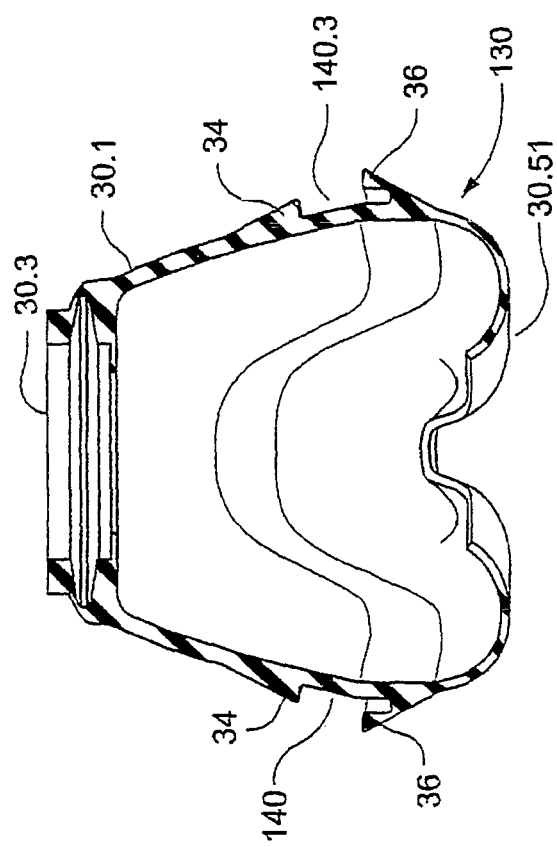
FIG. 51 illustrates a cross section through the line LI-LI of the shell/cushion of FIG. 47.

FIG. 52 shows in cross-section a portion 30.31 of the shell/cushion 130. The portions 30.31 are those portions linked to the front aperture 30.3, which will receive the retaining ring 60. The region 30.31 has a channel 524 into which the rear flange of the retaining ring 60 will be received. The patient end of the aperture has an annular flap 526 which is relatively thin and flexible, and which reduces the inside diameter of the aperture 30.3. The purpose of the flap 526 is to provide a seal with a portion of the connection piece or elbow 50, as will be described below in chapter §7 Assembly of the components below.

The section 522 as illustrated in FIG. 52 is a relatively thin walled section. Such a thin walled section is particularly useful for the manufacture of a disposable mask. The thin walled section 522 can thus be designed to tear if a person attempts to remove the connection piece or elbow 50, for example to wash the elbow 50. This aspect represents a safety feature preventing re-use of a disposable mask having a shell/cushion 130, reducing the likelihood of cross-infection.

Alternatively, if the shell/cushion 130 were to be reusable then the section 522 will be provided with a thicker dimension which would prevent the section 522 tearing at the time of disassembly. The shell/cushion 30, being of a reusable nature, will have a cross section similar to that of FIG. 52 with the section 522 being of a thicker dimension than that for shell/cushion 130.

Illustrated in FIG. 68 is a diagrammatic representation of a modified shell/cushion 230. In this shell/cushion 230 a small bellows portion 230.1 is provided (or a alternatively a flexible neck can be provided) adjacent the aperture 30.3 where a connection piece or elbow 50 fits into the shell/cushion 230. This bellows portion 230.1 provides a flexible element which allows movement between the connection piece or elbow 50 and the shell/cushion 230. By providing this flexibility there is a decoupling of any torque which may attempt to transfer between the elbow and the shell/cushion.

Illustrated in FIGS. 109 to 117, 122 and 123 is another shell/cushion 330, which is similar to the shell/cushions 30 and 130 described above with like parts being like numbered. The shell/cushion 330 differs from the shell/cushions 30 and 130 in that instead of a channel 140, or a series of discrete channels 140.1, 140.2, 140.3 and 140.4 being provided around the periphery to receive a frame 40, a continuous peripheral flap or flange 330.1. The flange 330.1 has the same shape as a two piece frame (see description below with respect to FIGS. 69 to 88) which will sandwich the flange 330.1.

The flange 330.1 includes seven apertures 330.2 and 330.3 therethrough. The four apertures 330.2 are of an approximate diameter of 5.75 mm while the three apertures 330.3 are of an approximate diameter of 3 mm. The apertures 330.2 and 330.3 receive therethrough rivets formed on one piece of the two piece frame as will be described below. As the rivets which pass through the apertures 330.2 have a barbed head which is of a larger diameter than the shank the apertures 330.2 are of a larger diameter to accommodate this large diameter barb.

While FIGS. 109 to 117 display a continuous flange 330.1 around the periphery of the shell/cushion 330, a satisfactory result is also expected should a series of seven discrete flanges or housing were to be provided around the apertures 330.2 and 330.3. Whilst this will give the frame which sandwiches these flanges some seven points of grip or contact with shell/cushion, these seven points are expected to be sufficient to maintain the shape of the shell/cushion when it is in use.

Figure 114:
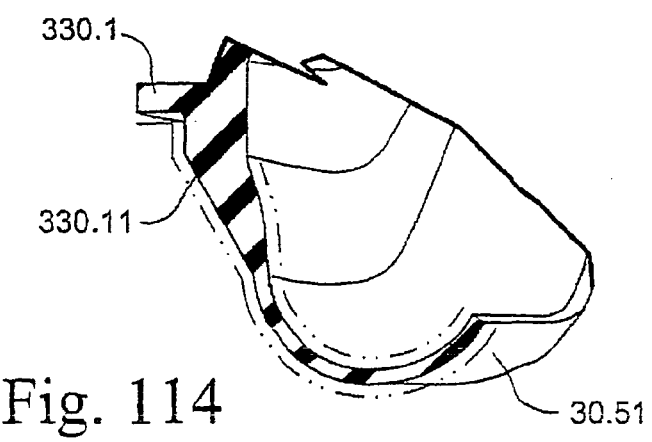
FIG. 114 illustrates in detail a portion of the cross section of FIG. 111.
Figure 114A:
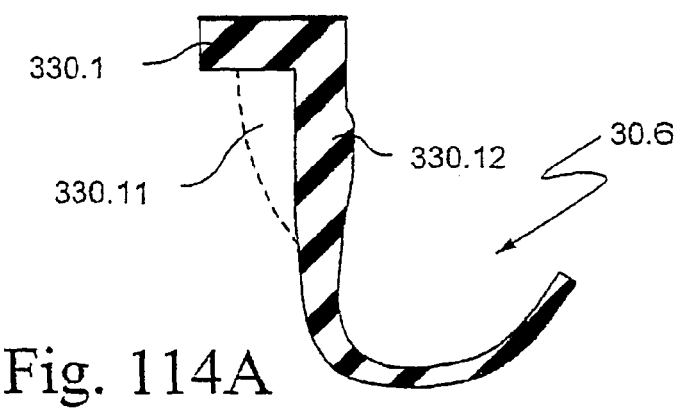
FIG. 114A illustrates in detail a portion of the shell/cushion in the nasal bridge region.

As can be seen from FIG. 114 the exterior of the shell/cushion 330, which provides a seal with a patients face, has a shot blasted surface finish. Such a shot blasted finish will provide a more comfortable feel for the patient. The cross section of FIG. 114 is taken through the middle region of the shell/cushion 330. It can be seen in FIG. 114, that in the region designated by the wall 330.11, behind the flange 330.1, the thickness of the wall 330.11 is kept relatively thick and then tapers in a rearward direction. In contrast to this, as is illustrated in FIG. 114A, in the nasal bridge region 30.6, the cross section is different, whereby the wall 330.11 (shown for comparison in phantom line) is thinned to form the wall 330.12 which is a relatively thinner and substantially constant cross section wall portion. This reduction in wall thickness in the nasal bridge region 30.6 helps to reduce the chances of a "knife edge" being formed in use on a patient, in the nasal bridge region 30.6.

Illustrated in FIGS. 109, 110, 112, and 113 the shell/cushion 330 is illustrated as having a manufacturing tab or de-moulding tab 330.13. The de-moulding tab 330.13 allows a robotic de-moulder to grab the shell/cushion 330 safely and securely, without having to grab any other parts of the shell/cushion 330. This can limit the possibility of damaging any of the other parts of the shell/cushion 330 in the process of cutting off any excess material by a robot which may have resulted from the moulding process.

Figure 115:
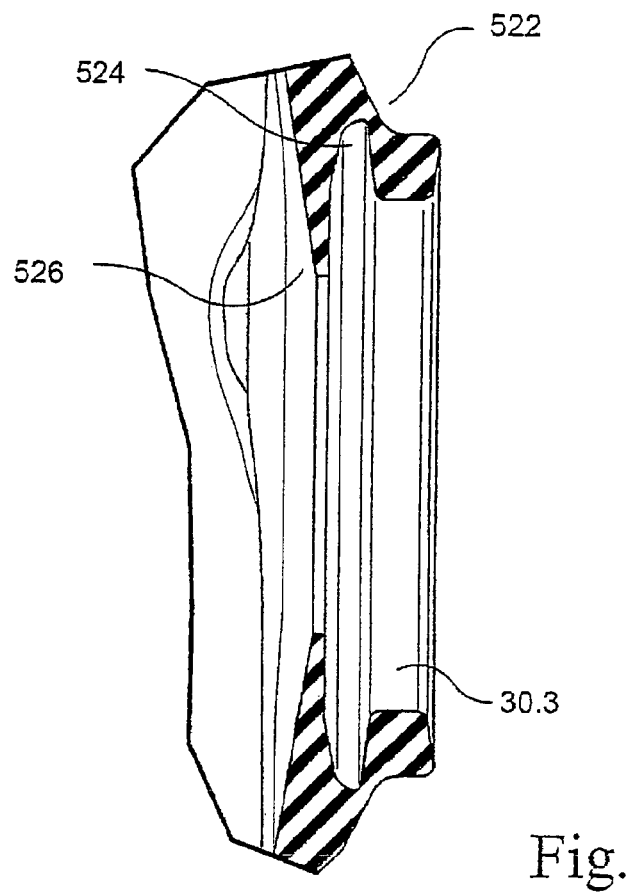
Figure 116:
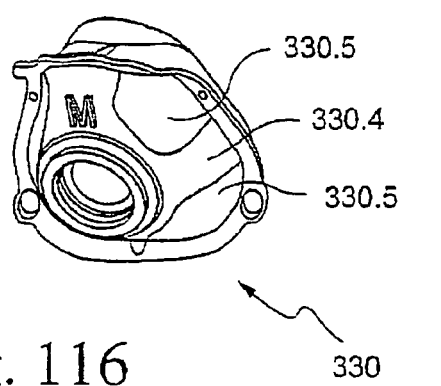
Figure 117:
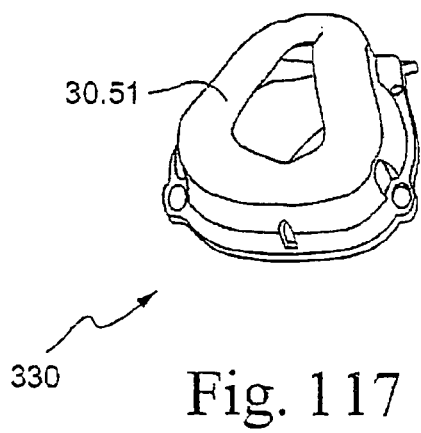
Figure 122:
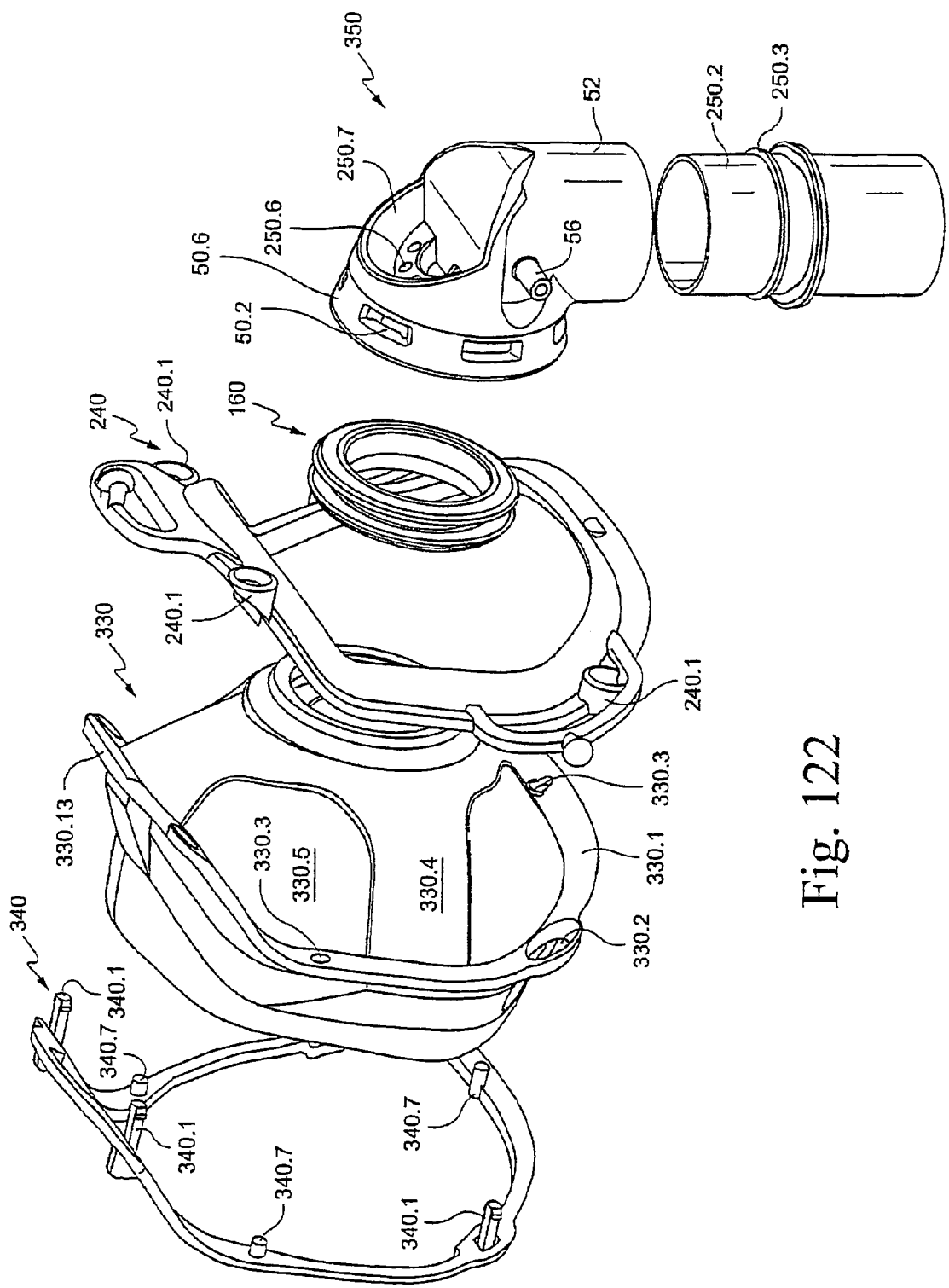
Figure 123:
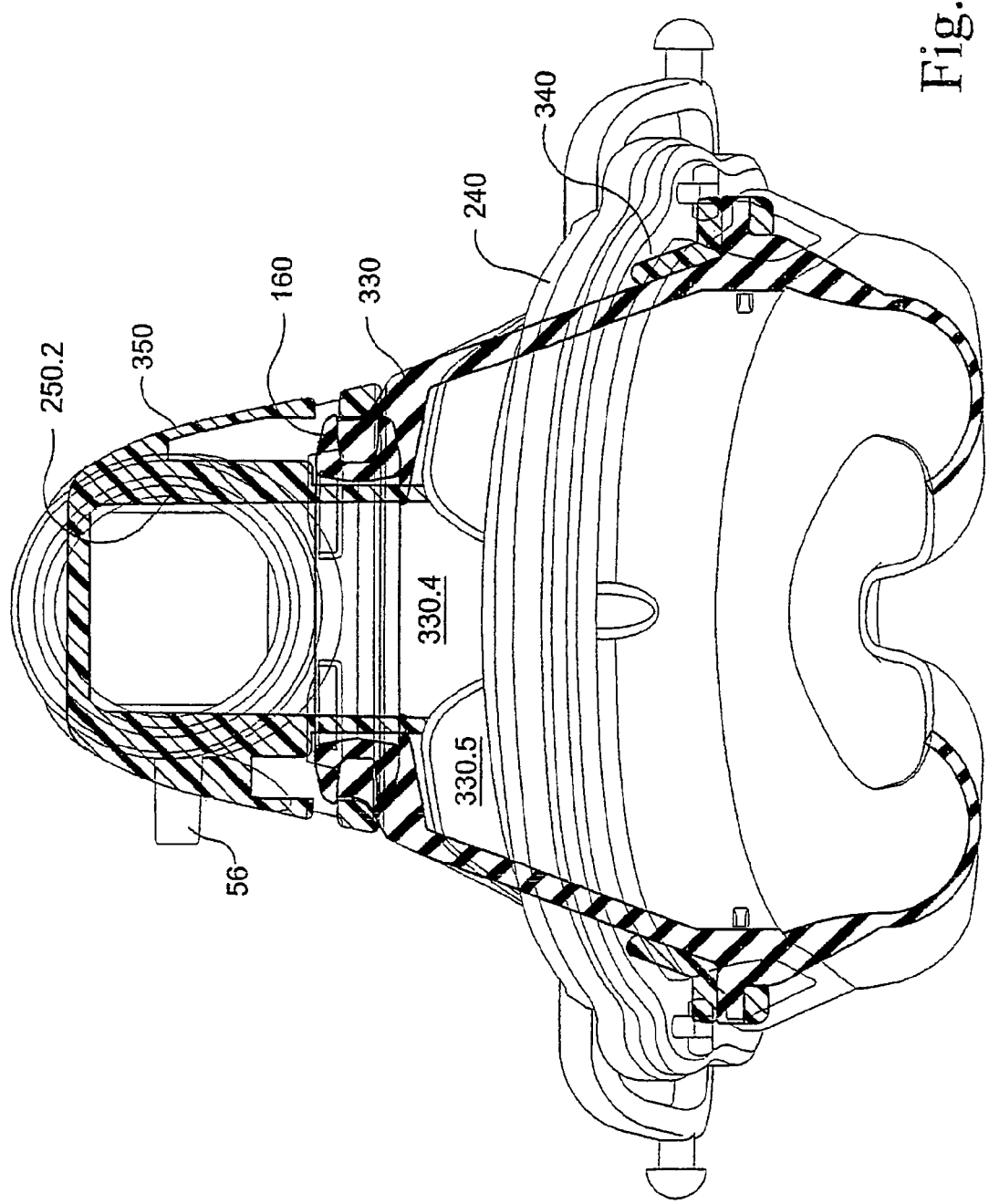

The shell/cushion 330 is specifically for one time hospital use. As can be seen form. FIG. 115, the shell/cushion 330 has a thin walled section, approximately 0.33 to 0.75 mm in thickness. As described above this will provide a line of weakness allowing the shell/cushion to tear, should it be attempted to remove the retaining ring 60 from the recess 524. The propensity to tear limits the ability to clean the shell/cushion 330 before re-use, thus preventing re-use.

To provide some additional rigidity whilst at the same time keeping the material used to a optimum level, there is provided on the shell/cushion 330 a series of four radially extending reinforcing ribs 330.4 which extend away from a generally circular reinforcing ring 330.6 which surrounds the region 30.31 and aperture 30.3. The ribs 330.4 and 330.6 are formed integrally in the shell/cushion 330, but are of a greater thickness of material than the regions 330.5. The ribs 330.4 and 330.6 are approximately 2 to 3 mm in thickness while the regions 330.5 are approximately 1 to 1.5 mm in thickness. This arrangement helps to provide better aesthetic quality while also providing greater structural support where required, but a softer feel at the seal locations.

§4 Frame

As is illustrated in FIGS. 1 to 9, and 12 to 18, the frame 40 is shaped and adapted to be mounted on the shell/cushion 30 and 130, and provides anchor points 132 having apertures 40.1, 40.2 and 40.3 for headgear 20. The frame 40 provides three anchor points 132 and is shown in detail in FIGS. 13 to 20.

The frame 40 is of a generally triangular shape with rounded apexes, and has a base approximately 90 mm wide and a height of approximately 84 mm. Other exemplary dimensions are as indicated in the FIGS. 13 to 20.

The frame 40 can be made to any suitable configuration of anchor points 132 so as to provide a variety of fittings to suit the particular needs of individual uses. In this regard, the placement of anchor points 132 can be changed in a manner described in the published PCT patent application WO 02/45784, the contents of which are hereby incorporated by cross reference. In this way the adaptability of the mask system 1 is enhanced as the mask frame 40 is relatively inexpensive to manufacture.

Each anchor point 132 is formed from a frame member 132.2 which surrounds an aperture 40.1, 40.2 or 40.3. The apertures 40.1, 40.2 and 40.3 allows the ends of the straps 20.1 and 20.2 to be threaded therethrough.

On a middle portion of the frame member 132.2 is a mushroom headed spigot 132.1, which can be threaded though one of the button holes 20.4 on the respective ends of the straps 20.1 and 20.2. In alternative embodiments the spigot may be replaced by other methods of retention such as hooks.

If desired the user need not thread through the apertures 40.1, 40.2 or 40.3, and instead attach directly onto the mushroom headed spigots 132.1, however, there is less likelihood of inadvertent disconnection when in use if the ends of straps 20.1 and 20.2 are threaded through the respective apertures 40.1, 40.2 or 40.3 as all movement of the ends of the straps 20.1 and 20.2 will not tend to try to pull the button holes 20.4 over the mushroom headed spigots 132.1.

Figures 14, 15:
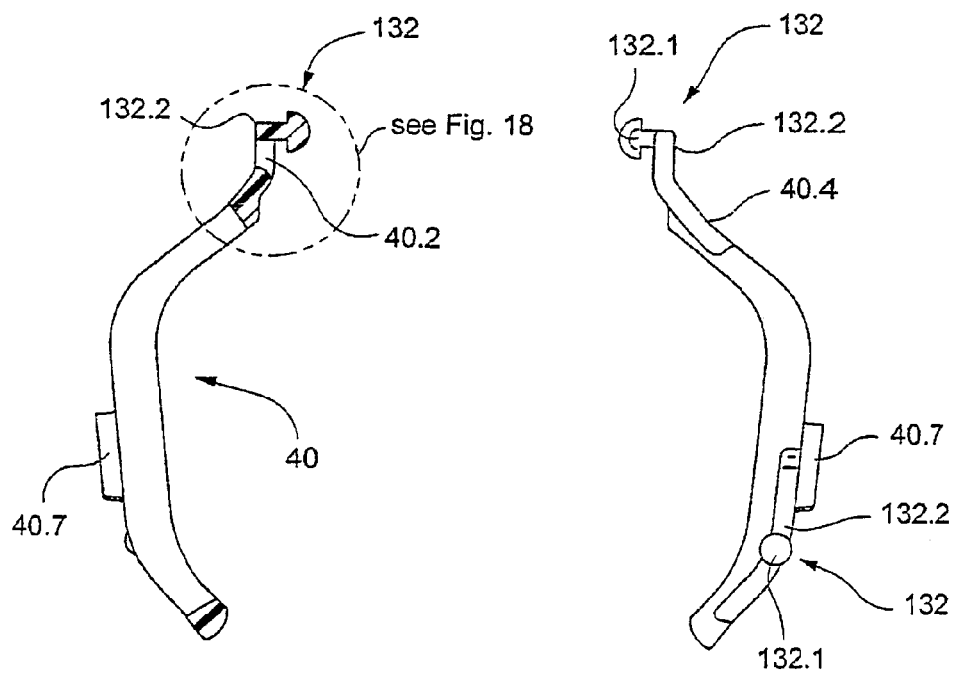
FIG. 14 illustrates a cross section through lines XIV-XIV the frame of FIG. 13.
FIG. 15 illustrates a right side elevation of the frame of FIG. 13.
Figure 16:
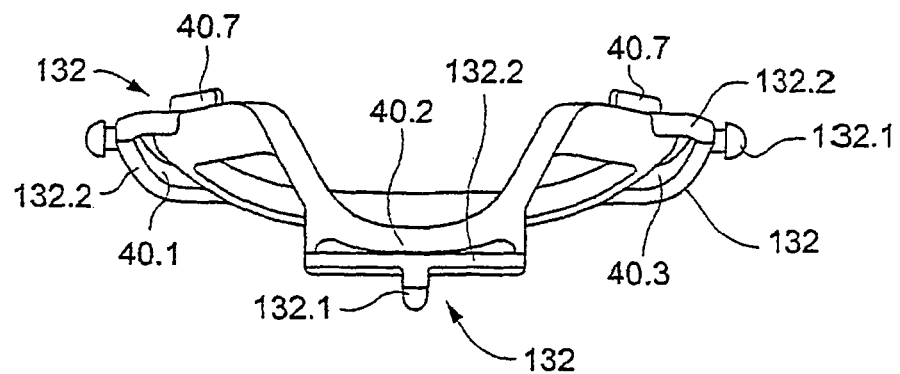
FIG. 16 illustrates a plan view of the frame of FIG. 13.
Figure 17:
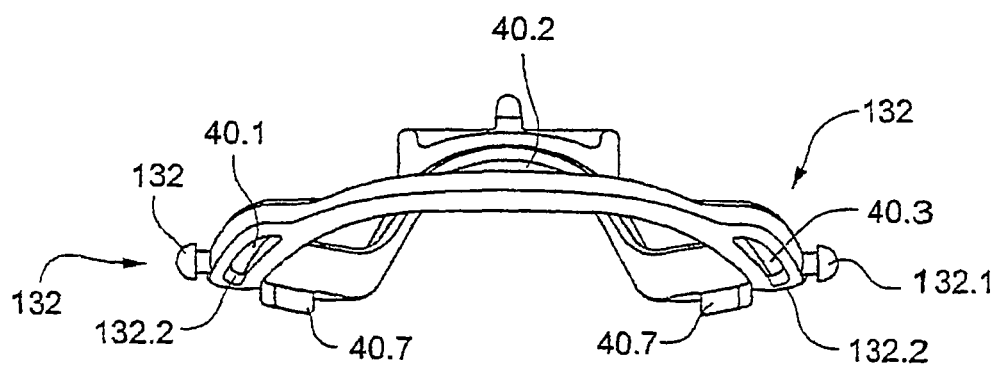
FIG. 17 illustrates an underneath view of the frame of FIG. 13.
Figure 19:
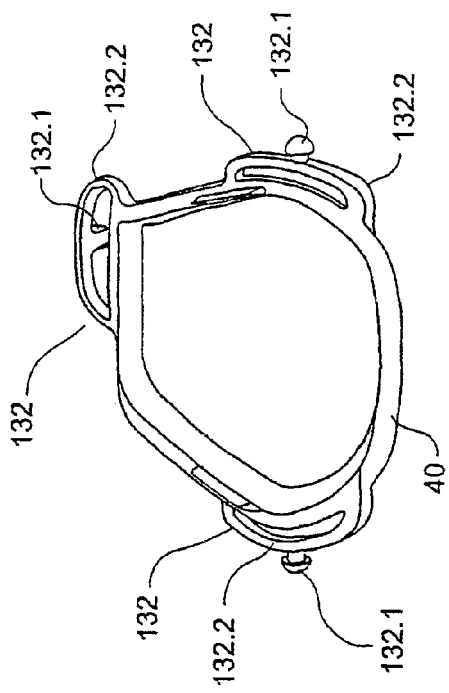
FIG. 19 illustrates a left hand side perspective view of the frame of FIG. 13.
Figure 20:
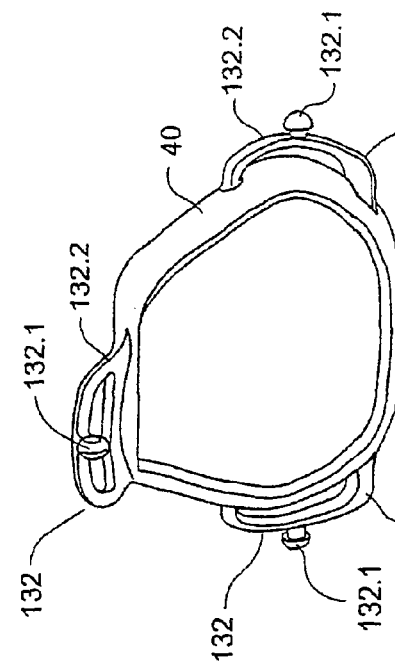
FIG. 20 illustrates a right hand side perspective view of the frame of FIG. 13.
Figure 18:
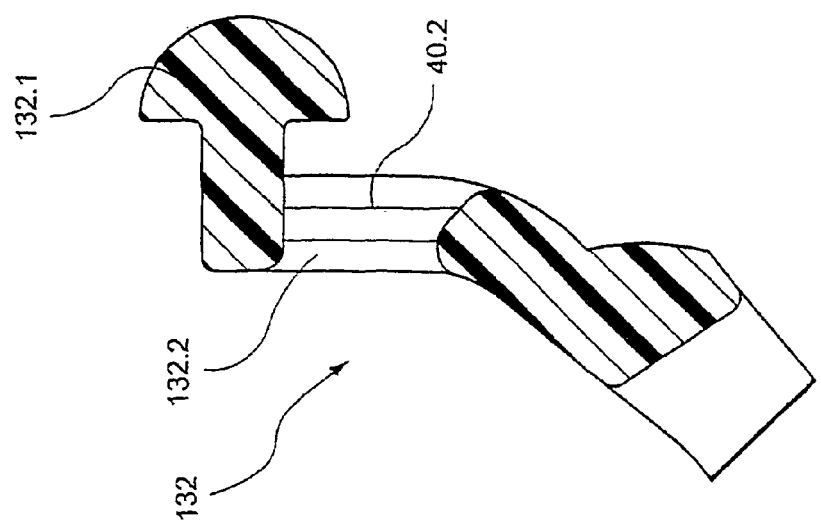
FIG. 18 illustrates a cross section showing detail Z of FIG. 14.
Figure 21:
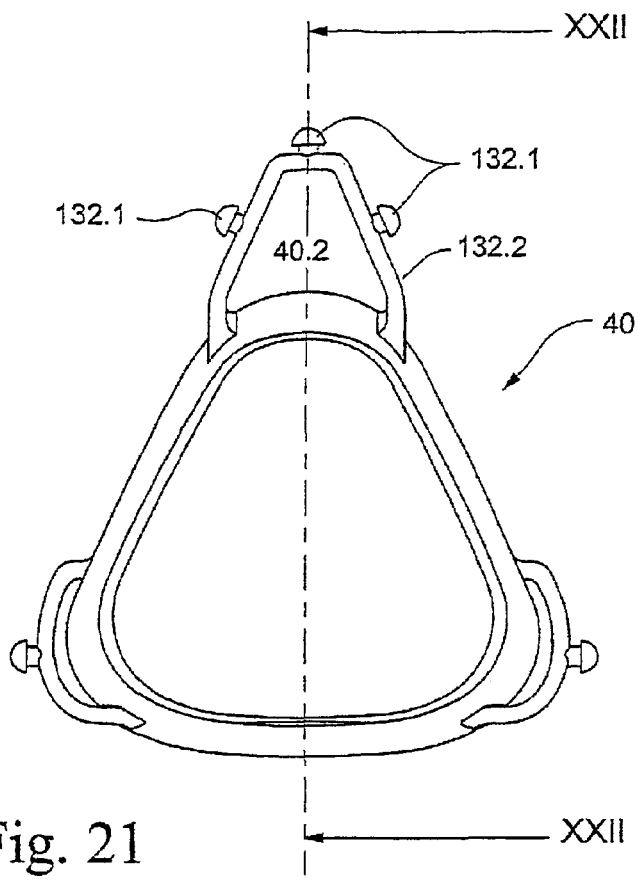
FIG. 21 illustrates a front elevation of a five point frame as used in the mask assembly of FIGS. 10 and 11.
Figures 22, 23:
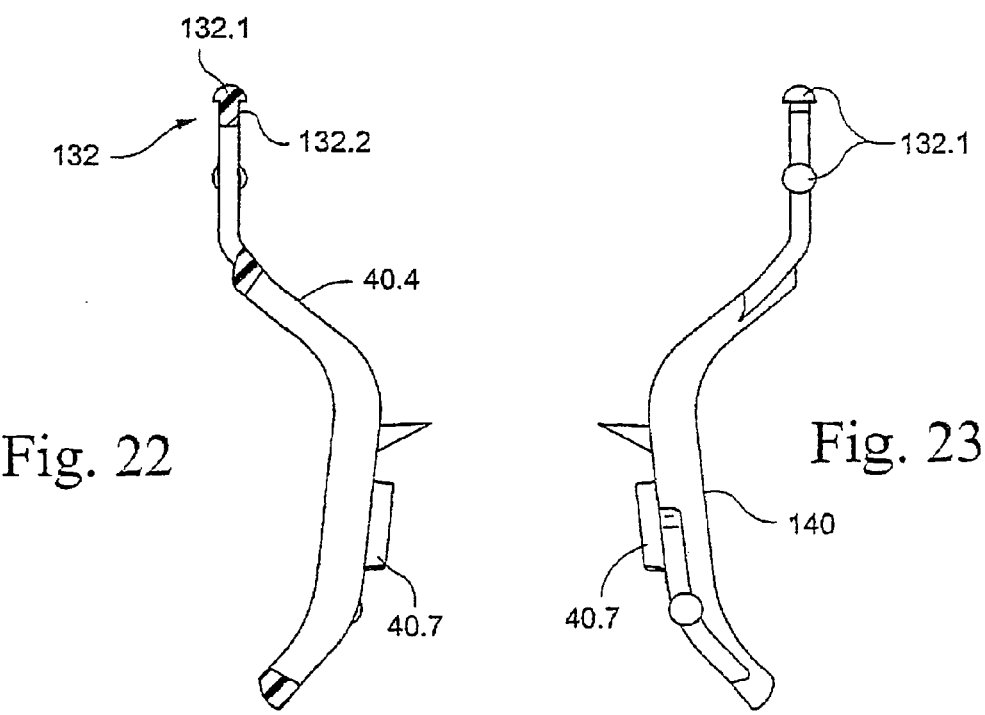
FIG. 22 illustrates a cross section through lines XXIII-XXIII the frame of FIG. 21.
FIG. 23 illustrates a left side elevation of the frame of FIG. 21.
Figure 24:
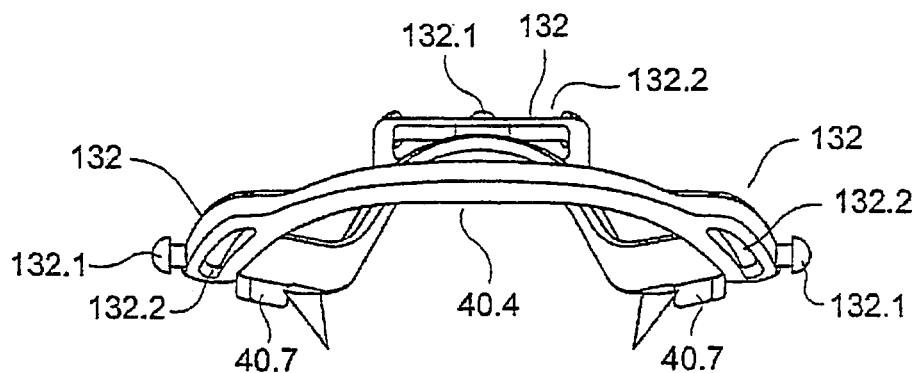
FIG. 24 illustrates an underneath view of the frame of FIG. 21.
Figure 25:
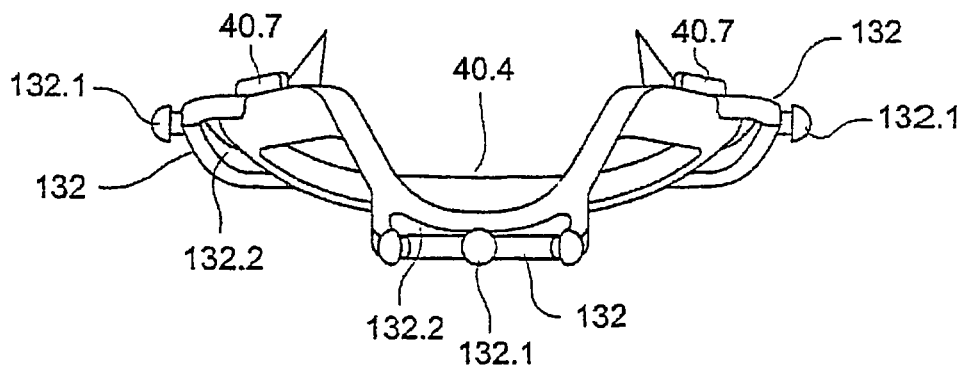
FIG. 25 illustrates a plan view of the frame of FIG. 21.
Figure 26:
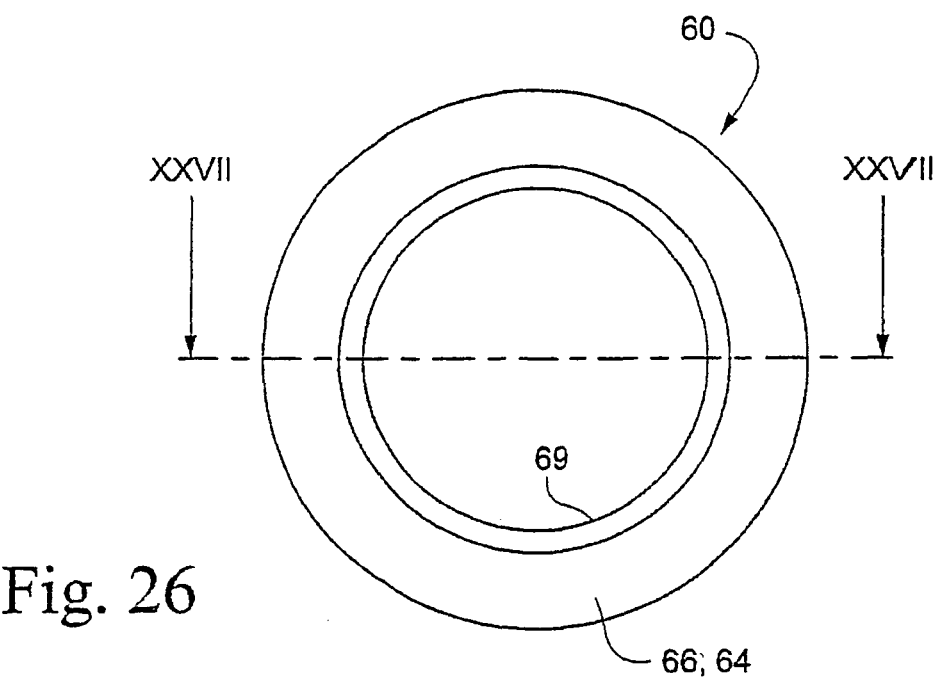
FIG. 26 illustrates a front elevation of a retaining ring.

FIG. 18 shows a detailed view of the mushroom headed spigot 132.1 of an anchor point 132 in cross-section from FIG. 14. In use, a patient selects the appropriate button hole 20.4 of the headgear 20 and then passes it through the apertures 40.1, 40.2 or 40.3 and over a mushroom headed spigot 132.1 on the frame 40 to set the headgear straps at the appropriate length.

The frame 40 has rearwardly projecting ribs 40.7, in the vicinity of the two lower anchor point 132, near to the base of the frame 40. The ribs 40.7 are sized and shaped so as to be received into the elongated recesses 30.75 on the shell/cushions 30 and 130.

The frame 40 provides an indent 40.4 which also extends away from the face of the patient as is illustrated in FIGS. 14 and 15. This indent 40.4 helps to provide space for the nasal bridge section of the shell/cushion 30 or 130, without exerting a pressure point onto the patient's nasal bridge.

As is illustrated in FIGS. 10, 11 and 21 to 25 is another frame 140 which is similar to the frame 40 of FIGS. 14 and 15 and like parts have been like numbered. The difference between the frame 40 and the frame 140 is that the frame 140 provides up to five anchor points 132.

The upper anchor point 132 includes a three sided frame member 132.2, and on each side of the frame member 132.2 is located, at a generally central location a mushroom headed spigot 132.1.

The frame 140 can thus be used with the headgear 20 described above which provides three ends of straps 20.1 and 20.2, or it can be used with a modified form of headgear (not illustrated) with five straps.

As an alternative (not illustrated), the frame 140 may also provide four anchor points 132 and be used with a modified form of headgear (not illustrated) with four straps.

Preferably each of three straps that can be used with the upper anchor point 132 will be threaded through the aperture 40.2, whereby the straight sided nature of the three sides will interact with a respective mushroom headed spigot 132.1 to firmly secure the ends of the straps thereto.

Illustrated in FIGS. 69 to 78 is a first piece 240 of a frame for use with the shell/cushion 330 of FIGS. 109 to 117, and 122 and 123. The piece 240 is the outward facing portion of the frame once assembled.

Illustrated FIGS. 79 to 88 is a second piece 340 of the frame for use with the shell/cushion 330 of FIGS. 109 to 117, 122 and 123. The piece 340 is the inward facing portion of the frame once assembled.

The pieces 240 and 340 are of similar overall shape to the frames 40 and 140, and like parts are like numbered.

Figure 72:
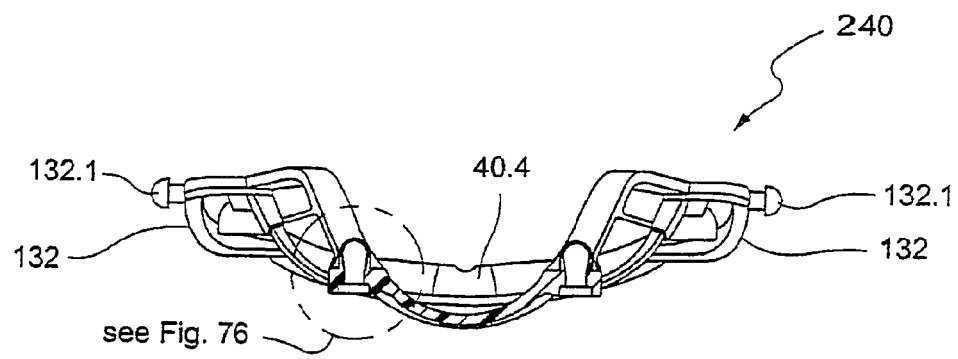
FIG. 72 illustrates a cross section through the line LXXII-LXXII of the frame of FIG. 69.
Figure 73:
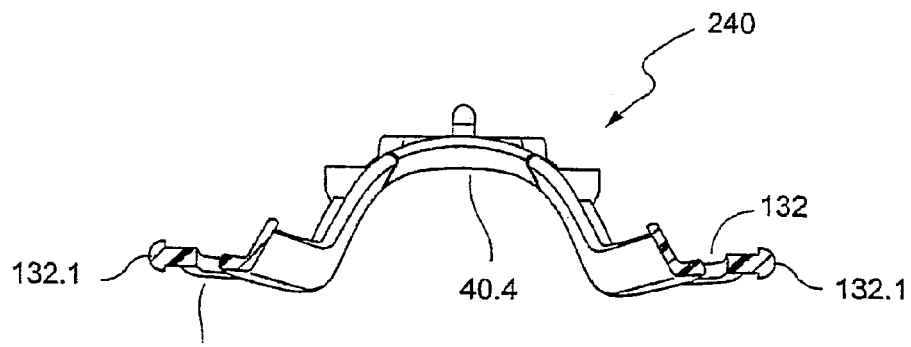
FIG. 73 illustrates a cross section through the line LXXIII-LXXIII of the frame of FIG. 69.
Figure 74:
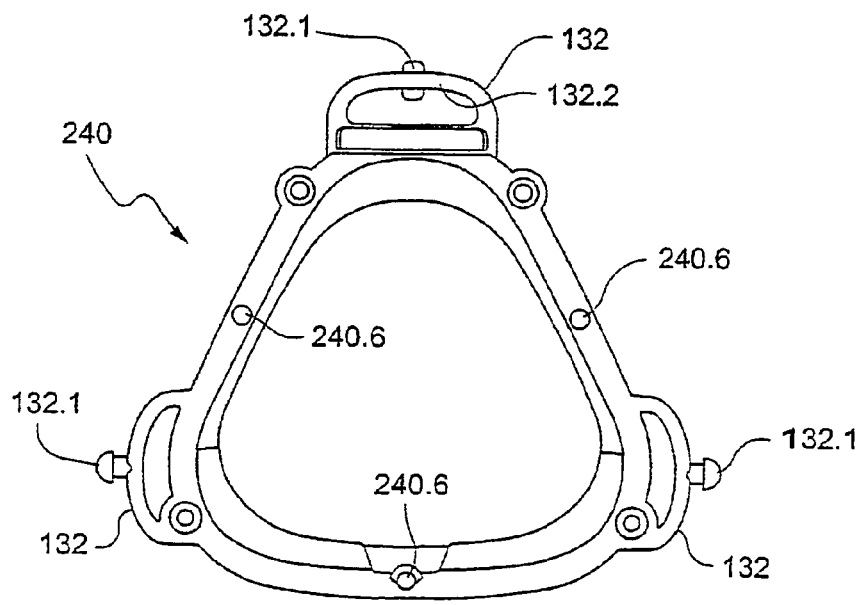
FIG. 74 illustrates a rear elevation of the frame of FIG. 69.
Figure 76:
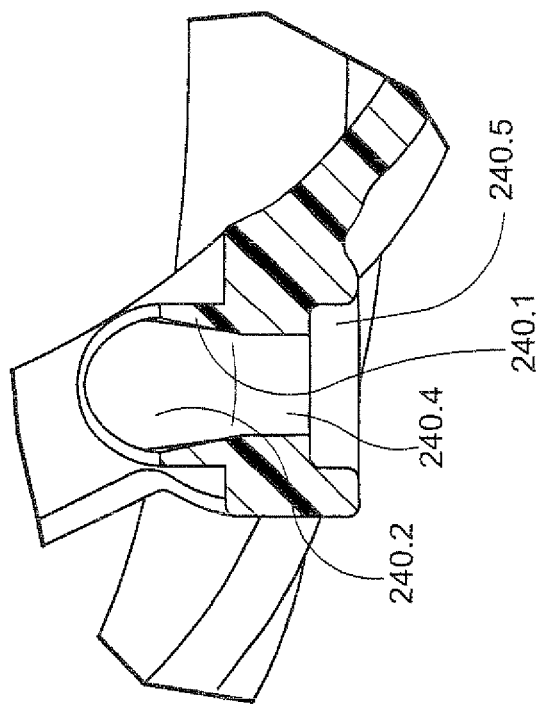
FIG. 76 illustrates in detail a portion from the cross section of FIG. 72.
Figure 75:
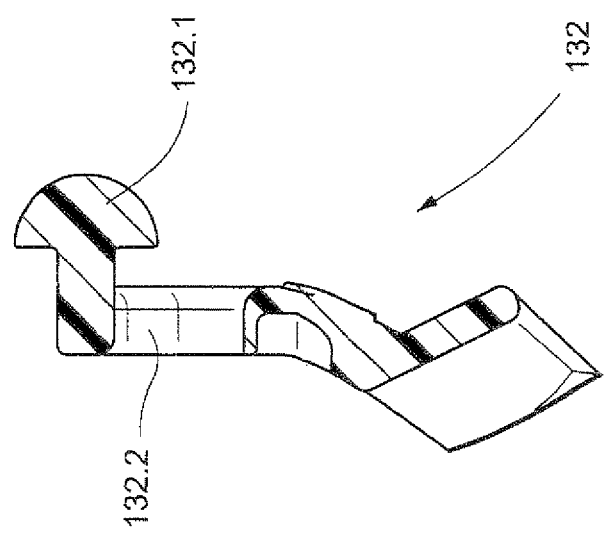
FIG. 75 illustrates in detail a portion from the cross section of FIG. 71.
Figure 78:
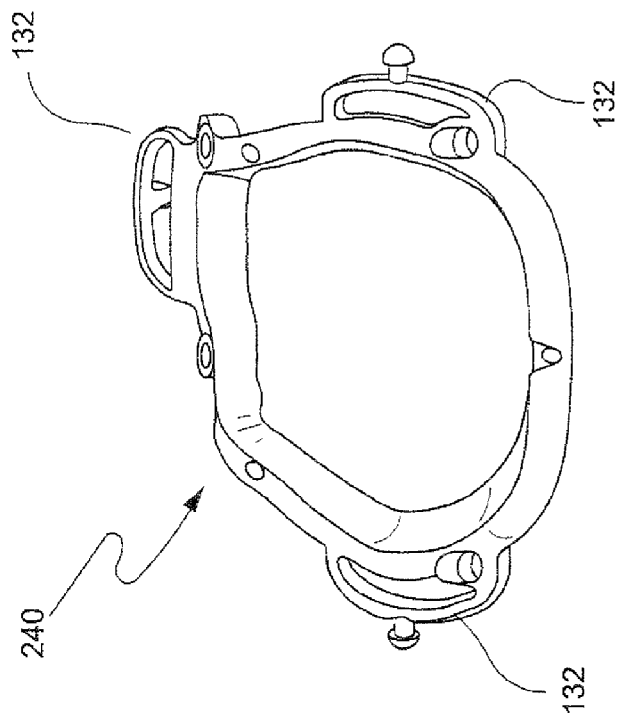
FIG. 78 illustrates a left side perspective view of the frame of FIG. 69.
Figure 77:
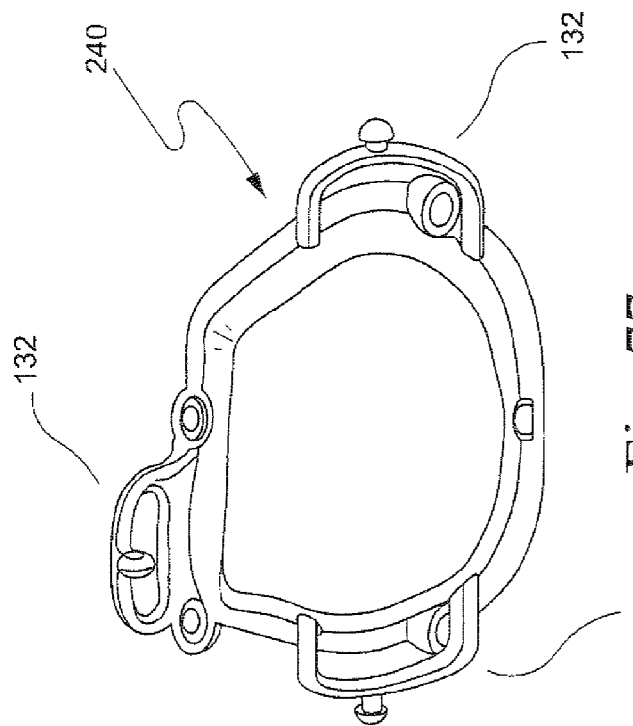
FIG. 77 illustrates a right side perspective view of the frame of FIG. 69.
Figure 80:
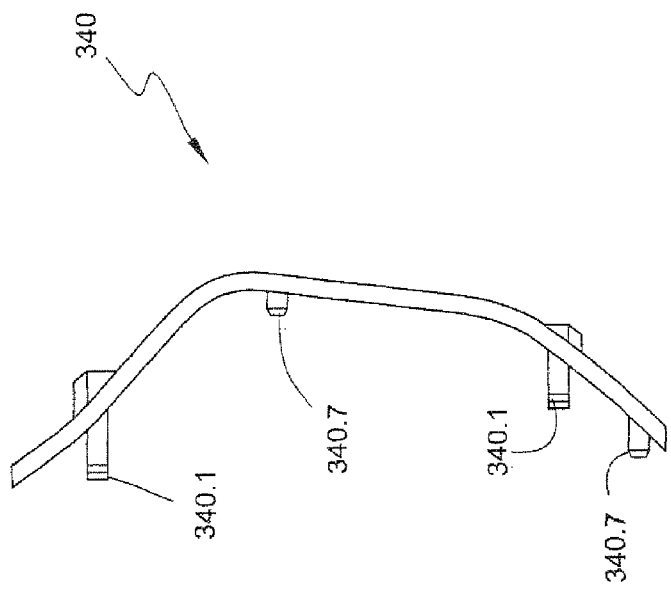
FIG. 80 illustrates a right side elevation of the frame of FIG. 79.
Figure 79:
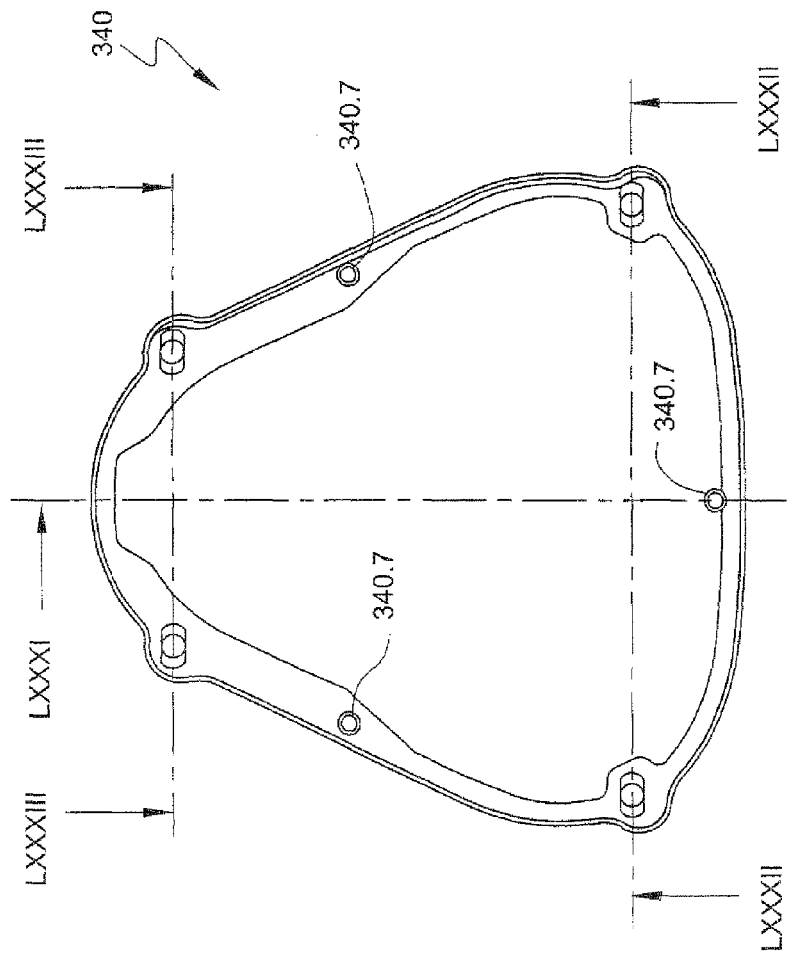
FIG. 79 illustrates a front elevation of a clip for use with the frame of FIG. 69.
Figure 85:
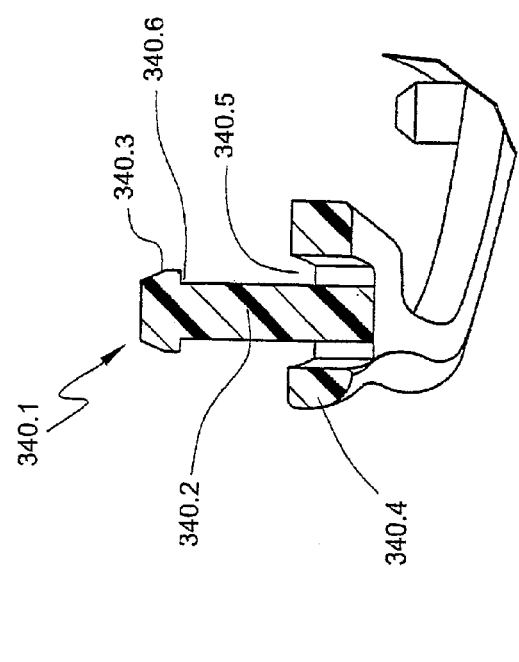
FIG. 85 illustrates in detail a portion from the cross section of FIG. 82.
Figure 86:
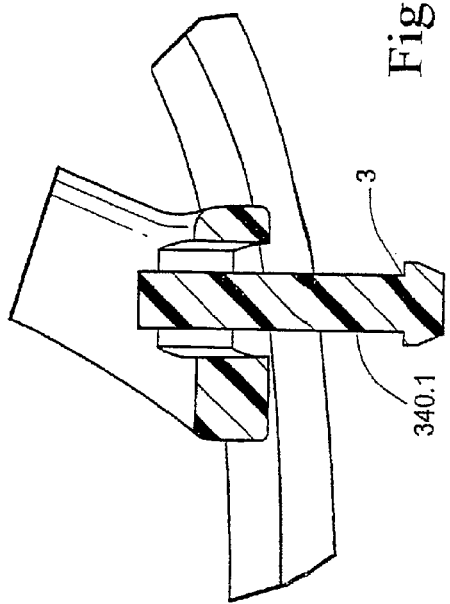
FIG. 86 illustrates in detail a portion from the cross section of FIG. 83.
Figure 84:
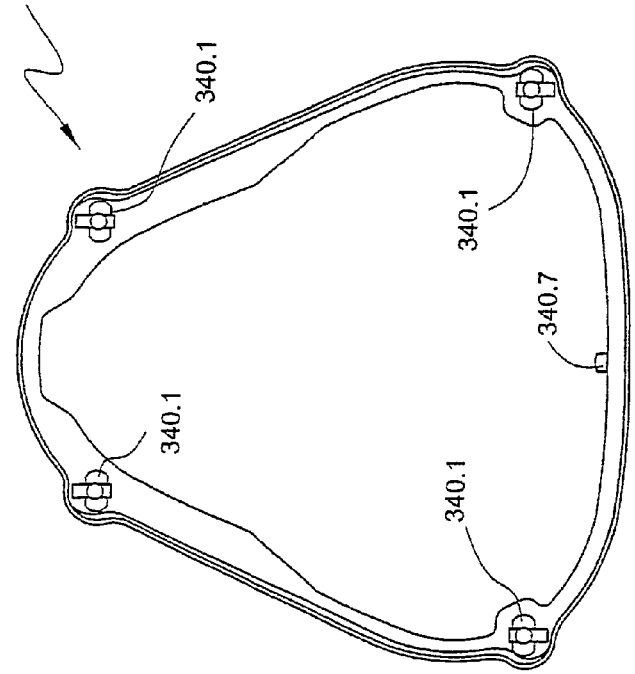
FIG. 84 illustrates a rear elevation of the frame of FIG. 79.
Figure 88:
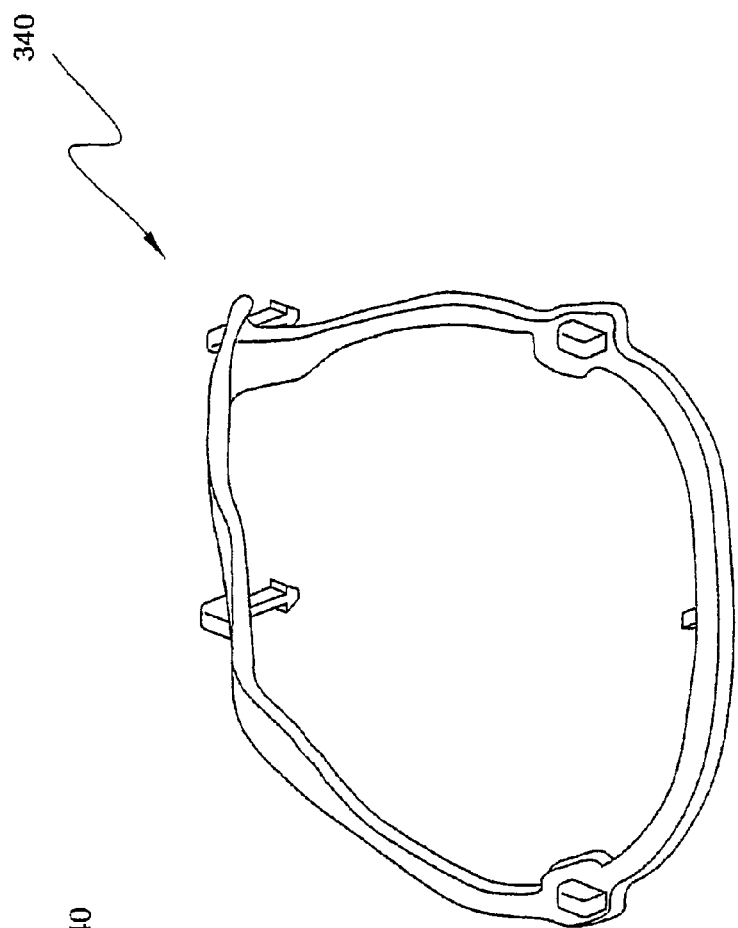
FIG. 88 illustrates a left side perspective view of the frame of FIG. 79.
Figure 87:
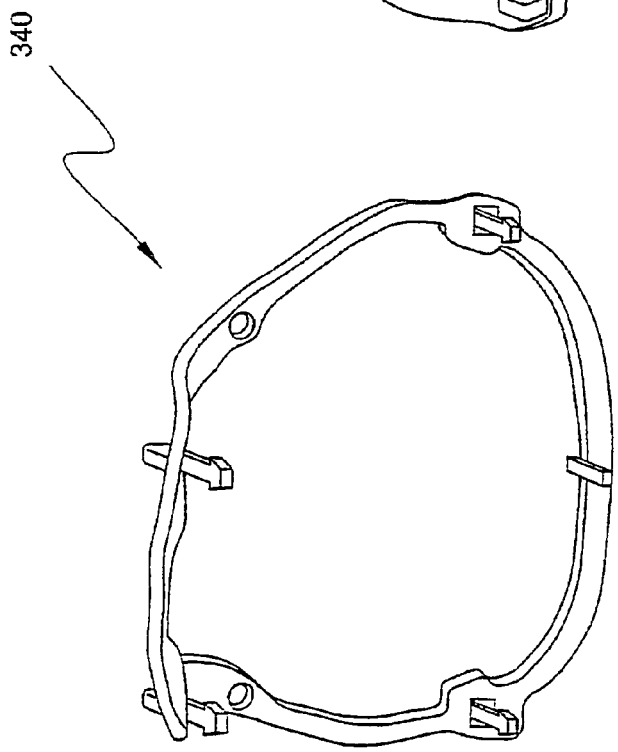
FIG. 87 illustrates a right side perspective view of the frame of FIG. 79.
Figure 89:
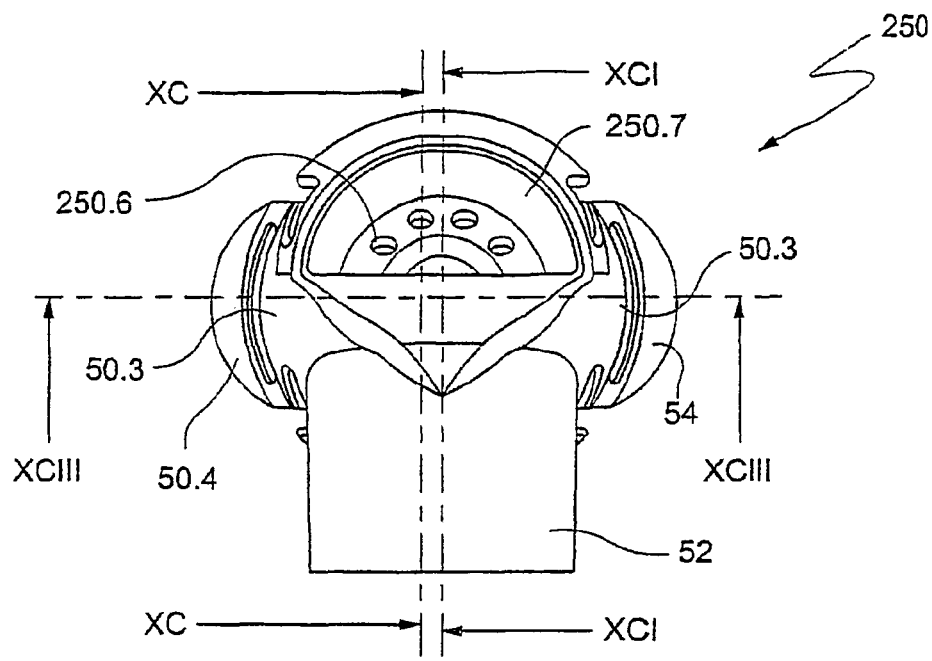
FIG. 89 illustrates a front view of an elbow according to yet another embodiment of the present invention.

The piece 240 receives and secures the piece 340 therein, by means of four large diameter apertures 240.1, which as can be seen most clearly from FIGS. 72 and 76 have a tapered entry way 240.2 formed in a rearwardly extending cylindrical wall 240.21. In alternative embodiments, there may be between one and five large diameter apertures 240.1. The tapered entry way 240.1 leads to a constricted aperture 240.4 and a larger diameter recess 240.3 on the other side of constructed aperture to the entry way 240.2. The larger diameter recess 240.3 has at its base a shoulder 240.5.

The apertures 240.1 receive rivets 340.1 on the piece 340. As can be seen from FIGS. 82, 83, 85 and 86 and the rivets 340.1 have a tapered shank 340.2 and a tapered mushroom head 340.3, the underside of which has a shoulder 340.6. Surrounding the base of the shank 340.2 is a housing 340.4 which has an annular recess 340.5 between the base of the shank 340.2 and the housing 340.4. The tapered end of the mushroom head 340.3 allows the head 340.3 to push through the entry way 240.2 and the aperture 240.4, and once through, shoulders 340.6 and 240.3 will be adjacent each other preventing the withdrawal of the rivet 340.1 from the aperture 240.1.

The piece 240 includes three blind holes 240.6 into which will be received respective straight sided spigots 340.7. In alternative embodiments there may be differing numbers of blind holes and respective straight sided spigots, for example a number of blind holes and respective spigots between one and seven.

Figure 126:
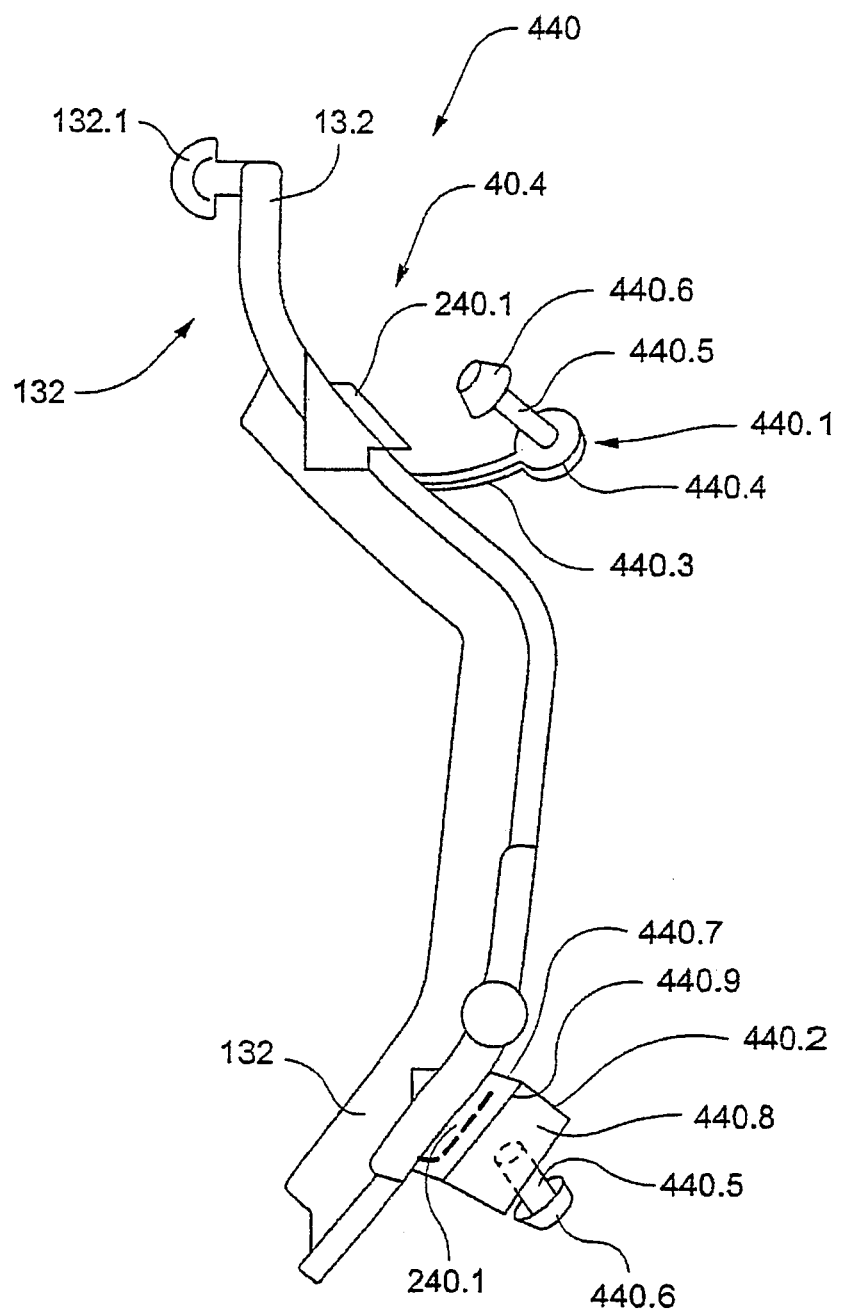

Illustrated in FIG. 126 is a frame 440 which is similar to the frame piece 240 of FIGS. 69 to 78. Accordingly, like parts have been like numbered. The frame 440 differs from the frame 240 in that the frame 440 does not require a second frame member to be used therewith. Instead the frame 440 has a rivet 440.1 located adjacent each aperture 240.1. The rivets 440.1, of which only one is illustrated for convenience, has a lanyard 440.3 which ties the rivet 440.1 to the frame 440. A bearing surface 440.4 is provided from which extend the rivet shaft 440.5 which terminates in a mushroom head 440.6. The rivet 440.1, including the lanyard 440.3 can be integrally moulded with the frame 440, and provides an easy means of assembly.

To assemble the rivet 440.1, the frame 440 is placed adjacent the flange 330.1 of the shell/cushion 330, then the rivet 440.1 is moved into position against the rear face of the flange 330.1 and pushed home so that the bearing surface 440.4 can sandwich or compress the flange 330.1 to the rear face of the frame 440.

For the sake of illustration the aperture 240.1 near the bottom of the frame 440 has a different rivet structure associated with it. The rivet 440.2 has relatively thin panel 440.7 which extend away from the frame 440. A second panel 440.8 is hinged by a hinge 440.9 to the panel 440.7. Extending away from the panel 440.8 is a rivet shaft 440.5 which terminates in a mushroom head 440.6, in much the same way as the rivet 440.1.

The distance between the hinge 440.9 and the frame 440 (the height of the panel 440.7) can be sized to provide either a loose or snug fit around the flange 330.1, or if desired sized to provide as much compression of the flange 330.1 as possible. By positioning the flange 330.1 adjacent the aperture 240.1 and folding the panel 440.8 over so that the head 440.6 of the rivet is pushed home into the aperture 240.1, the rivet 440.2 will hold the flange 330.1 in place relative to the frame 440.

The frame 40, the pieces 240 and 340, and the frame 440 can be moulded from any appropriate material such as polycarbonate.

§5 Connection Piece or Elbow

As is illustrated in FIGS. 1, 7, 9, 11, 12, 62 to 66, and most particularly in FIGS. 30 to 37, the elbow 50 has a distal end 52 which is adapted to engage, whether with or without a swivel or union 250.2 (see FIG. 1) with an air delivery conduit (not shown). The union 250.2 is illustrated in FIG. 1, but is optional. The manner by which the union 250.2 connects to the elbow 50, is that the internal cylindrical surface of the distal end 52 includes an annular groove 250.1 (see FIGS. 11, 32, 35A and 35B), which will receive an annular lip 250.3 on the swivel 250.2.

A proximal end 50.1 of the elbow 50 is adapted to engage with both a shell/cushion 30, 130, 230, 330 and a retaining ring 60 positioned within the aperture 30.3 of the shell/cushion. Two, circumferentially equi-spaced or diametrically opposed, tongues 50.3 extend away from the body of the elbow 50 near to the proximal end 50.1. Each tongue 50.3 has an arcuate undercut 50.2 which is located on an inwardly facing surface 50.4 of the tongue 50.3. The undercuts 50.2 engage with the retaining ring 60. Each finger 50.3 is located at diametrically opposite locations on the elbow 50, and are located on either side of the elbow 50 at the proximal end 50.1 thereof.

At the ends of the tongues 50.3 there are included finger grips 54. The finger grips 54 enable a user to pull the tongues 50.3 in a radially outward direction relative to the proximal end 50.1, thereby permitting the undercuts 50.2 to clear the rim of retaining ring 60. This then allows the elbow 50 to be disassembled from the mask assembly 10, whereby it can be removed for cleaning. Located near to the finger grips are two undercuts to removably engage with the retaining ring.

The inside surfaces of the finger grips 54 include a tapered entry way 50.7, whereby when the proximal end 50.1 is pushed into contact with a rim of the retaining ring, the finger grips 54, and thus the undercuts 50.2 are pushed away from the rim of the retaining ring 60, thereby allowing the undercuts to push past the rim, and biased radially inwardly back into engagement, preventing the separation of the proximal end 50.1 from the retaining ring 60.

An exemplary shape and dimensions of the elbow 50 are indicated in the FIGS. 30 to 37.

Illustrated in FIG. 10, and FIGS. 38 to 46 is another elbow 150. The elbow 150 is similar to the elbow 50 described above and like parts have been like numbered. However, the elbow 150 differs from the elbow 50 in that the elbow 150 does not include the moveable tongues 50.3 and finger grips 54 which are included on the elbow 50. Instead, the elbow 50 has six discreet undercuts 50.2 equi-spaced the inner edge 50.5 on the skirt 50.6 which surrounds the proximal end 50.1. In this way the elbow 150 is adapted to be not removable from the shell/cushion 30, 130, 230, 330 and is thus useful for a disposable mask.

The undercuts 50.2 are formed adjacent the apertures 50.11 through the skirt 50.6. The apertures 50.11 are formed by that portion of the mould which forms the undercut 50.2, preventing molten plastic occupying that space. If desired more or less discrete undercuts 50.2 can be provided.

The inside surfaces of the skirt 50.6 include a tapered entry way 50.7, whereby when the proximal end 50.1 is pushed into contact with a rim of a retaining ring 60, the skirt 50.6, and thus the undercuts 50.2 are pushed away from the rim of the retaining ring 60, thereby allowing the undercuts 50.2 to push past the rim. The construction of the skirt 50.6 provides a radially inward bias forcing the undercut 50.2 back into engagement once past the rim, thereby preventing the separation of the proximal end 50.1 from the retaining ring 60.

The elbow can be moulded from any appropriate material such as polycarbonate or polypropylene.

The elbows 50 and 150 each include a port 56, such as Luer port, to enable access to the interior of the mask shell/cushion. For example, a pressure sensor may be attached. A polypropylene or silicone cap can be used to cover and seal the port when not in use.

The elbows 50 and 150 can be sized so as to freely rotated when mounted on the mask assembly 10. However, it is preferable that they are not able to freely rotate. Thus while rotation is allowed, when mounted onto a mask assembly 10, the inter-engagement of the components provides as a braking system. This means that, while adjustable, it tends to remain in the position in which it has been set. This is achieved through the combination of sizes shown and the use of one material on the elbow 50 and a different material on the shell/cushion with which it engages. This can be achieved through a slightly interfering fit between the ends of the undercuts 50.2 on the elbow 50 and shell/cushion 30, 130, 230, 330.

Preferably a suitable combination of materials and component configurations are selected so as to allow the user by hand to easily rotate the elbow to any desired position and once positioned, the elbow 50 or 150 will not move when experiencing the forces which are applied when the mask is attached to the gas conduit and it is in use by a sleeping patient. This allows the user to position the elbow 50 or 150 and thereby the gas conduit relative to the mask and face according to personal preference.

The elbows 50 and 150 and frame 40 are not directly connected, since their contact is through the shell/cushion 30, 130, 230, 330. Since the shell/cushion is constructed from a flexible material, movement of an air delivery conduit attached to the swivel elbow does not directly disrupt the seal of the shell/cushion. In this way, decoupling of drag forces from the air delivery conduit can be achieved.

Illustrated in FIGS. 89 to 98 is a connection piece or elbow 250 which is similar to the elbow 50 and like parts have been like numbered. The elbow 250 differs from the elbow 50 by two prominent features. The first is that the elbow 50 joined direct to a conduit to supply air via the distal end 52. Whereas the elbow 250 provides a groove 250.1 in its distal end 52, so as to receive in the distal end a 180° union 250.2 (see the union 250.2 of FIG. 122), which will be rotatably joined, by the annular lip 250.3 on the union 250.2 being received in the annular groove 250.1. This will provide a swivel connection between the conduit which will supply air, and the elbow 250.

Figure 91:
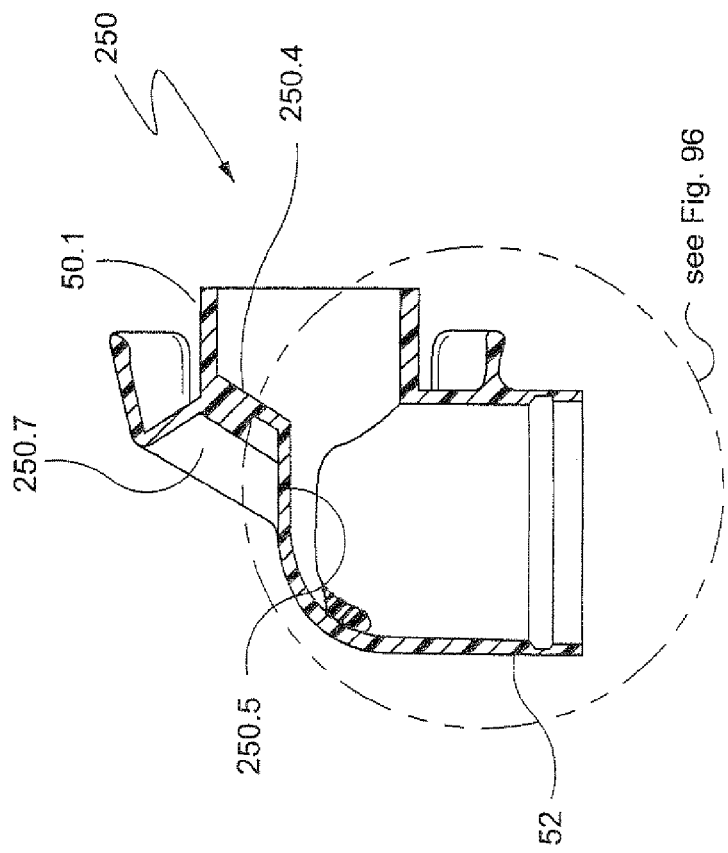
FIG. 91 illustrates a cross section through the line XCI-XCI of the elbow of FIG. 89.
Figure 93:
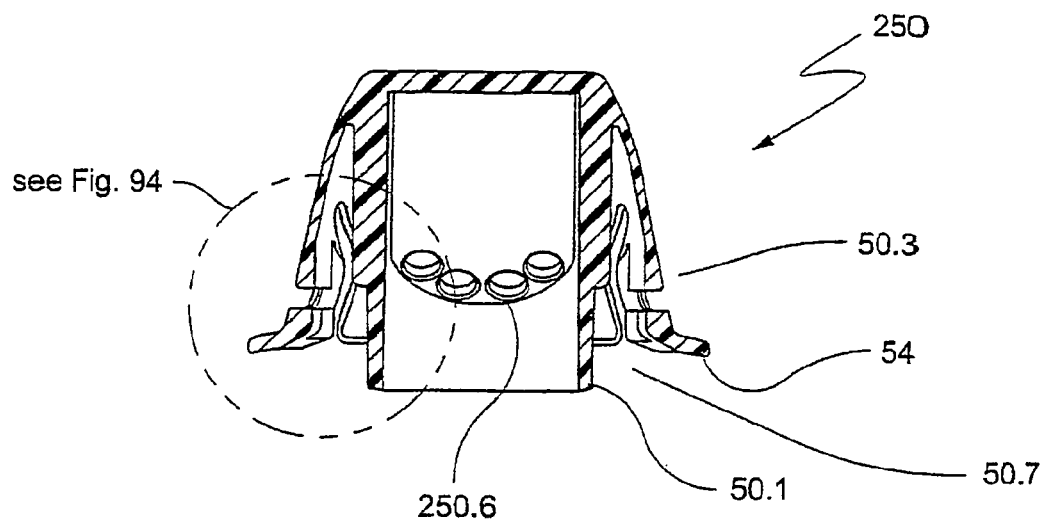
FIG. 93 illustrates a cross section through the line XCIII-XCIII of the elbow of FIG. 89.
Figure 94:
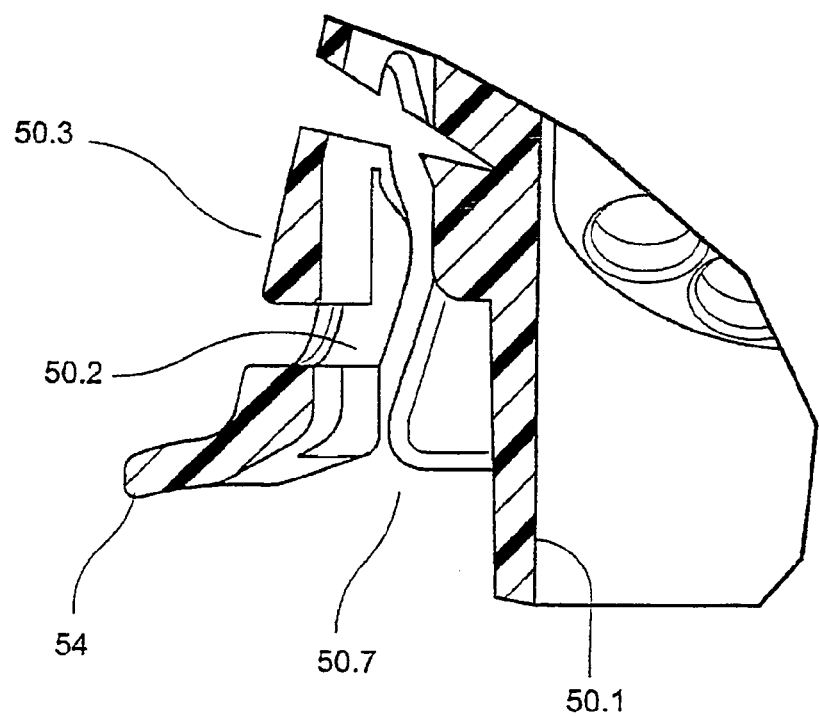
FIG. 94 illustrates in detail a portion of the cross section of FIG. 93.
Figure 96:
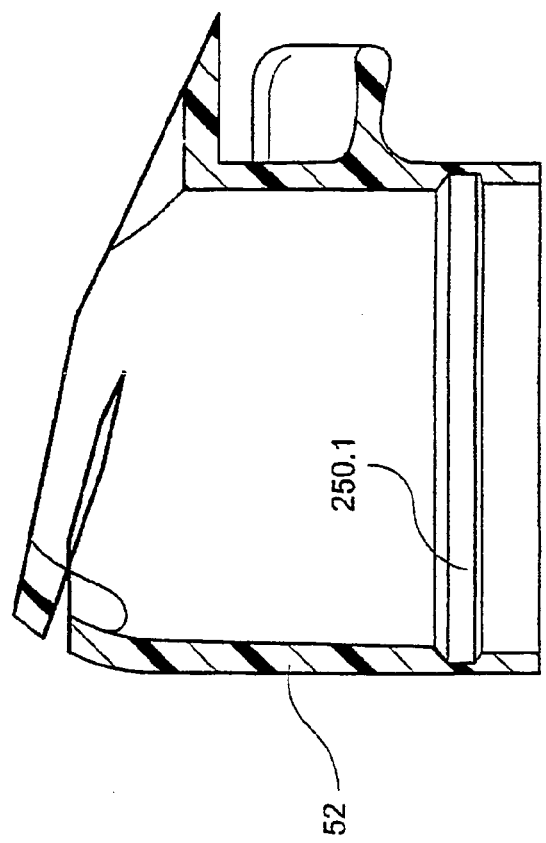
FIG. 96 illustrates in detail a portion of the cross section of FIG. 91.

The second feature of difference is that the elbow 250, as best seen in the cross section of FIG. 91, has vent wall 250.4 which extends away from the passage wall 250.5 which directs air flow out of the elbow 250.

Figure 90:
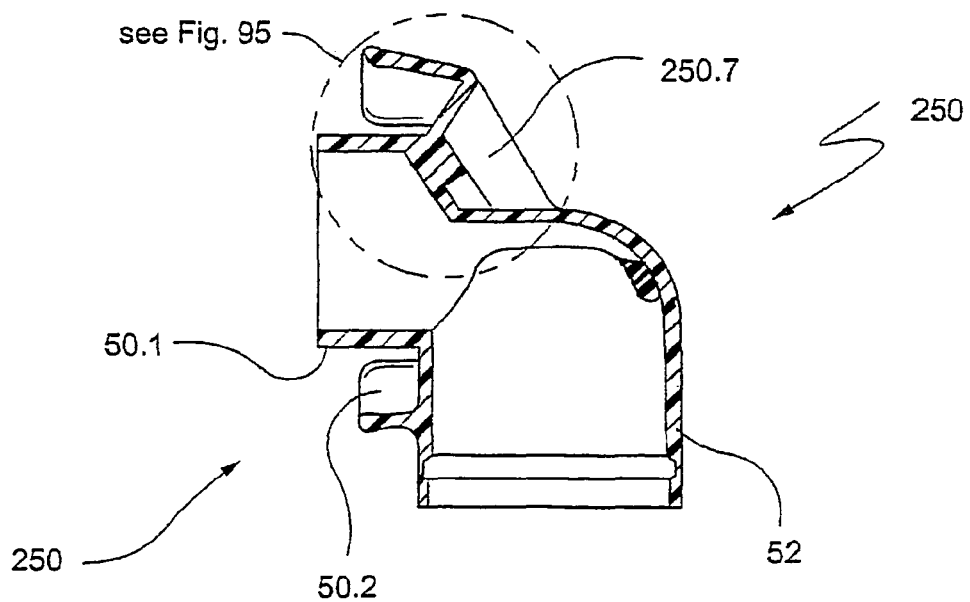
FIG. 90 illustrates a cross section through the line XC-XC of the elbow of FIG. 89.
Figure 92:
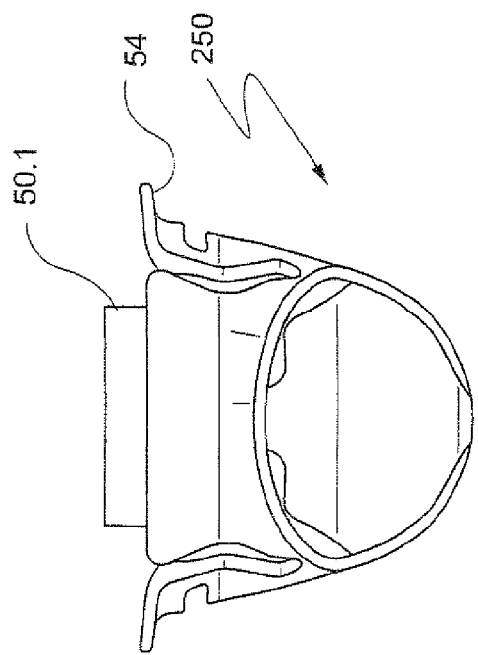
FIG. 92 illustrates a plan view of the elbow of FIG. 89.
Figure 95:
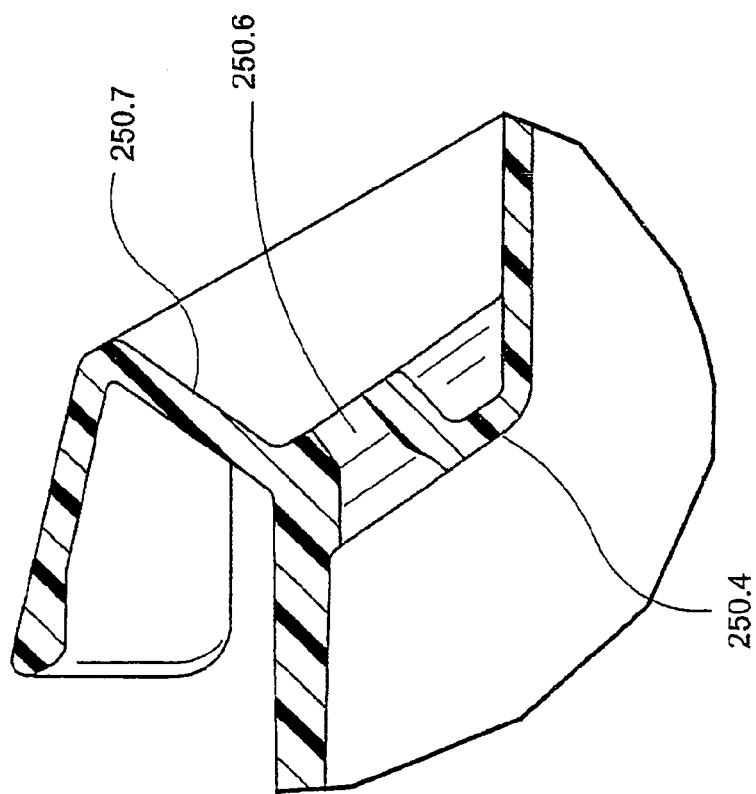
FIG. 95 illustrates in detail a portion of the cross section of FIG. 90.
Figure 97:
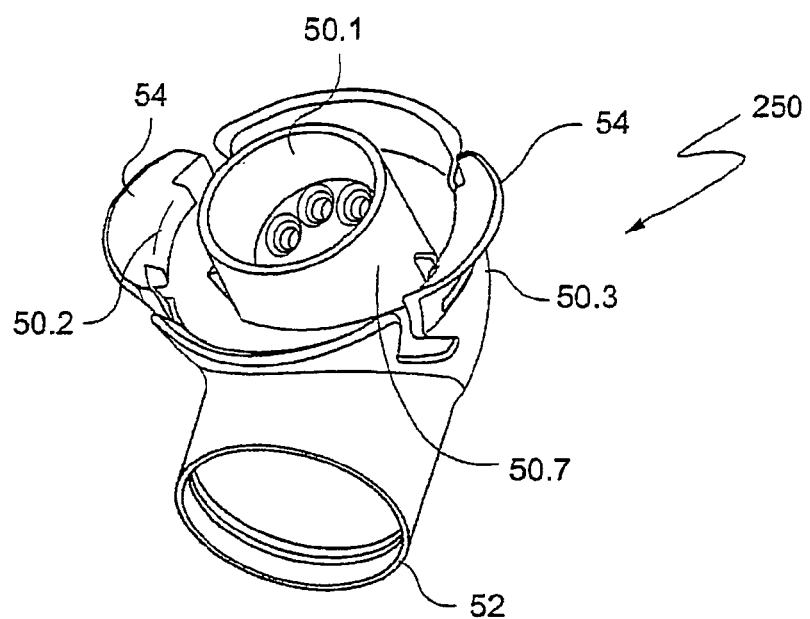
FIG. 97 illustrates a lower rear perspective of the elbow of FIG. 89.
Figure 98:
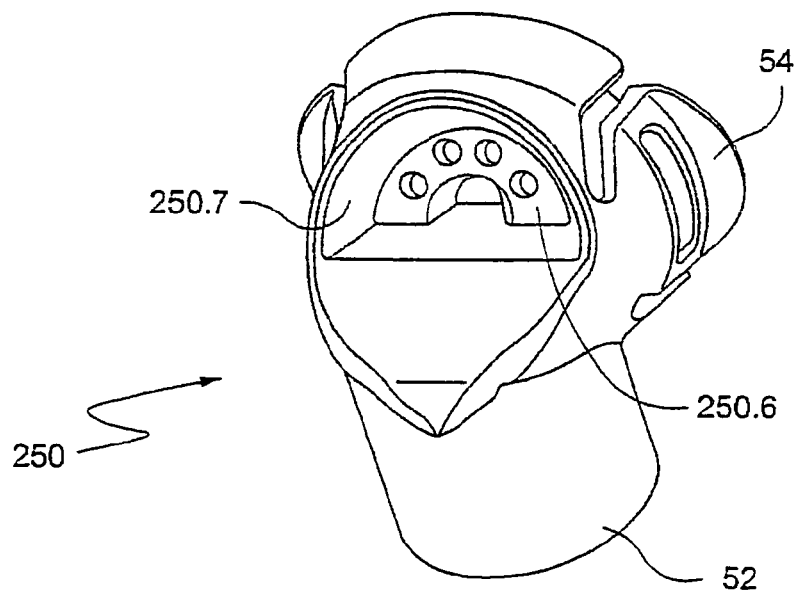
FIG. 98 illustrates an upper front perspective of the elbow of FIG. 89
Figure 99:
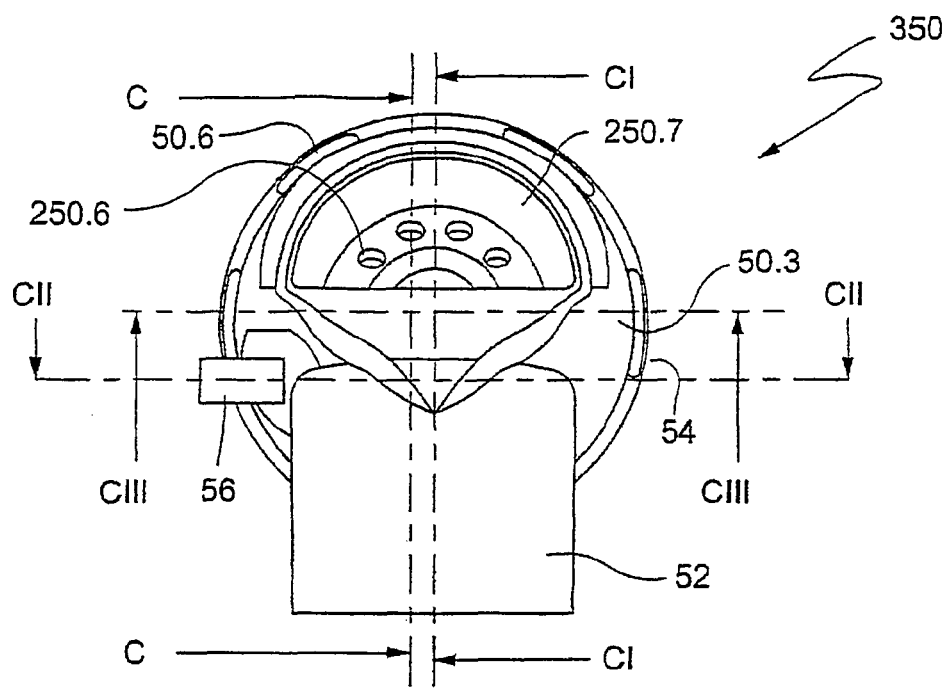
FIG. 99 illustrates a front view of a further elbow.
Figure 100:
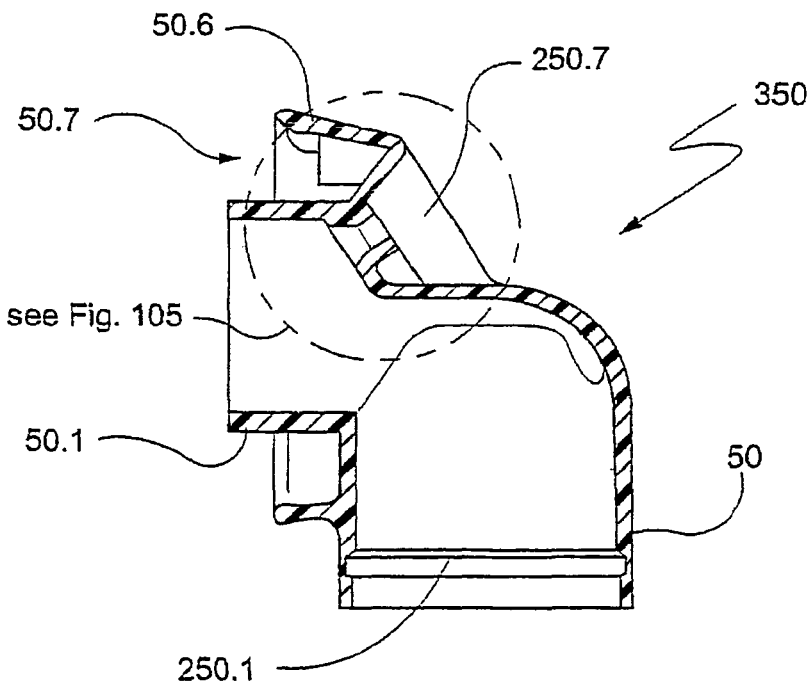
FIG. 100 illustrates a cross section through the line C-C of the elbow of FIG. 99.
Figure 101:
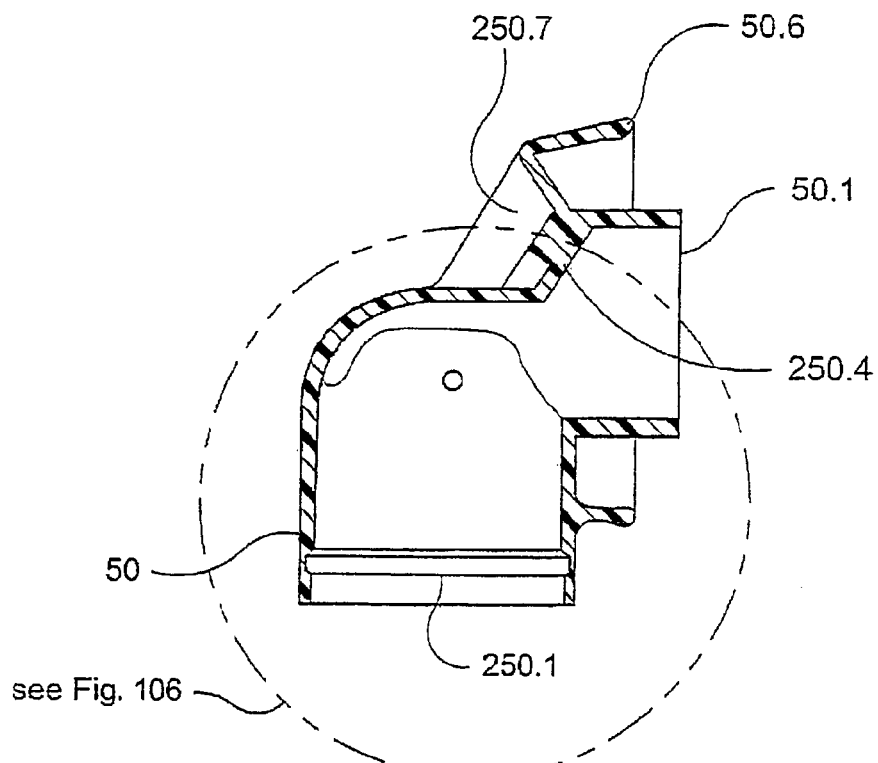
FIG. 101 illustrates a cross section through the line CI-CI of the elbow of FIG. 99.
Figure 102:
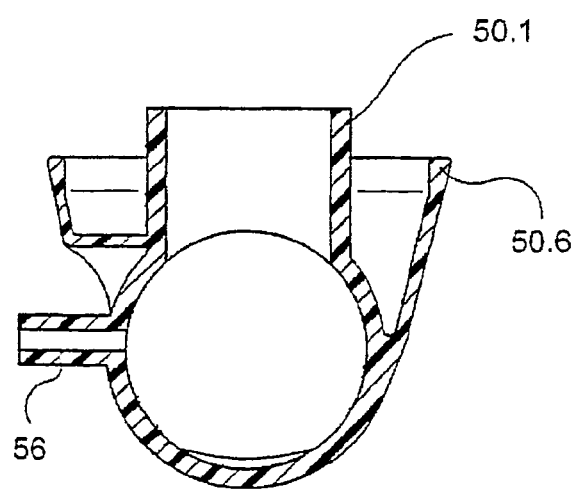
FIG. 102 illustrates a cross section through the line CII-CII of the elbow of FIG. 99.
Figure 103:
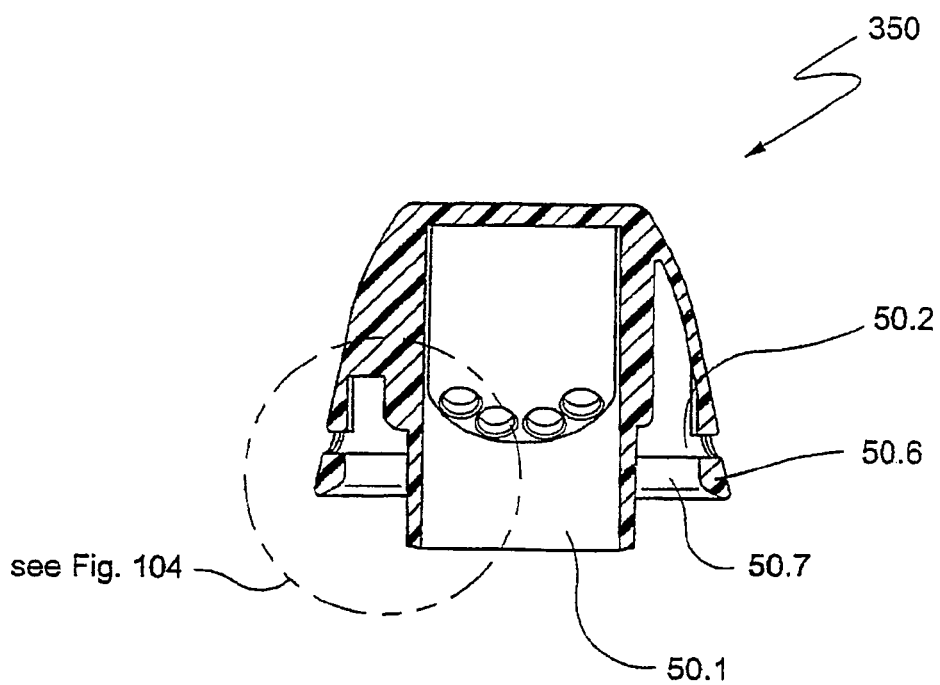
FIG. 103 illustrates a cross section through the line CIII-CIII of the elbow of FIG. 99.
Figure 104:
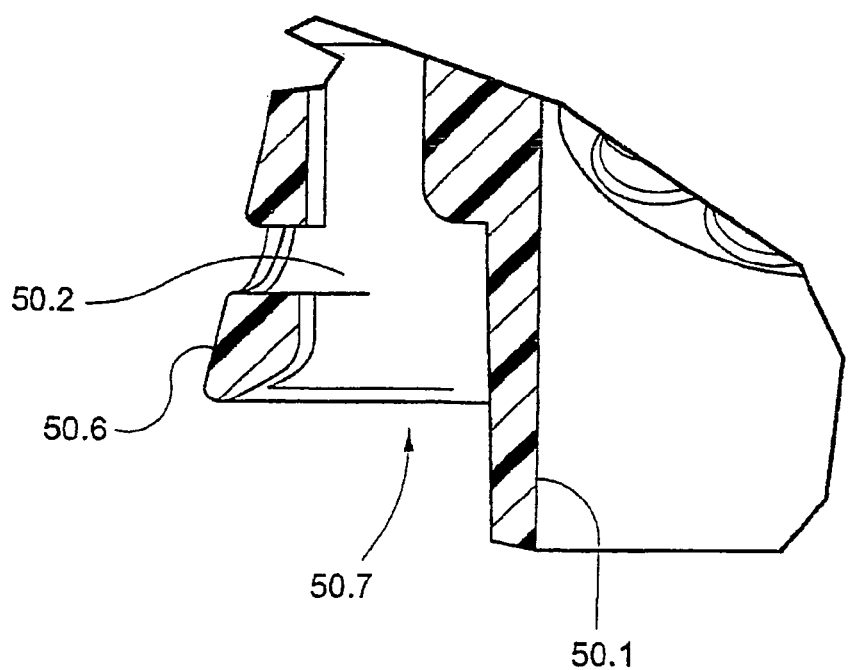
FIG. 104 illustrates in detail a portion of the cross section of FIG. 103.
Figure 105:
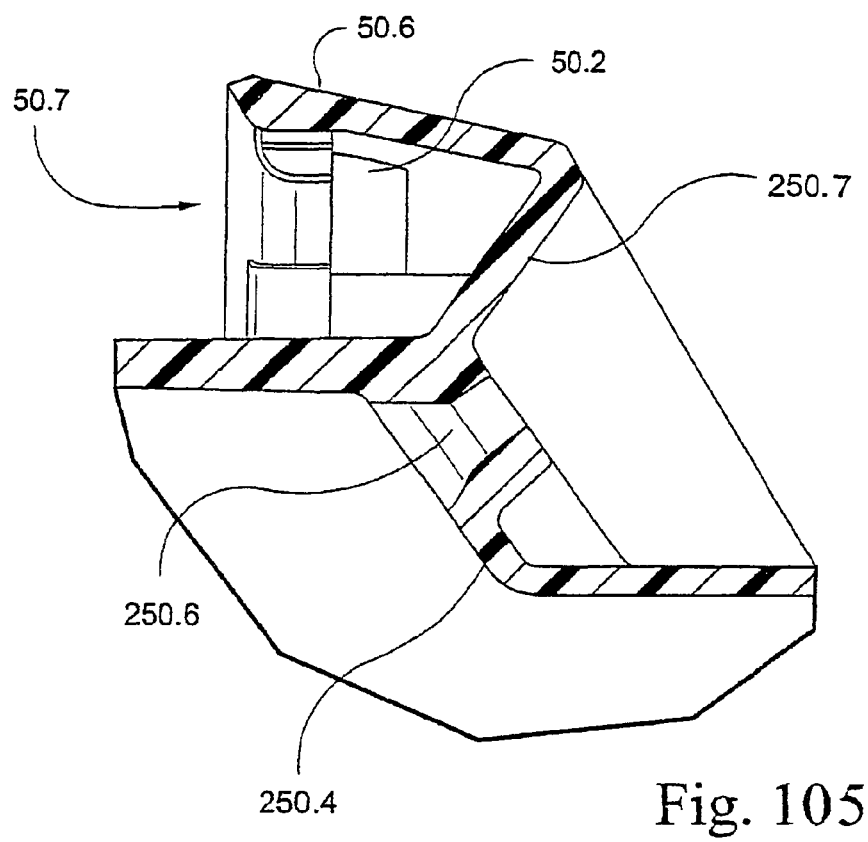
FIG. 105 illustrates in detail a portion of the cross section of FIG. 100.
Figure 106:
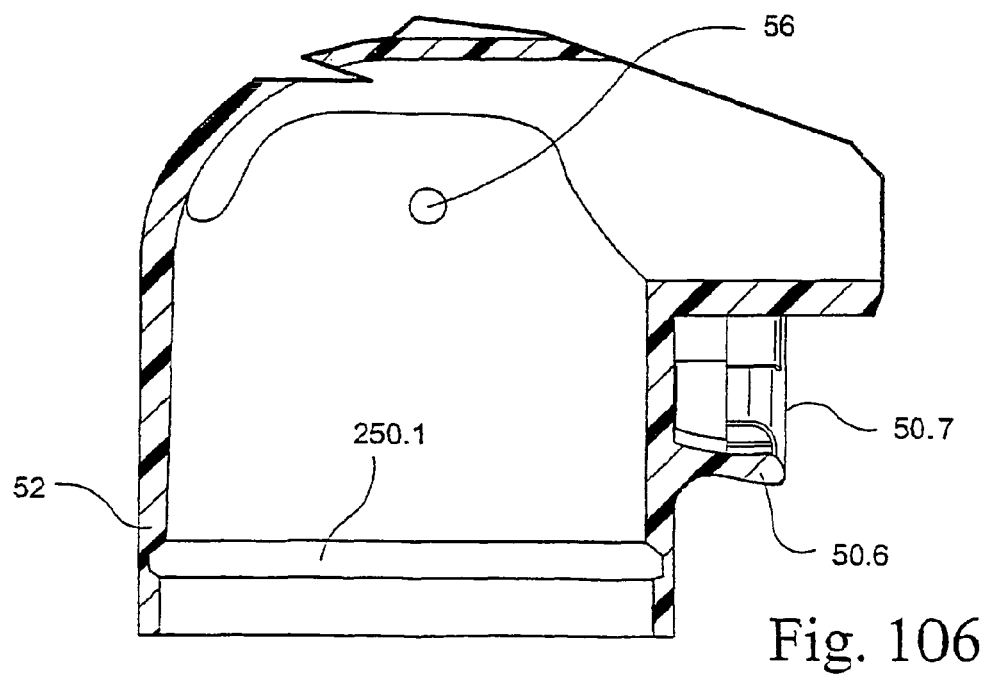
FIG. 106 illustrates in detail a portion of the cross section of FIG. 101.
Figure 107:
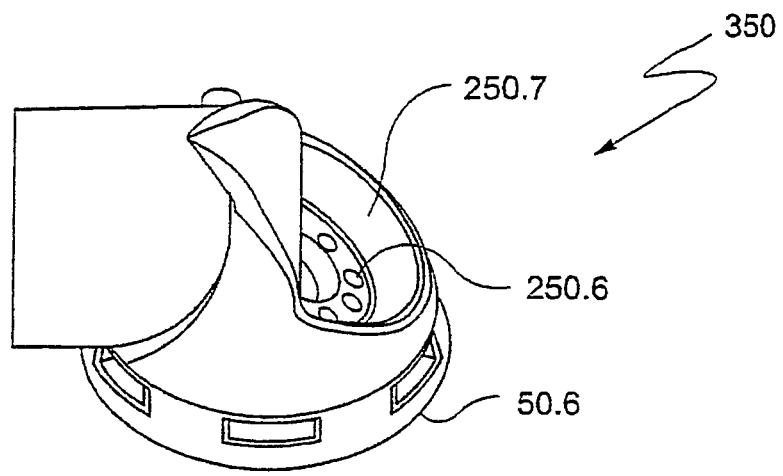
FIG. 107 illustrates a lower rear perspective of the elbow of FIG. 99.
Figure 108:
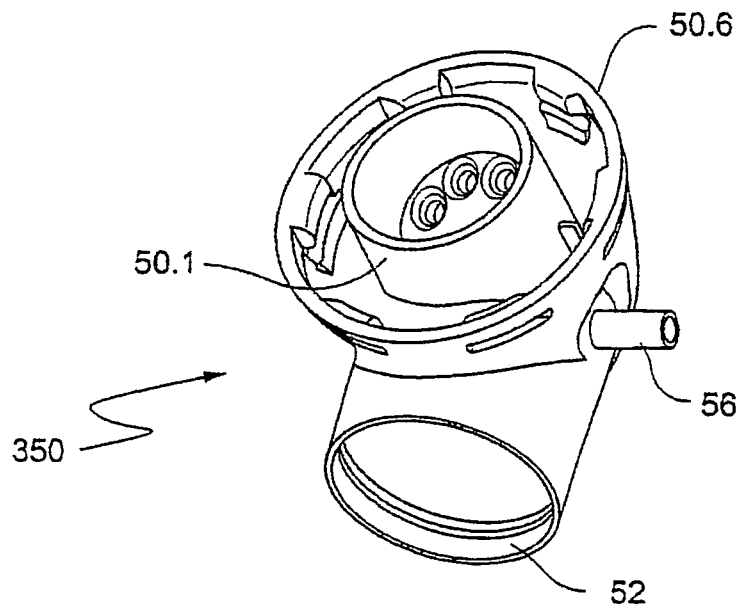
FIG. 108 illustrates an upper front perspective of the elbow of FIG. 99.
Figure 109:
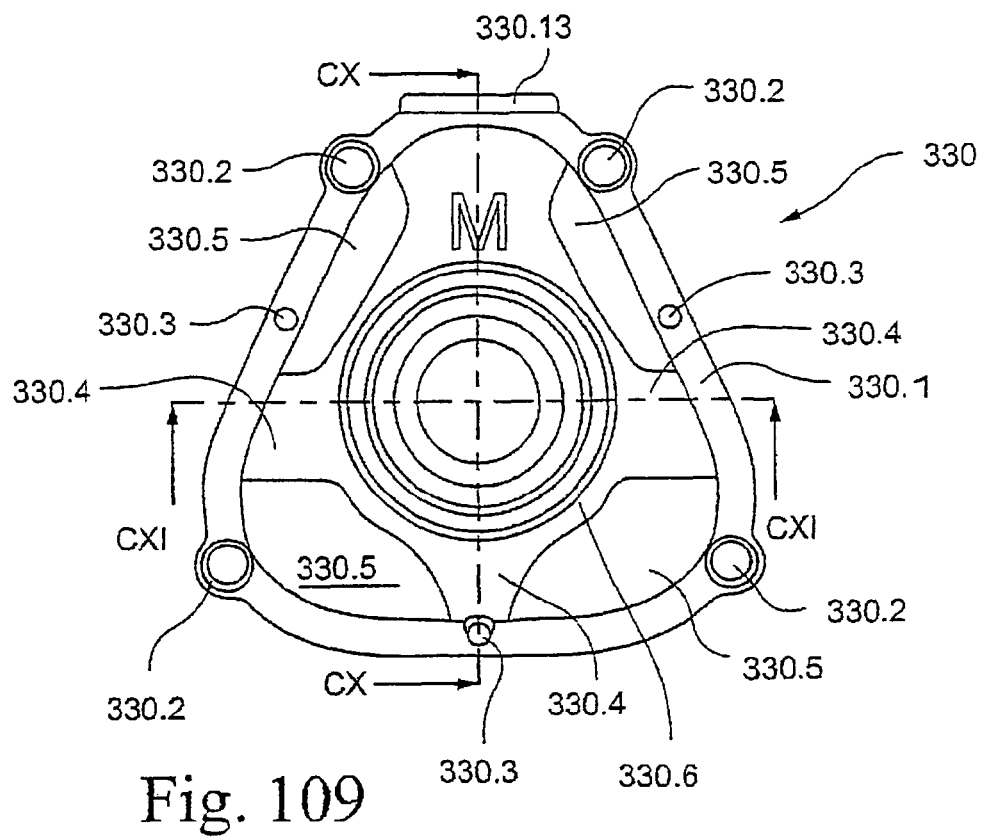
FIG. 109 illustrates a front view of another shell/cushion.
Figure 110:
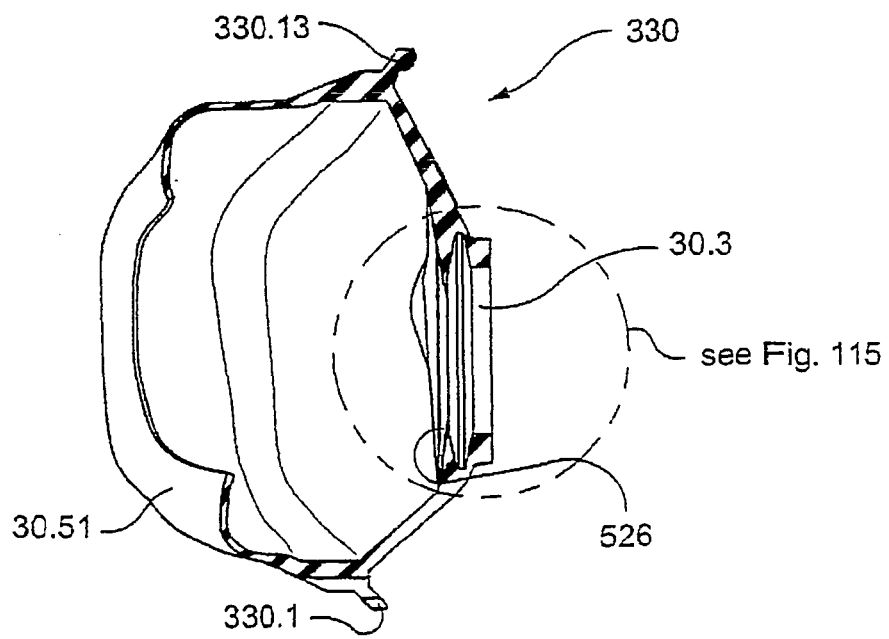
FIG. 110 illustrates a cross section through the line CX-CX of the shell/cushion of FIG. 109.
Figure 111:
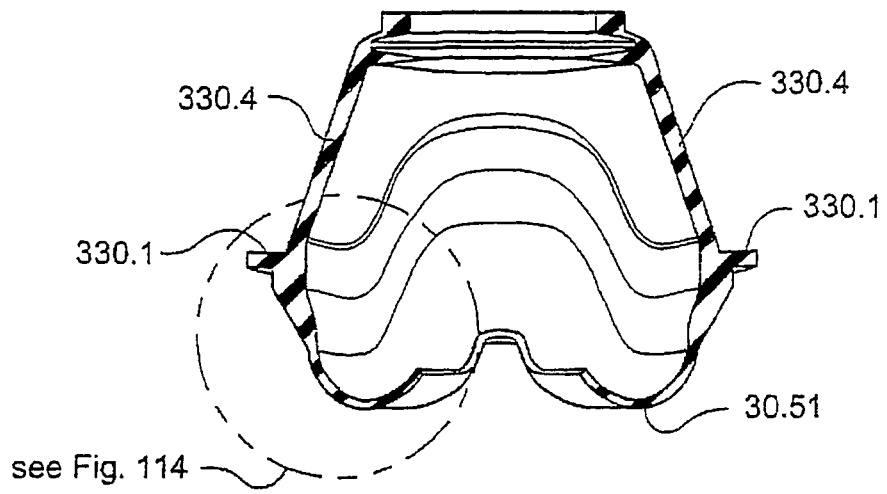
FIG. 111 illustrates a cross section through the line CXI-CXI of the shell/cushion of FIG. 109.
Figure 112:
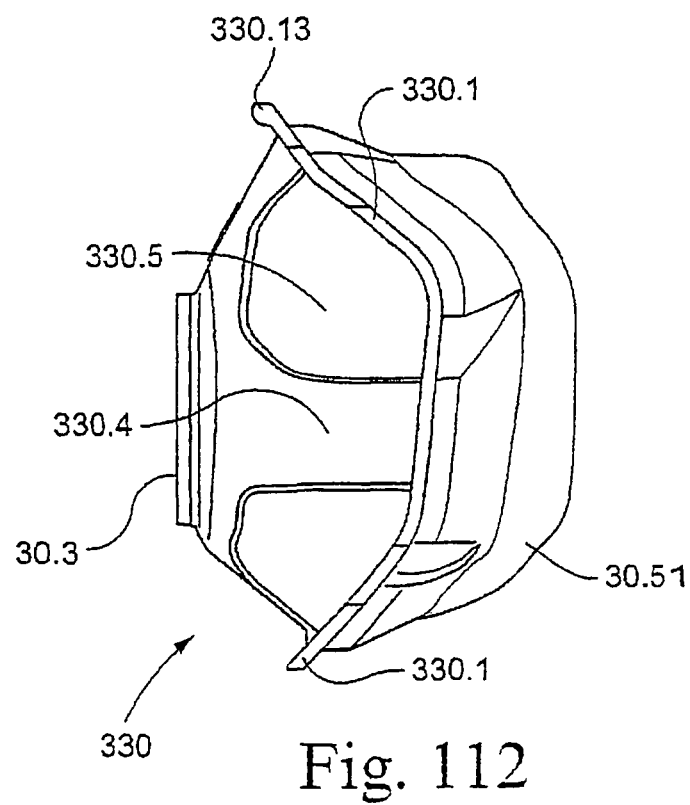
FIG. 112 illustrates a right side elevation of the shell/cushion of FIG. 109.
Figure 113:
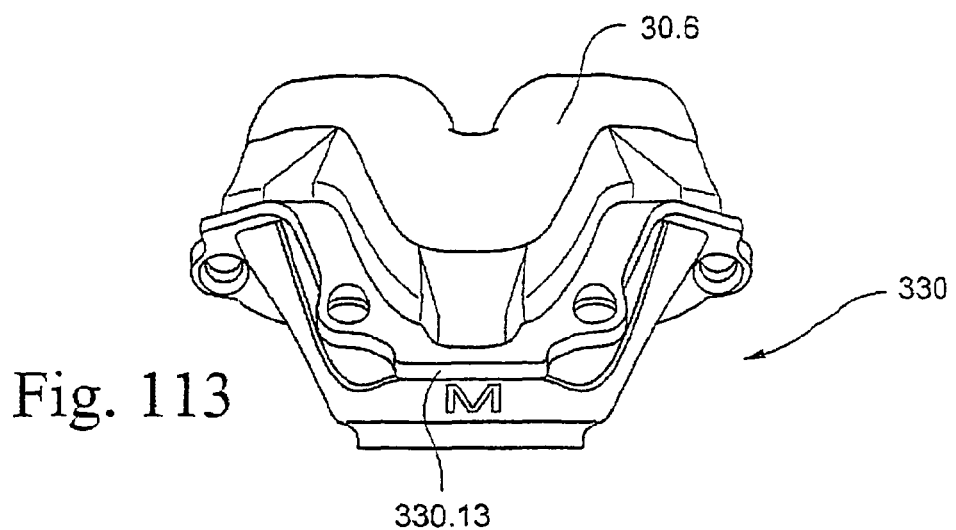
FIG. 113 illustrates a plan view of the shell/cushion of FIG. 109.

In the vent wall 250.4 is a series of four vent orifices 250.6, which are seen in more detail in cross section of FIG. 95. The orifices 250.6 lie at an angle to the outlet direction of air flowing out of the elbow 250. This angle is approximately 35°, or the complementary angle is 55° as is indicated in FIG. 90.

Extending away from the vent wall 250.4 is a divergent housing 250.7. By being divergent, any exhaled gases passing through the vent orifices 250.6 will be readily dispersed.

Illustrated in FIGS. 99 to 108, and 122 and 123, is a connection piece or elbow 350, which is similar to the elbow 150 and like parts have been like numbered. The elbow 350 also has the same first and second features or differences described above with respect to the elbows 50 and 250, and accordingly like parts have therewith have also been like numbered.

The elbow 350, being used to produce a mask assembly predominantly for single use and hospital use, includes a side located and directed Luer port 56. The side mounted Luer port 56 is particularly helpful for the situation where a tube is connected for monitoring purposes. This tube, by being mounted onto the Luer port 56 of the elbow 350, which if it is free to swivel, will mean that there need be no relative twisting of the monitoring tube relative to the supply conduit. This could not happen if the Luer port 56 were on the shell/cushion.

While the connection pieces or elbows 250 and 350 only have a 90° angle between the inlet at the distal end 52 and the outlet at the proximal end 50.1, it will be readily understood that the connection piece can be constructed with the vent wall 250.4, vent orifices 250.6, and divergent housing 250.7 with any appropriate angle between the inlet at the distal end 52 and the outlet at the proximal end 50.1. This angle can be 180°, whereby an in-line or union connection piece can be produced.

§6 Retaining Ring

A retaining ring 60 for use with the mask assembly 10 is show in FIGS. 7, 8, 9, 11, and in more detail in FIGS. 26 to 29. The ring 60 can be manufactured from any appropriate material such as polycarbonate.

Figure 8:
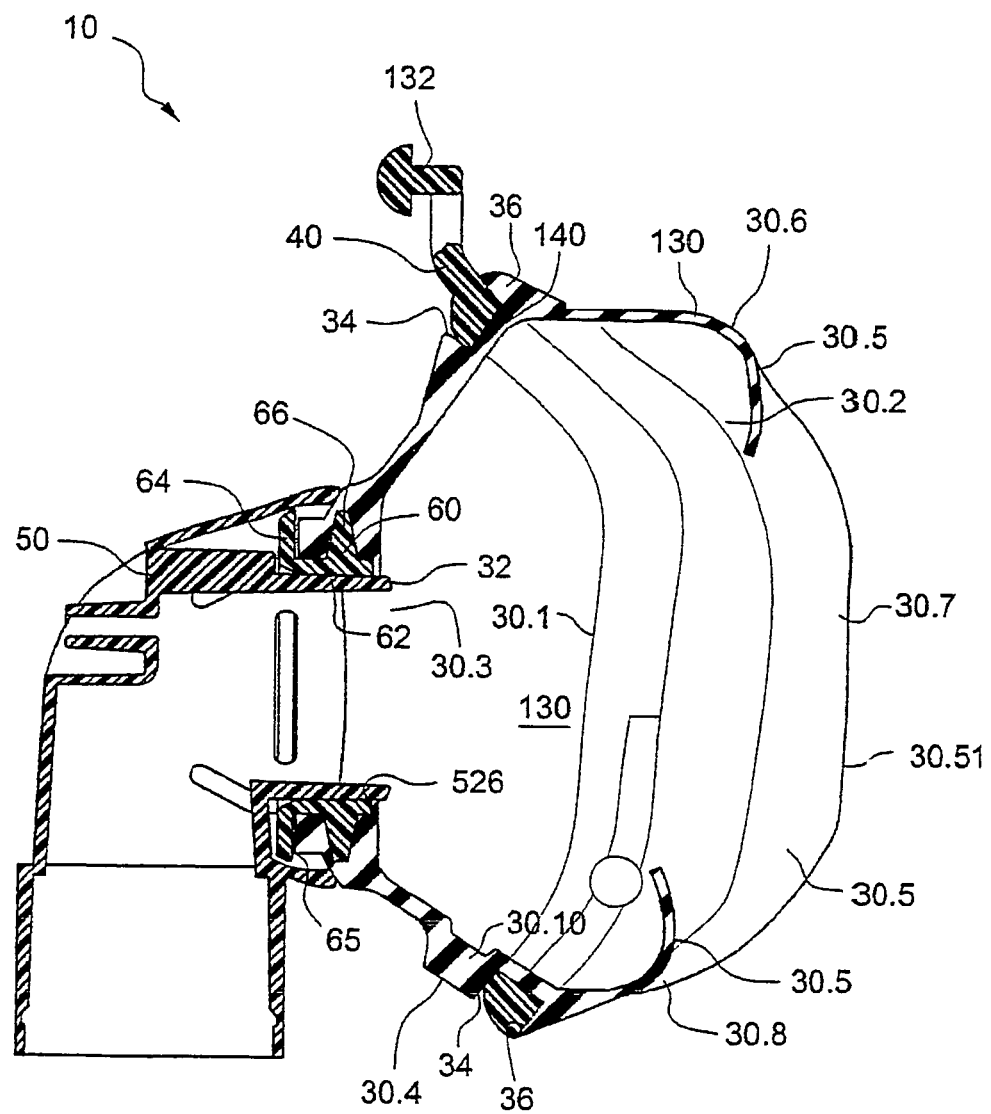
FIG. 8 shows a cross-section of the mask assembly of FIG. 2.
Figure 9:
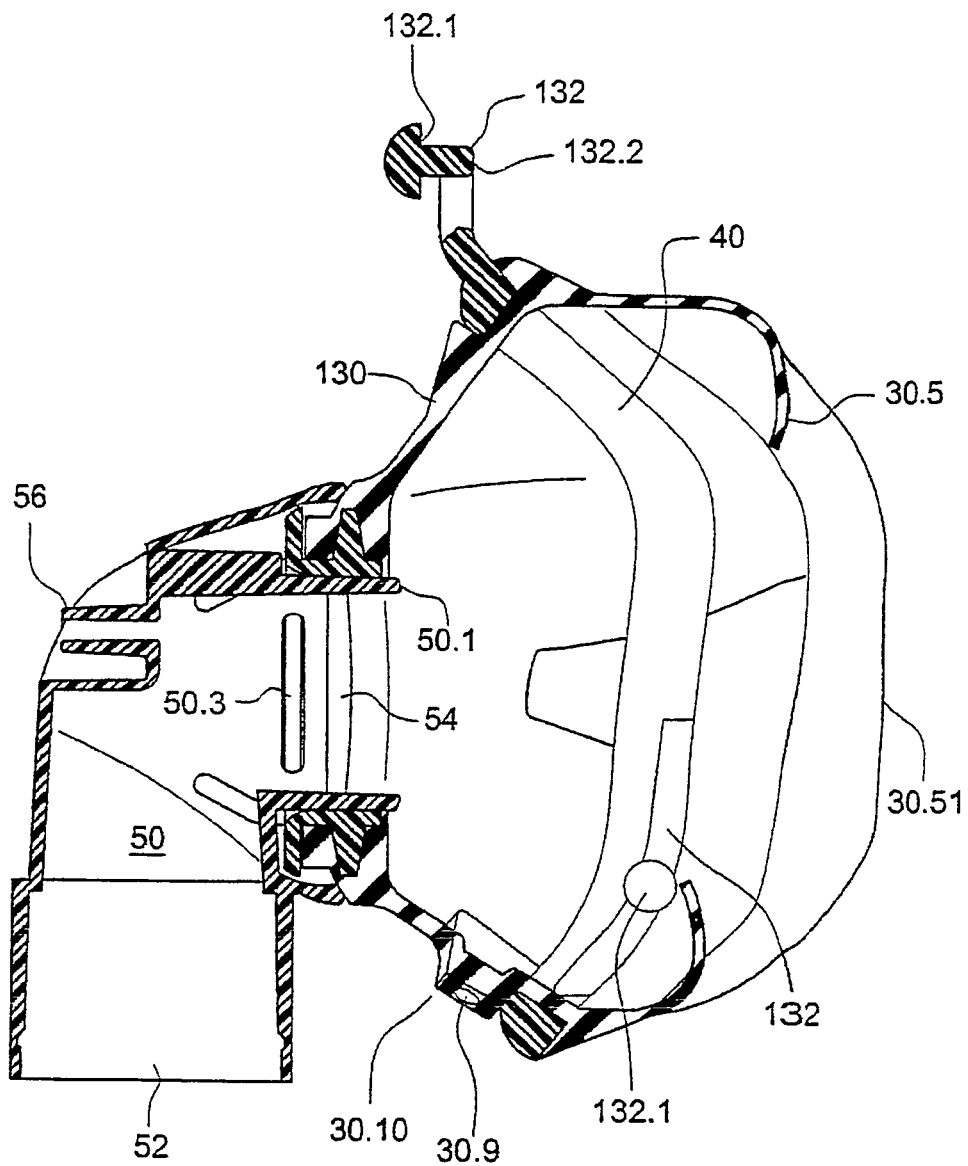
FIG. 9 shows a further cross-section of the mask assembly of FIG. 2 superimposed over a side view.
Figure 27:
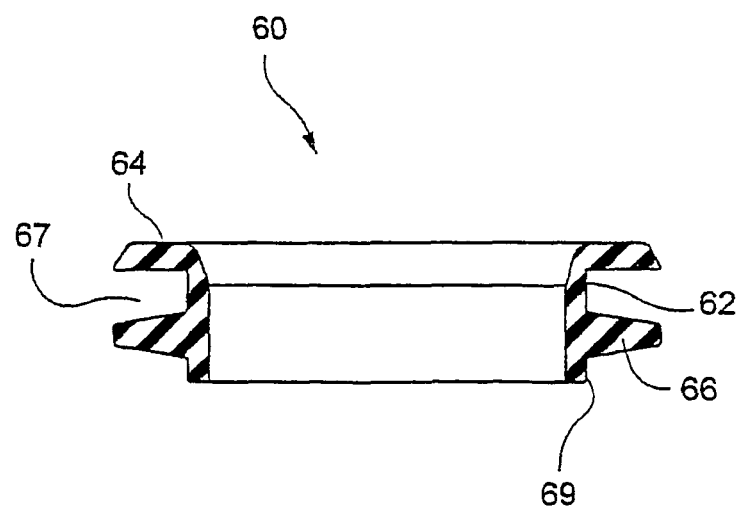
FIG. 27 illustrates a cross section through the lines XXVII-XXVII of the retaining ring of FIG. 26.
Figure 28:
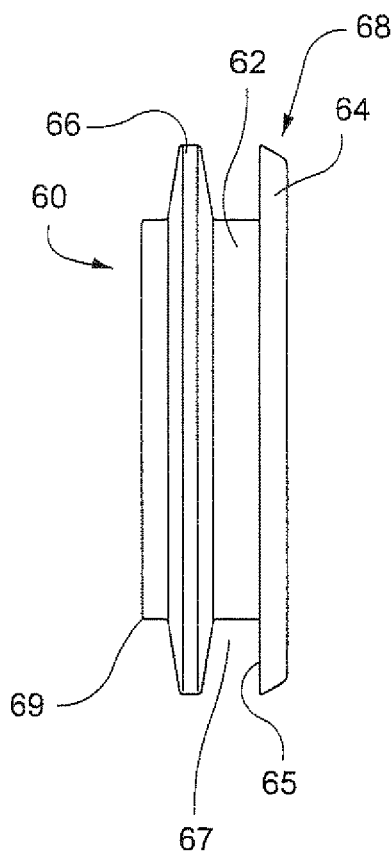
FIG. 28 illustrates a side elevation of the retaining ring of FIG. 26.
Figure 29:
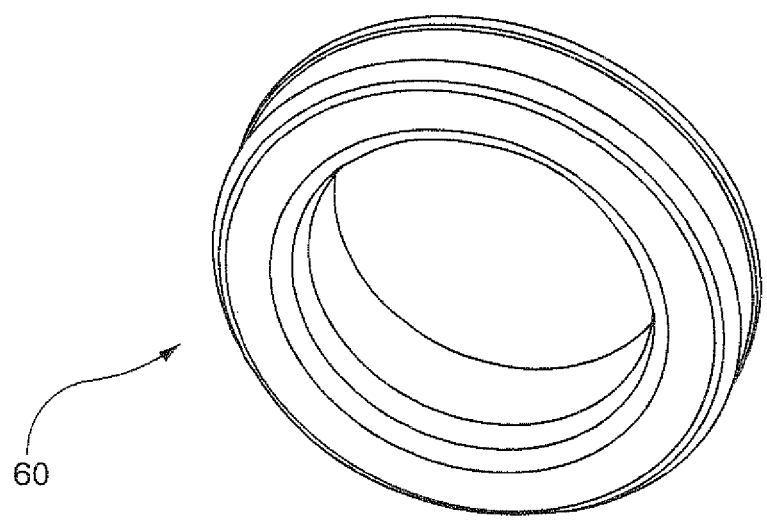
FIG. 29 illustrates a perspective view of the retaining ring of FIG. 26.
Figure 31:
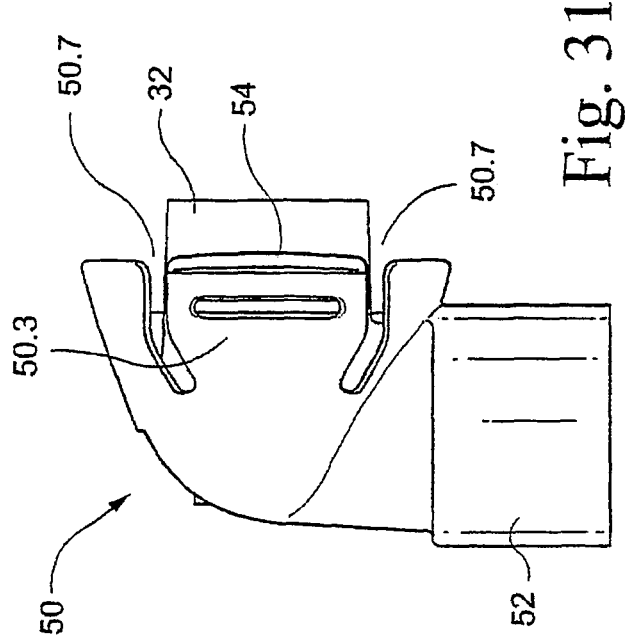
FIG. 31 illustrates a right side view of the elbow of FIG. 30.
Figure 30:
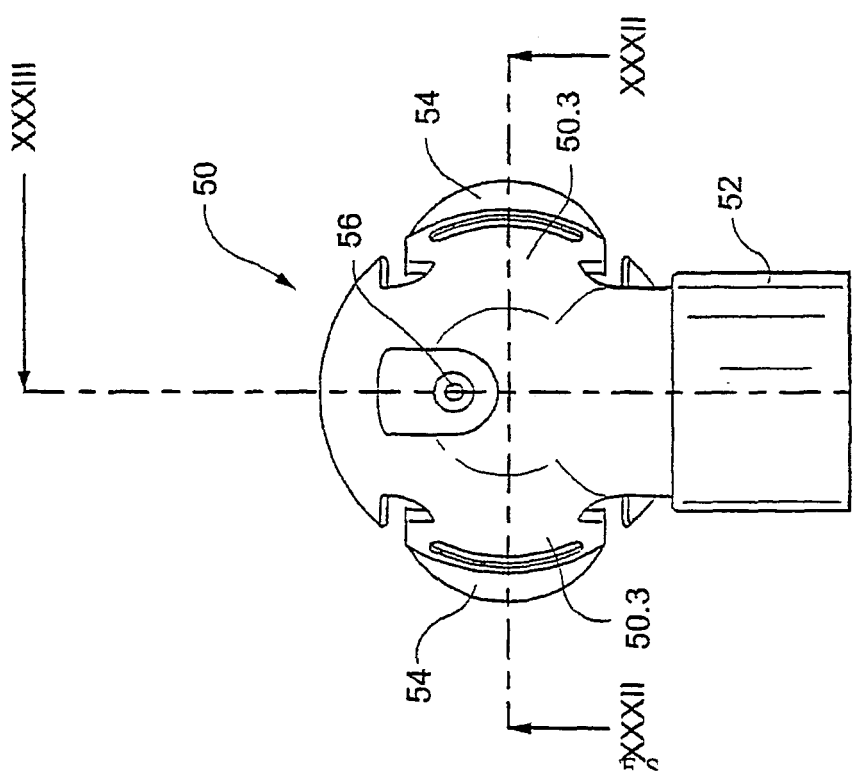
FIG. 30 illustrates a front elevation of a connection piece or elbow.
Figure 35B:
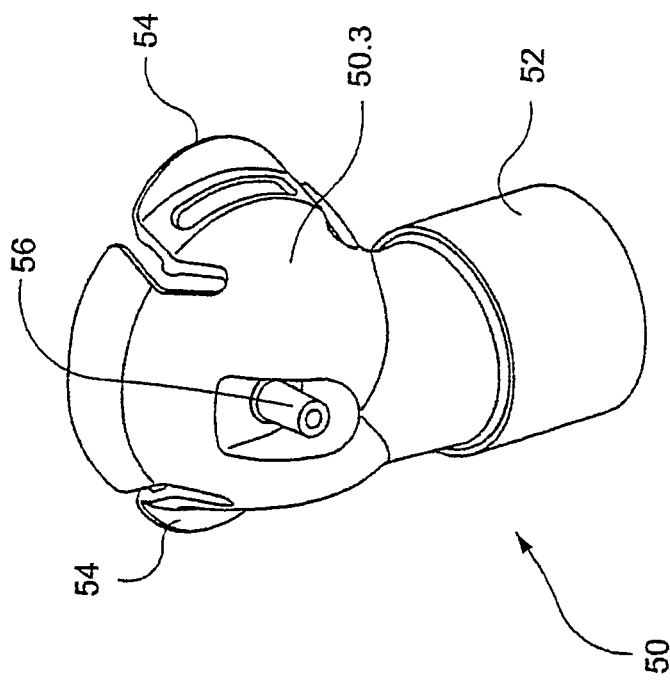
FIG. 35B illustrates an upper front perspective view of the elbow of FIG. 30.
Figure 35A:
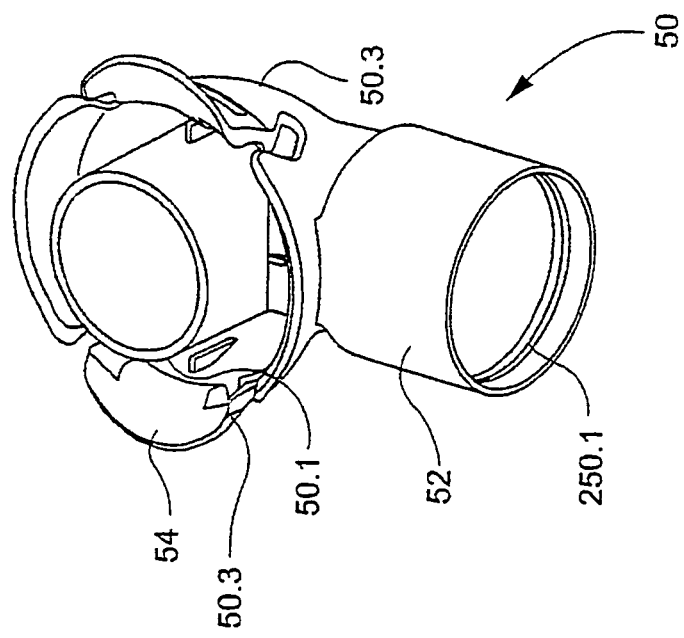
FIG. 35A illustrates a lower rear perspective view of the elbow of FIG. 30.
Figure 37:
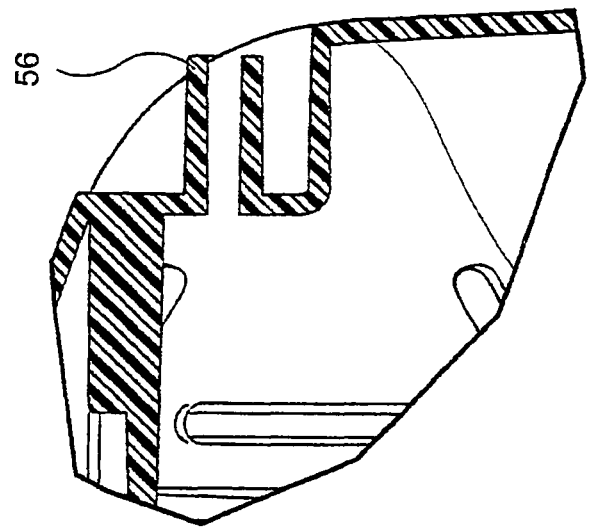
FIG. 37 illustrates detail Z of the cross section of FIG. 32.
Figure 36:
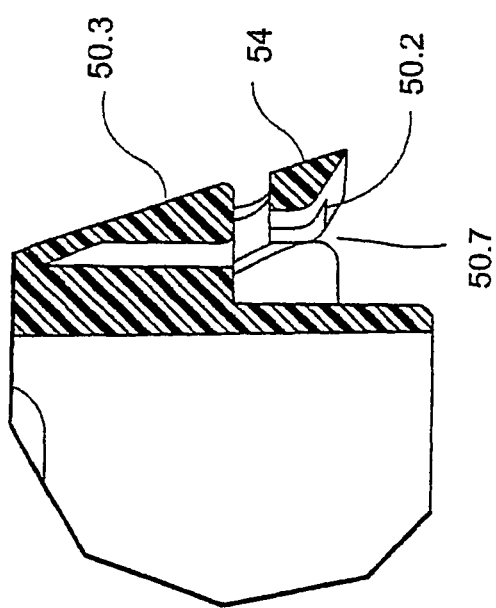
FIG. 36 illustrates detail X of the cross section of FIG. 33.
Figure 39:
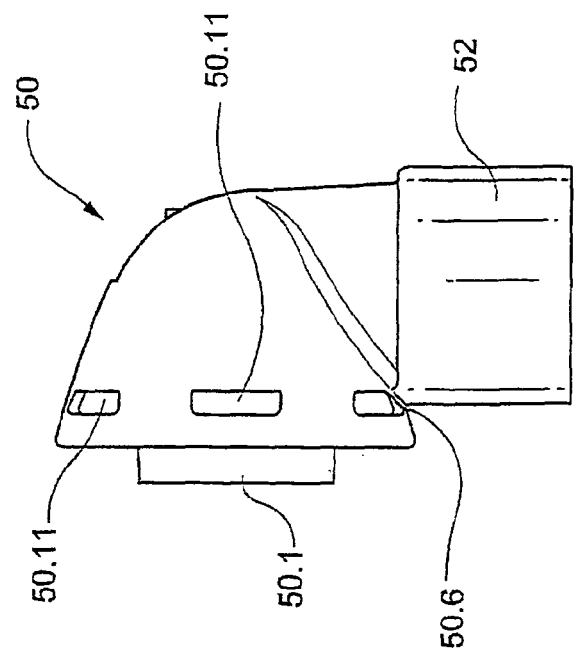
FIG. 39 illustrates a left side view of the elbow of FIG. 38.
Figure 38:
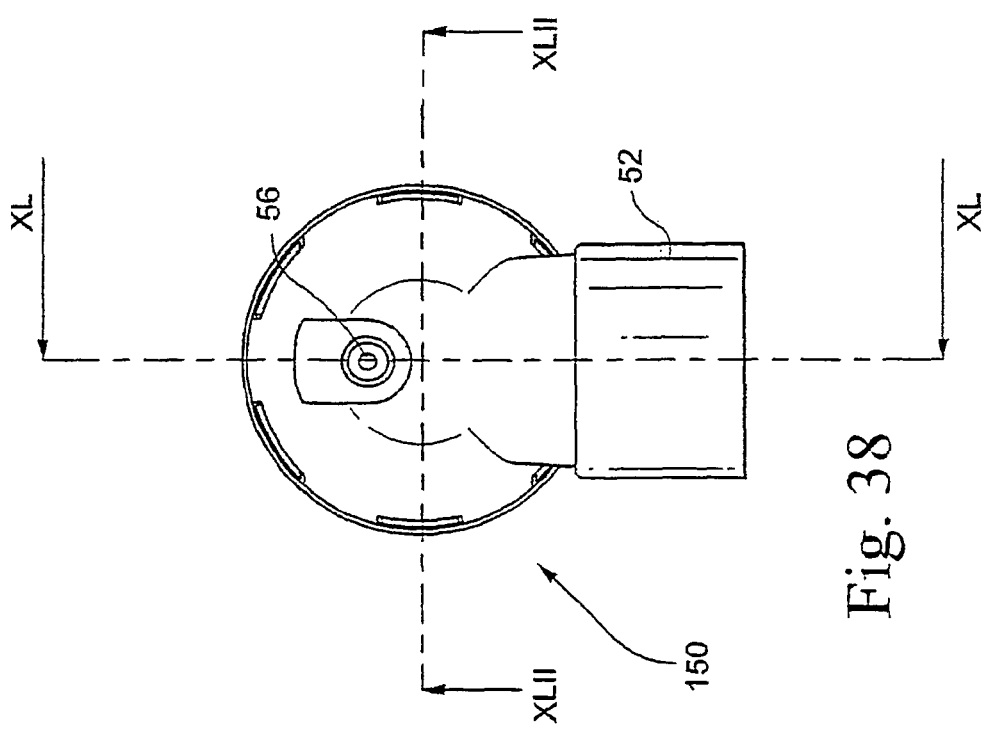
FIG. 38 illustrates a front elevation of a connection piece or elbow for single use.
Figure 41:
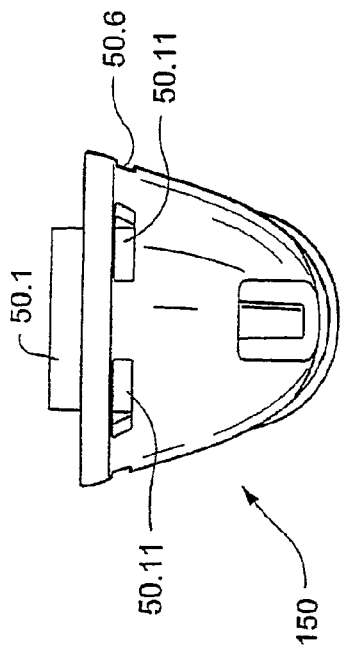
FIG. 41 illustrates a plan view of the elbow of FIG. 38.
Figure 42:
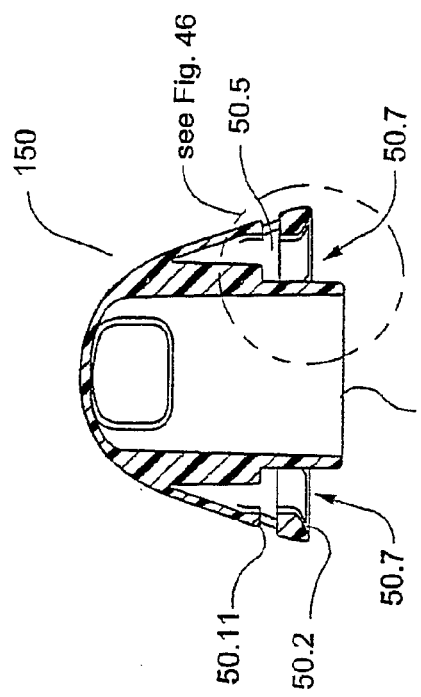
FIG. 42 illustrates a cross section through the line XLII-XLII of the elbow of FIG. 38.
Figure 40:
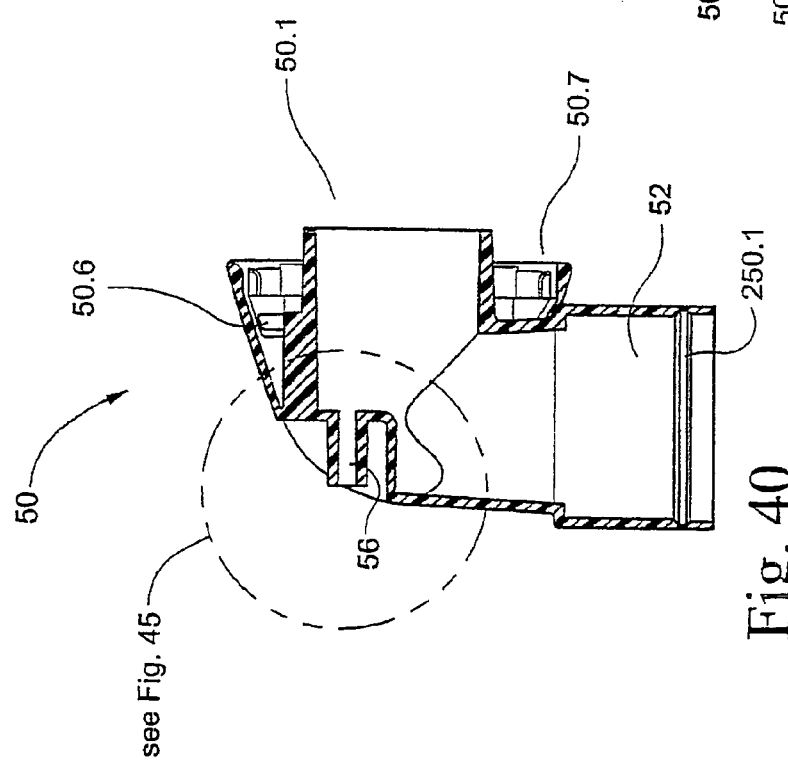
FIG. 40 illustrates a cross section through the line XL-XL of the elbow of FIG. 38.
Figure 43:
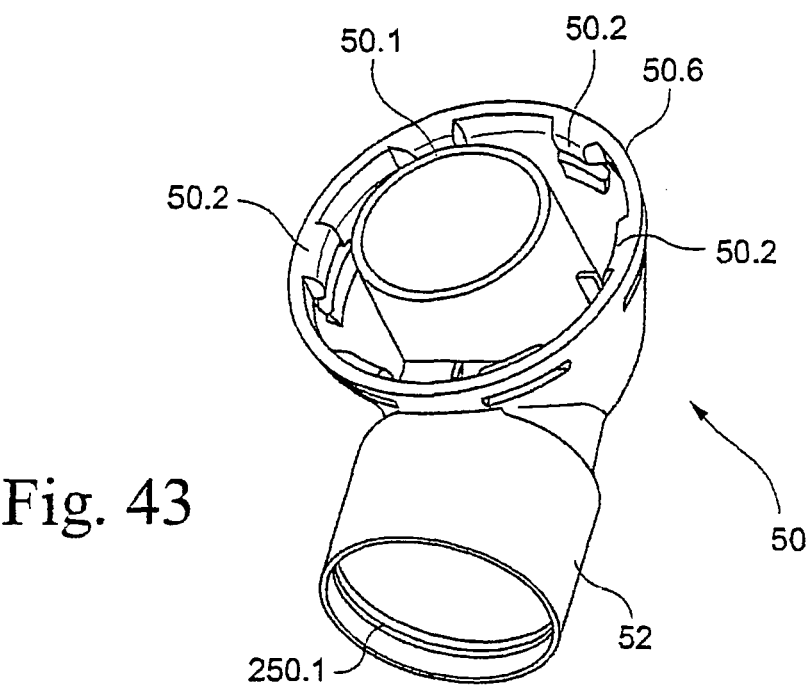
FIG. 43 illustrates a lower rear perspective view of the elbow of FIG. 38.
Figure 44:
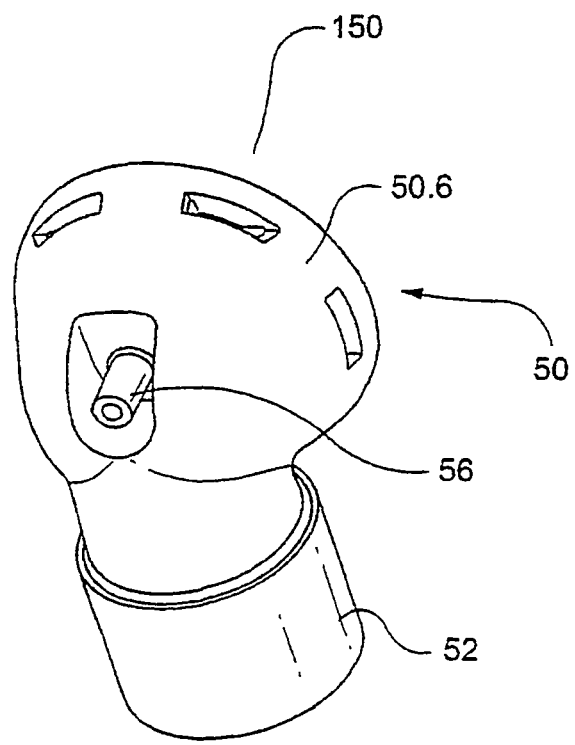
FIG. 44 illustrates an upper front perspective view of the elbow of FIG. 38.
Figure 45:
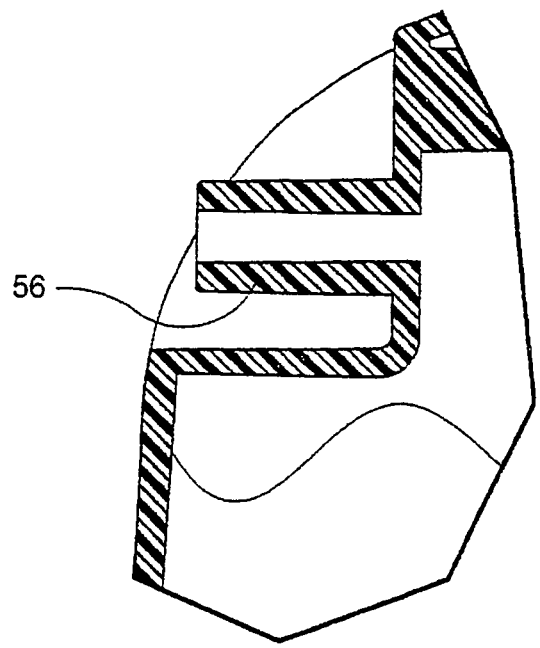
FIG. 45 illustrates detail Z of the cross section of FIG. 40.
Figure 46:
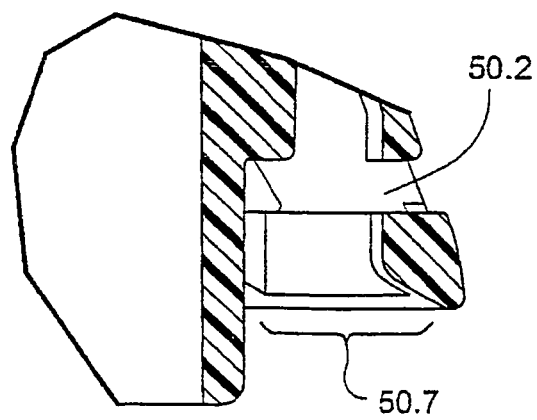
FIG. 46 illustrates detail X of the cross section of FIG. 42.
Figure 48:
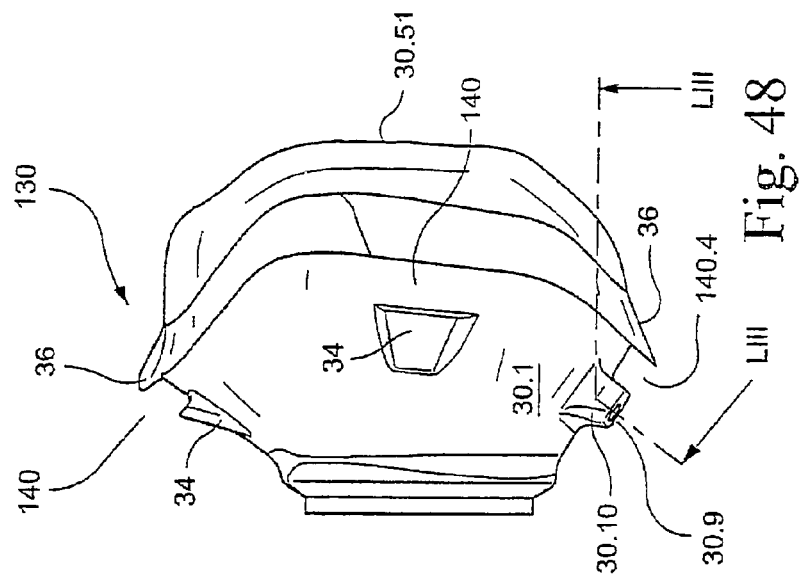
FIG. 48 illustrates a right side elevation of the shell/cushion of FIG. 47.
Figure 47:
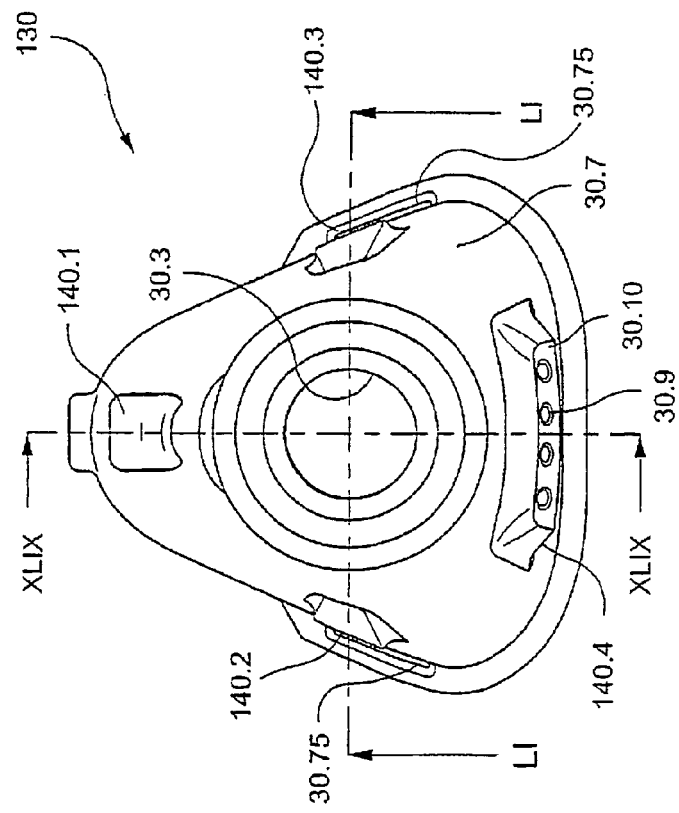
FIG. 47 illustrates a front elevation of a shell/cushion having four points or channels spaced around the periphery to attach a frame.
Figure 49:
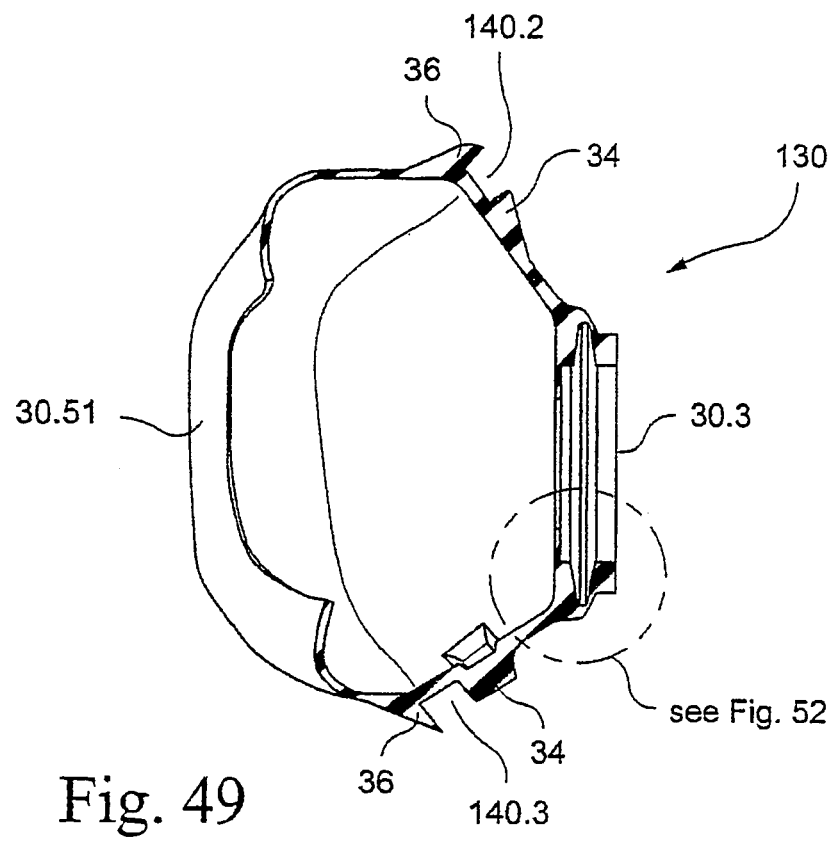
FIG. 49 illustrates a cross section through the line XLIX-XLIX of the shell/cushion of FIG. 47.
Figure 50:
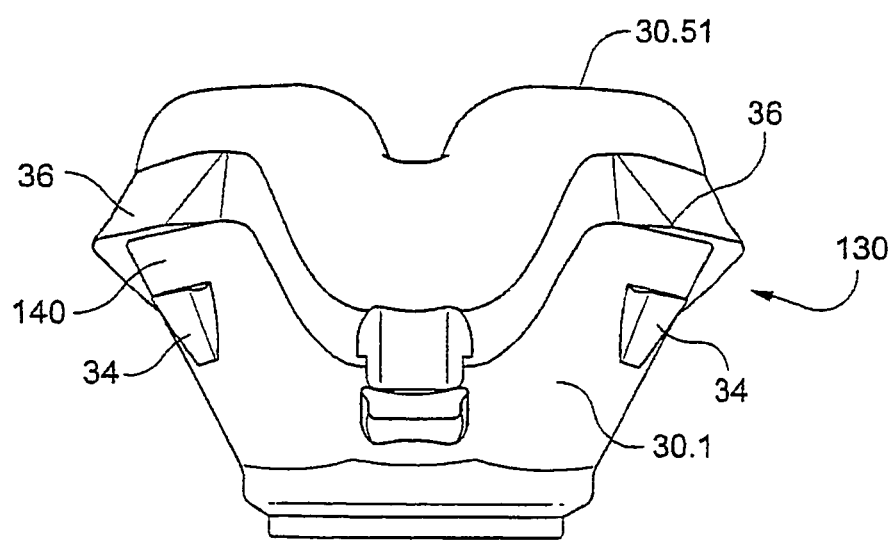
FIG. 50 illustrates a plan view of the shell/cushion of FIG. 47.

The ring 60 has an outer diameter of approximately 33 mm and a thickness of 9 mm. Other exemplary dimensions are shown in FIG. 27. FIGS. 8 and 9 show how the retaining ring is positioned in the mask assembly in use.

Illustrated in the cross sectional views of FIGS. 8 and 9 and in FIGS. 26 to 29 it can be seen that the retaining ring 60 comprises a cylinder 62, an annular front flange 64 and a rear flange 66, which between them form an annular groove 67. The rear flange 66 is adapted to be inserted and retained within a complementary shaped channel 524 adjacent the front aperture 30.3 of a shell/cushion 30, 130, 230, 330.

The front flange 64 provides a square rear surface 65 which forms the front wall of the groove 67. Further the rim 68 of the front flange 64 is bevelled or tapered so that when it enters the tapered entry way on the elbow 50, it will force the undercuts 50.2 to pass thereover.

It will be noted that the rear flange 66 is symmetrical in shape, while the front flange 64 is not. Further the rear flange 66 is set back from the rear end of the cylinder 62, whereby a cylindrical portion 69 protrudes axially rearwardly away from the rear face of the rear flange 66.

Illustrated in FIGS. 118 to 123 is another form of the retaining ring 160 which is similar to the ring 60, and like parts have been like numbered. The ring 160 differs from the ring 60 in that it has a symmetrical configuration so that it can be inserted in either orientation. The front and rear flanges, both marked with numeral 64 are a mirror image of each other and are shaped similarly to the front flange 64 of the ring 60. That is both include a rim 68 which is bevelled or tapered. It will be noted that the ring 160 does not include a rearwardly axially extending cylindrical portion such as is present on the ring 60 as feature 69.

As can be seen from the cross section of FIG. 120, the aperture through the ring 160 has convergent-divergent walls 160.1 and 160.2. These walls are angled or tapered at an angle of 20° so as to assist in the moulding of the ring 160, and to prevent jamming of the proximal end 50.1 of elbows 50 and 250 when these elbows are disconnected from the ring 160.

The shape of the groove 524 on the shell/cushion to receive the flange 64 of ring 160 is preferably of a complementary shape to allow the ring 160 to provide support.

§7 Assembly of the Components

Assembly of Version 1 of a mask system described in chapter §1 above, will now be described with reference to FIGS. 7, 8 and 9.

A frame 40 is pushed into position on the shell/cushion 30 from the front of the shell/cushion 30 and is inserted and engages with the channel 140 on the shell/cushion 30. The retaining ring 60 is adapted to engage with a channel 250 on the shell/cushion 30. The process is similar for the first embodiment.

Illustrated in the cross sectional views of FIGS. 8 and 9 of the mask assembly 10, the connection between the elbow 50, retaining ring 60 and shell/cushion 30 is visible. The rear flange 66 of the retaining ring 60 is adapted to be inserted and retained within in the channel 524 adjacent the front aperture 30.3 of a shell/cushion 30.

The undercut 50.2 on the elbow 50 is adapted to engage with the rear surface 65 of the front flange 64, thus retaining the elbow 50.

When the proximal end 50.1 passes though the retaining ring 60, seal is formed between a flange or flap 526 on the shell/cushion 30 and the proximal end 32 of the elbow 50. In this way, a leak proof seal, which allows rotation of the elbow 50 relative to the shell/cushion 30 is formed, since the flange or flap 526 extends over the proximal end of the elbow in an annular fashion. This results in a conformable seal between the shell/cushion and elbow.

Assembly of Version 7 of a mask system described in the §1 Introduction above, will now be described with reference to FIGS. 122 to 125.

Assembly of Version 7 is very similar to that of version 1 described above, except that instead of a single piece frame 40 a two piece frame, made up of pieces 240 and 340 is used, and instead of a shell/cushion 30 with a channel 140 being used a shell/cushion 330 with a peripheral flange 330.1 is used. The assembly of (a) the frame to the shell/cushion; and (b) the retaining ring and elbow to the shell/cushion; can be done in any order.

Figure 124:
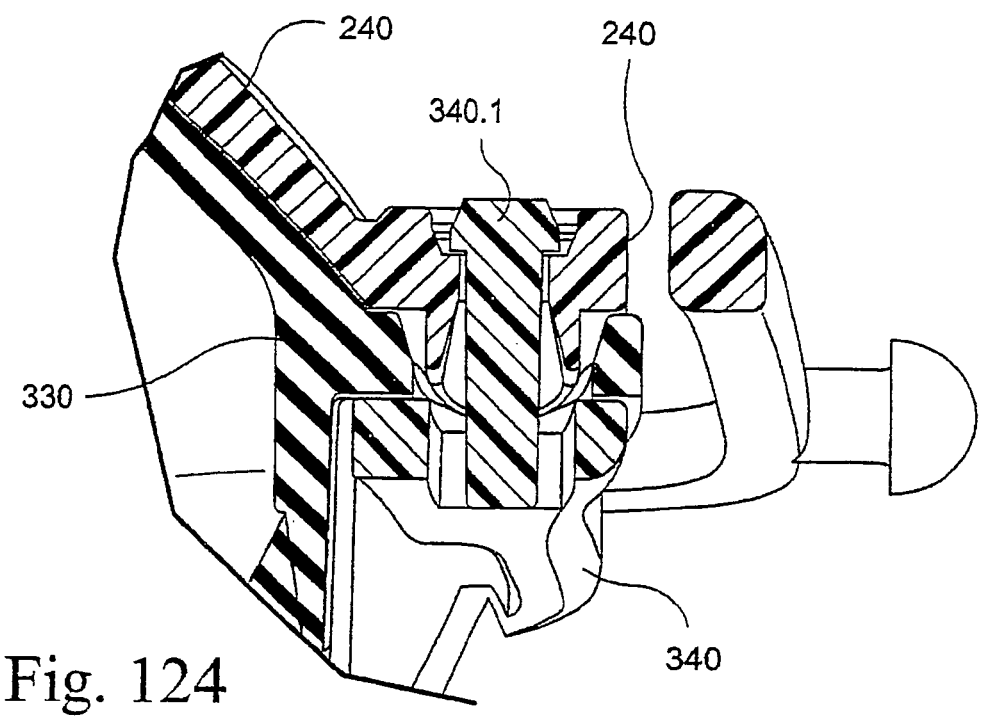

To assemble the frame, a manufacturer will align the rivets 340.1 and spigots 340.7 with the respective holes 330.3 and 330.2, and pass the rivets and spigots through these holes in a rearward to forward direction, starting at the rear of the shell/cushion 330. Once the rivets have been received through the holes 330.2 and the rest of the flange 330.1 is sitting adjacent to front facing surfaces of the piece 340, then the piece 240 is aligned so that the apertures 240.1 align with the rivets 340.1, whereby exerting a compressive force on the two pieces 240 and 340 will force the tapered mushroom heads of the rivets 340.1 to pass through the constricted aperture of the apertures 240.1. By appropriately sizing the rivets 340.1 and the apertures 240.1, it may be necessary to compress the flange 330.1 whereby the pieces 240 and 340 will keep the flange 330.1 compressed therebetween once the mushroom head of the rivets are locked into the apertures 240.1. Alternatively, as illustrated in FIG. 124, the gap between the pieces 240 and 340 can be sized to receive the flange 330.1 without any compression thereof.

When the rivets 340.1 are locked into the apertures 240.1, the spigots 340.7 pass through the holes 330.3. The three spigots 340.7 prevent the flange 330.1 from extricating itself from the sandwich formed by the clamping of pieces 240 and 340.

Figure 125:
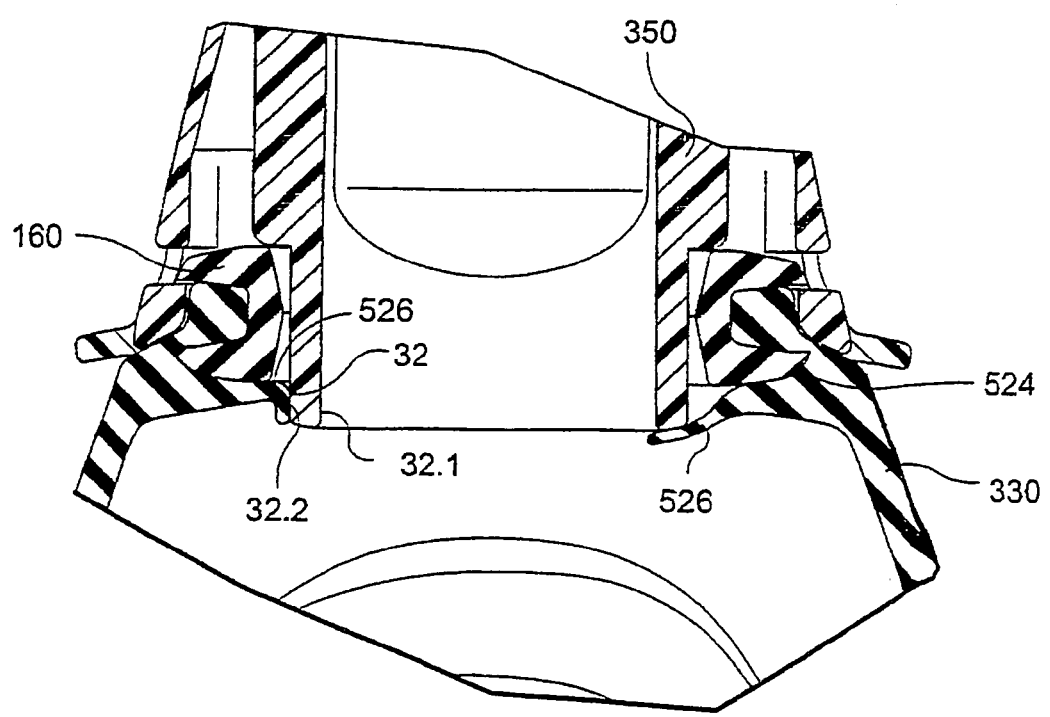

The assembly of the retaining ring 160 and the elbow 350 onto the aperture 30.3 of the shell/cushion 330 is the same procedure as described above in respect of version 1. As illustrated in FIG. 125, the flange 526 can, once the elbow 350 is assembled to the retaining ring 160 and shell/cushions 330, overlie (as illustrated on the right half of FIG. 125) the rim 32.1 of the proximal end 32 of elbow 350, or as illustrated on the left half of FIG. 125, the flange 526 can circumferentially seal on the cylindrical outer surface 32.2 adjacent the rims 32.1.

Described above is a feature of single use mask assemblies where the shell/cushion 30, 130, 230, 330 has a reduced thickness portion to provide a tear point. A single use version is able to be manufactured without such a line of weakness or tear point. Such a single use version, when a single use elbow is used, such as elbows 150 or 350 described above, will allow the shell/cushion 30, 130, 230, 330 (without any reduced thicknesses or tearing points) to separate from the assembled retaining ring 60 or 160 and the elbow 150, or 350, while the elbow 150 or 350 retains the retaining ring 60 or 160 captured thereon. In this way, such a mask assembly will not be able to be reassembled due to the inability to extract or disconnect the retaining ring 60 or 160 from the elbow 150 or 350.

Although the invention has been described with reference to preferred embodiments, it is to be understood that these embodiments are merely illustrative of the application of the principles of the invention. Numerous modifications may be made therein and other arrangements may be devised without departing from the spirit and scope of the invention.

It will be understood that the invention disclosed and defined herein extends to all alternative combinations of two or more of the individual features mentioned or evident from the text. All of these different combinations constitute various alternative aspects of the invention.

The invention claimed is:

1. A mask system for treating sleep disordered breathing, comprising:
    a shell and cushion unit including a cushion portion and a shell portion, the cushion portion having two walls and a rear aperture surrounded by a face contacting portion adapted to form a seal with the patient's face, the face contacting portion including a nasal bridge region and side regions extending from the nasal bridge region, the shell portion including a centrally located front aperture opposite the cushion portion and a projection located adjacent the front aperture and oriented towards an interior of a breathing chamber, the shell and cushion unit being a single integral component defining the breathing chamber;

a rigid, generally triangularly-shaped frame with rounded lower corners, the frame engaging the shell portion of the shell and cushion unit, the frame having at least one opening leaving at least a portion of the shell portion uncovered, and the frame being secured to and positively located relative to the shell and cushion unit;

a rigid ring-shaped member with an annular flange, at least a portion of which is adjacent to the front aperture of the shell and cushion unit;

a rotatable elbow having a first end and a second end, the first end engaging with and being rotatable relative to the rigid ring-shaped member and engaging with and being rotatable relative to the shell and cushion unit, a portion of the first end extending through and beyond the ring-shaped member and engaging the shell portion projection;

a swivel attached to the second end of the rotatable elbow and adapted to engage an air delivery conduit;

headgear to support the shell and cushion unit on the user's face; and anchor points for the headgear formed on the frame, the anchor points including a first anchor point provided on a first side portion of the frame, and a second anchor point provided on a second side portion of the frame so that the centrally located front aperture on the shell portion is positioned between the first and second anchor points.

2. The mask system according to claim 1, wherein the headgear comprises a multi-layered one-piece construction.

3. The mask system according to claim 2, wherein the elbow includes an approximately 90° bend between the first and second ends thereof.

4. The mask system according to claim 3, wherein the first and second anchor points are proximate to the rounded lower corners of the frame.

5. The mask system according to claim 4, wherein the ring-shaped member and the frame comprise a common material.

6. The mask system according to claim 5, wherein the elbow comprises polycarbonate.

7. The mask system according to claim 5, wherein the ring-shaped member, the elbow and the frame comprise polycarbonate.

8. The mask system according to claim 1, wherein the shell and cushion unit include a continuous rear flange, a continuous front flange and a continuous channel between the rear flange and the front flange.

9. The mask system according to claim 8, wherein a contour of a rear portion of the frame substantially matches a contour of the rear flange.

10. The mask system according to claim 9, wherein the continuous channel has a different thickness at different regions of the shell and cushion unit.

11. The mask system according to claim 1, wherein a shoulder of the elbow abuts the annular flange of the ring-shaped member.

12. The mask system according to claim 1, further including third and fourth anchor points, wherein the headgear includes four straps structured to be anchored to the first, second, third and fourth anchor points, respectively.

13. The mask system according to claim 1, wherein the frame is an exoskeletal frame.

14. The mask system according to claim 1, wherein the rotatable elbow includes a passage wall and a vent wall that extends away from the passage wall, the vent wall including at least one aperture therethrough, the at least one aperture lying at an angle to an outlet direction of air flowing out of the elbow.

15. The mask system according to claim 14, wherein the frame has a rearwardly projecting rib that engages the shell and cushion unit.

16. The mask system according to claim 15, further comprising a securing mechanism to secure the shell and cushion unit and the frame.

17. The mask system according to claim 16, wherein the shell and cushion unit is sandwiched between the securing mechanism and the frame.

18. The mask system according to claim 17, wherein the securing mechanism passes through a portion of the shell and cushion unit.

19. The mask system according to claim 1, wherein the elbow is freely rotatable when mounted on the mask system.

20. The mask system according to claim 1, wherein the cushion portion comprises a nasal or full face cushion.

21. A mask system for treating sleep disordered breathing, comprising:

headgear;

a shell and cushion unit adapted to form a seal with a patient and defining an interior breathing chamber, the cushion portion having two walls and the shell portion including an opening with front and rear sides, and a projection oriented on the rear side of the opening towards the breathing chamber;

a frame shaped and adapted to be engaged with the shell portion of the shell and cushion unit, the frame being attachable to the headgear to position the mask system on a patient's head; and a rotatable elbow having a proximal end adapted to engage with the shell and cushion unit, an end of the rotatable elbow being rotatably received within the breathing chamber and engaging the shell portion projection.

22. The mask system according to claim 21, wherein the shell and cushion unit includes a centrally located front aperture and the shell portion projection is located adjacent the front aperture.

23. The mask system according to claim 22, wherein the frame includes a plurality of anchor points for the headgear and the shell and cushion unit aperture is provided generally between the anchor points.

24. The mask system according to claim 21, wherein the elbow includes an approximately 90° bend between the first and second ends thereof, and the elbow is rotatable in any position.

25. The mask system according to claim 24, further comprising a swivel attached to the rotatable elbow and adapted to engage an air delivery conduit.

26. The mask system according to claim 25, wherein the elbow comprises polycarbonate.

27. The mask system according to claim 21, further comprising a ring member that receives the elbow.

28. The mask system according to claim 27, wherein the ring member and the frame comprise polycarbonate.

29. The mask system according to claim 28, wherein the ring member includes an annular flange.

30. The mask system according to claim 29, wherein the annular flange is symmetrical in shape.

31. The mask system according to claim 30, wherein the rotatable elbow includes a shoulder that abuts the annular flange.

32. The mask system according to claim 21, wherein the frame includes at least one opening through which at least a portion of the shell and cushion unit is exposed.

33. The mask system according to claim 32, wherein the frame is of a generally triangular shape with rounded apexes.

34. The mask system according to claim 33, wherein the frame includes anchor points for the headgear.

35. The mask system according to claim 34, wherein the frame includes two anchor points for the headgear, and the mask system further comprises two additional anchor points for the headgear.

36. The mask system according to claim 21, wherein the headgear comprises a multi-layered one-piece construction.

37. The mask system according to claim 21, wherein the shell and cushion unit has a generally triangular shape.

38. The mask system according to claim 37, wherein the shell and cushion unit includes at least one flange extending away from an outer surface and surrounding the shell and cushion unit, and the frame is generally shaped to substantially match a shape of the at least one flange of the shell and cushion unit.

39. The mask system according to claim 21, wherein the rotatable elbow includes a passage wall and a vent wall that extends away from the passage wall, the vent wall including at least one aperture therethrough, the at least one aperture lying at an angle to an outlet direction of air flowing out of the elbow.

40. The mask system according to claim 39, wherein the frame has a rearwardly projecting rib that engages the shell and cushion unit.

41. The mask system according to claim 40, further comprising a securing mechanism to secure the shell and cushion unit and the frame.

42. The mask system according to claim 21, wherein the cushion portion is either a full face cushion or a nasal cushion.

43. The mask system according to claim 21, wherein the elbow is freely rotatable when mounted on the mask system.

44. A mask system for treating sleep disordered breathing, comprising:
   headgear;
   a shell and cushion unit adapted to form a seal with a patient and defining an interior breathing chamber, the cushion portion being a full face cushion and having two walls and the shell portion including an opening with front and rear sides, and a projection oriented on the rear side of the opening towards the breathing chamber;
   a frame shaped and adapted to be engaged with the shell and cushion unit, the frame being attachable to the headgear to position the mask system on a patient's head; and
   a rotatable elbow having a proximal end adapted to engage with the shell portion of the shell and cushion unit, an end of the rotatable elbow being rotatably received within the breathing chamber and engaging the shell portion projection.

45. The mask system according to claim 44, wherein the shell and cushion unit includes a centrally located front aperture and the shell portion projection is located adjacent the front aperture.

46. The mask system according to claim 45, wherein the frame includes a plurality of headgear anchor points and the shell and cushion unit aperture is provided generally between the headgear anchor points.

47. The mask system according to claim 44, wherein the elbow includes an approximately 90° bend between the first and second ends thereof.

48. The mask system according to claim 47, further comprising a swivel attached to the rotatable elbow and adapted to engage an air delivery conduit.

49. The mask system according to claim 48, wherein the elbow comprises either a polycarbonate or polypropylene material.

50. The mask system according to claim 44, further comprising a ring member that receives the elbow.

51. The mask system according to claim 50, wherein the ring member and the frame are formed from a common material.

52. The mask system according to claim 51, wherein the ring member includes an annular flange.

53. The mask system according to claim 52, wherein the annular flange is symmetrical in shape.

54. The mask system according to claim 53, wherein the rotatable elbow includes a shoulder that abuts the annular flange.

55. The mask system according to claim 44, wherein the frame includes at least one opening through which at least a portion of the shell and cushion unit is exposed.

56. The mask system according to claim 55, wherein the frame is of a generally triangular shape with rounded apexes.

57. The mask system according to claim 56, wherein the frame includes anchor points for the headgear.

58. The mask system according to claim 57, wherein the frame includes two anchor points for the headgear.

59. The mask system according to claim 44, wherein the headgear comprises a multi-layered one-piece construction.

60. The mask system according to claim 44, wherein the shell and cushion unit has a generally triangular shape.

61. The mask system according to claim 60, wherein the shell and cushion unit includes at least one flange extending away from an outer surface and surrounding the shell and cushion unit, and the frame is generally shaped to substantially match a shape of the at least one flange of the shell and cushion unit.

62. The mask system according to claim 44, wherein the rotatable elbow includes a passage wall and a vent wall that extends away from the passage wall, the vent wall including at least one aperture therethrough, the at least one aperture lying at an angle to an outlet direction of air flowing out of the elbow.

63. The mask system according to claim 62, wherein the frame has a rearwardly projecting rib that engages the shell and cushion unit.

64. The mask system according to claim 63, further comprising a securing mechanism to secure the shell and cushion unit and the frame.

65. The mask system of claim 44, wherein the elbow is freely rotatable when mounted on the mask system.

66. A mask system for treating sleep disordered breathing, comprising:
   headgear;
   a combination shell and cushion unit defining an interior breathing chamber, adapted to form a seal with a face of a patient, and including a front aperture and a projection located adjacent a rear side of the front aperture such that the projection is oriented towards an interior of the breathing chamber;
   a frame with a plurality of anchor points for anchoring the headgear to the frame and positioning the shell and cushion unit onto the patient's head;
   a rotatable elbow engaging the projection and including an inlet, an outlet, a passage wall and a vent wall that extends away from the passage wall and is in the vicinity of the outlet between the outlet and the inlet, the vent wall including at least one aperture therethrough the elbow being freely rotatable when mounted; and a securing device that secures the frame to the shell and cushion unit, a portion of the shell and cushion unit being sandwiched between the securing device and the frame when the shell and cushion unit is secured to the frame.

67. The mask system according to claim 66, wherein the securing device passes through the portion of the shell and cushion unit to secure the shell and cushion unit to the frame.

68. The mask system according to claim 67, wherein the frame further comprises a rearwardly projecting rib.

69. The mask system according to claim 66, wherein the securing device is independent from the anchor points.

70. The mask system according to claim 69, wherein the securing device allows rotation of the elbow relative to the frame and the shell and cushion unit.

71. The mask system according to claim 66, wherein the at least one aperture lies at an oblique angle to a direction of air flowing through the outlet.

72. The mask system according to claim 71, wherein the angle is approximately 35 degrees.

73. The mask system according to claim 66, wherein the front aperture is provided generally between the anchor points.

74. The mask system according to claim 73, wherein the frame includes two anchor points for the headgear, and the mask system further comprises two additional anchor points for the headgear.

75. The mask system according to claim 66, further comprising a swivel attached to the rotatable elbow and adapted to engage an air delivery conduit.

76. The mask system according to claim 66, wherein the combination shell and cushion unit includes at least one flange extending away from an outer surface and surrounding the combination shell and cushion, and the frame having a shape which substantially matches the contours of the at least one flange.

77. The mask system according to claim 66, wherein the frame includes at least one opening through which at least a portion of the combination shell and cushion is exposed.

78. The mask system according to claim 67, wherein the frame is of a generally triangular shape with rounded apexes.

79. The mask system according to claim 66, wherein a sealing structure of the combination shell and cushion has two walls.

80. The mask system according to claim 66, wherein the frame is an exoskeletal frame.

81. The mask system according to claim 66, wherein a cushion portion of the shell and cushion unit comprises a nasal or full face cushion.

82. A mask system for treating sleep disordered breathing, comprising:

headgear;

a frame having a plurality of anchor points to connect the headgear;

a combined shell and cushion coupled to the frame and defining an interior breathing chamber, the combined shell and cushion comprising a cushion adapted to form a seal on the patient's face and, on the opposing side, a shell defining a centrally located front aperture having a rigid retaining ring with a raised rim; and an elbow rotatably directly connected to the retaining ring and having a first end fitted with a swivel connector for connecting a conduit providing air flow to the mask and a second end, a portion of the second end extending into the breathing chamber beyond the raised rim, the elbow including at least one undercut proximal the second end, the at least one undercut to retainably engage the raised rim of the retaining ring.

83. The mask system according to claim 82, wherein the headgear comprises a multi-layered one-piece construction.

84. The mask system according to claim 83, wherein the elbow includes an approximately 90° bend between the first and second ends thereof.

85. The mask system according to claim 84, further comprising two anchor points to anchor the headgear.

86. The mask system according to claim 85, wherein the retaining ring and the frame comprise polycarbonate.

87. The mask system according to claim 86, wherein the elbow comprises polycarbonate.

88. The mask system according to claim 86, wherein the retaining ring, the elbow and the frame comprise a common material.

89. The mask system according to claim 82, wherein the frame includes first and second anchor points, and the mask system further comprises third and fourth anchor points, wherein the headgear includes four straps structured to be anchored to the anchor points.

90. The mask system according to claim 82, wherein the frame is an exoskeletal frame.

91. The mask system according to claim 82, wherein the elbow includes a passage wall and a vent wall that extends away from the passage wall, the vent wall including at least one aperture therethrough, the at least one aperture lying at an angle to an outlet direction of air flowing out of the elbow.

92. The mask system according to claim 91, wherein the frame has a rearwardly projecting rib that engages the combined shell and cushion.

93. The mask system according to claim 92, further comprising a securing mechanism to secure the combined shell and cushion and the frame.

94. The mask system according to claim 93, wherein a portion of the combined shell and cushion is sandwiched between the securing mechanism and the frame.

95. The mask system according to claim 94, wherein the securing mechanism passes through the portion of the combined shell and cushion.

96. The mask system according to claim 82, wherein the elbow is freely rotatable.

97. The mask system according to claim 82, wherein the cushion comprises a nasal or full face cushion.

98. A mask system for treating sleep disordered breathing, comprising:

headgear;

a mask comprising:

a frame having a plurality of anchor points to connect the headgear; and a combined shell and cushion coupled to the frame and defining an interior breathing chamber, the combined shell and cushion comprising a cushion adapted to form a seal on the patient's face and, on the opposing side, a shell defining a centrally located front aperture having positioned therein a rigid retaining ring with a raised rim; and an elbow rotatably directly connected to the mask and having a first end fitted with a swivel connector for connecting a conduit providing air flow to the mask and a second end, a portion of the second end extending into the breathing chamber beyond the raised rim, the elbow including at least one undercut proximal the second end, the at least one undercut to retainably engage the raised rim of the retaining ring.

99. The mask system according to claim 98, wherein the headgear comprises a multi-layered one-piece construction.

100. The mask system according to claim 99, wherein the elbow includes an approximately 90° bend between the first and second ends thereof.

101. The mask system according to claim 100, wherein the anchor points are proximate to lower rounded corners of the frame.

102. The mask system according to claim 101, wherein the retaining ring and the frame comprise a common material.

103. The mask system according to claim 102, wherein the elbow comprises polycarbonate.

104. The mask system according to claim 102, wherein the retaining ring, the elbow and the frame comprise polycarbonate.

105. The mask system according to claim 98, wherein the frame includes first and second anchor points, and the mask system further comprises third and fourth anchor points, wherein the headgear includes four straps structured to be anchored to the first, second, third and fourth anchor points, respectively.

106. The mask system according to claim 98, wherein the frame is an exoskeletal frame.

107. The mask system according to claim 98, wherein the elbow includes a passage wall and a vent wall that extends away from the passage wall, the vent wall including at least one aperture therethrough, the at least one aperture lying at an angle to an outlet direction of air flowing out of the elbow.

108. The mask system according to claim 107, wherein the frame has a rearwardly projecting rib that engages the combined shell and cushion.

109. The mask system according to claim 108, further comprising a securing mechanism to secure a portion of the combined shell and cushion and the frame.

110. The mask system according to claim 109, wherein the portion of the combined shell and cushion is sandwiched between the securing mechanism and the frame.

111. The mask system according to claim 110, wherein the securing mechanism passes through a portion of the combined shell and cushion.

112. The mask system according to claim 98, wherein the elbow is freely rotatable.

113. The mask system according to claim 98, wherein the cushion comprises a nasal or full face cushion.

114. A mask system for treating sleep disordered breathing, comprising:
headgear;
a mask comprising:
a frame having a plurality of anchor points to connect the headgear; and
a combined shell and cushion coupled to the frame and defining an interior breathing chamber, the combined shell and cushion comprising a cushion adapted to form a seal on the patient's face and, on the opposing side, a shell having positioned therein a centrally located rigid retaining ring with a raised rim; and
an elbow rotatably directly connected to the mask and having a first end fitted with a swivel connector for connecting a conduit providing air flow to the mask and a second end, a portion of the second end extending into the breathing chamber beyond the raised rim, the elbow including at least one undercut proximal the second end, the at least one undercut to retainably engage the raised rim of the retaining ring.

115. The mask system according to claim 114, wherein the headgear comprises a multi-layered one-piece construction.

116. The mask system according to claim 115, wherein the elbow includes an approximately 90° bend between the first and second ends thereof.

117. The mask system according to claim 116, wherein the anchor points are proximate to lower rounded corners of the frame.

118. The mask system according to claim 117, wherein the retaining ring and the frame comprise a common material.

119. The mask system according to claim 118, wherein the elbow comprises polycarbonate.

120. The mask system according to claim 118, wherein the retaining ring, the elbow and the frame comprise a common material.

121. The mask system according to claim 114, wherein the frame includes first and second anchor points, and the mask system further comprises third and fourth anchor points, wherein the headgear includes four straps structured to be anchored to the first, second, third and fourth anchor points, respectively.

122. The mask system according to claim 114, wherein the frame is an exoskeletal frame.

123. The mask system according to claim 114, wherein the elbow includes a passage wall and a vent wall that extends away from the passage wall, the vent wall including at least one aperture therethrough, the at least one aperture lying at an angle to an outlet direction of air flowing out of the elbow.

124. The mask system according to claim 123, wherein the frame has a rearwardly projecting rib that engages the combined shell and cushion.

125. The mask system according to claim 124, further comprising a securing mechanism to secure the combined shell and cushion and the frame.

126. The mask system according to claim 125, wherein a portion of the combined shell and cushion is sandwiched between the securing mechanism and the frame.

127. The mask system according to claim 126, wherein the securing mechanism passes through the portion of the combined shell and cushion.

128. The mask system according to claim 114, wherein the elbow is freely rotatable when mounted on the mask system.

129. The mask system according to claim 114, wherein the cushion comprises a nasal or full face cushion.

130. A mask system for treating sleep disordered breathing, comprising:
headgear;
a frame having a plurality of anchor points to connect the headgear;
a combined shell and cushion coupled to the frame and defining an interior breathing chamber, the combined shell and cushion comprising a cushion adapted to form a seal on the patient's face and, on the opposing side, a shell having an integrally formed and centrally located rigid retaining ring with a raised rim; and
an elbow rotatably directly connected to the retaining ring and having a first end fitted with a swivel connector for connecting a conduit providing air flow to the mask and a second end, a portion of the second end extending into the breathing chamber beyond the raised rim, the elbow including at least one undercut proximal the second end, the at least one undercut to retainably engage the raised rim of the retaining ring.

131. The mask system according to claim 130, wherein the headgear comprises a multi-layered one-piece construction.

132. The mask system according to claim 131, wherein the elbow includes an approximately 90° bend between the first and second ends thereof.

133. The mask system according to claim 132, wherein the anchor points are proximate to lower rounded corners of the frame.

134. The mask system according to claim 133, wherein the retaining ring and the frame comprise a common material.

135. The mask system according to claim 134, wherein the elbow comprises polycarbonate.

136. The mask system according to claim 134, wherein the retaining ring, the elbow and the frame comprise a common material.

137. The mask system according to claim 130, wherein the frame includes first and second anchor points, and the mask system further comprises third and fourth anchor points, wherein the headgear includes four straps structured to be anchored to the anchor points.

138. The mask system according to claim 130, wherein the frame is an exoskeletal frame.

139. The mask system according to claim 130, wherein the elbow includes a passage wall and a vent wall that extends away from the passage wall, the vent wall including at least one aperture therethrough, the at least one aperture lying at an angle to an outlet direction of air flowing out of the elbow.

140. The mask system according to claim 139, wherein the frame has a rearwardly projecting rib that engages the combined shell and cushion.

141. The mask system according to claim 140, further comprising a securing mechanism to secure the combined shell and cushion and the frame.

142. The mask system according to claim 141, wherein the combined shell and cushion is sandwiched between the securing mechanism and the frame.

143. The mask system according to claim 142, wherein the securing mechanism passes through a portion of the combined shell and cushion.

144. The mask system according to claim 130, wherein the elbow is freely rotatable when mounted on the mask system.

145. The mask system according to claim 130, wherein the cushion comprises a nasal or full face cushion.

* * * * *